US012453819B2

(12) United States Patent
Travanty et al.

(10) Patent No.: US 12,453,819 B2
(45) Date of Patent: Oct. 28, 2025

(54) INJECTOR

(71) Applicant: Antares Pharma, Inc., Ewing, NJ (US)

(72) Inventors: Michael Travanty, S. Minneapolis, MN (US); Steven W. Mattix, Golden Valley, MN (US)

(73) Assignee: Antares Pharma, Inc., Ewing, NJ (US)

( * ) Notice: Subject to any disclaimer, the term of this patent is extended or adjusted under 35 U.S.C. 154(b) by 356 days.

(21) Appl. No.: 17/262,676

(22) PCT Filed: Jul. 24, 2019

(86) PCT No.: PCT/US2019/043281
§ 371 (c)(1),
(2) Date: Jan. 22, 2021

(87) PCT Pub. No.: WO2020/036717
PCT Pub. Date: Feb. 20, 2020

(65) Prior Publication Data

US 2021/0308380 A1 Oct. 7, 2021

Related U.S. Application Data

(60) Provisional application No. 62/702,661, filed on Jul. 24, 2018.

(51) Int. Cl.
*A61M 5/20* (2006.01)
*A61K 31/485* (2006.01)
*A61M 5/32* (2006.01)

(52) U.S. Cl.
CPC ......... *A61M 5/2053* (2013.01); *A61K 31/485* (2013.01); *A61M 5/3202* (2013.01); *A61M 5/326* (2013.01)

(58) Field of Classification Search
CPC .. A61M 5/2053; A61M 5/3203; A61M 5/326; A61M 5/2033; A61M 5/31571;
(Continued)

(56) References Cited

U.S. PATENT DOCUMENTS 5,295,965 A 3/1994 Wilmot
5,658,258 A 8/1997 Pearson et al.
(Continued)

FOREIGN PATENT DOCUMENTS

CN 1565450 A * 1/2005
EP 956058 B1 10/1996
(Continued)

OTHER PUBLICATIONS

Translation of Decision of Refusal dated Oct. 13, 2022 for related Japanese Application No. 2021-503550, 2 pages.
(Continued)

*Primary Examiner* — Laura A Bouchelle
*Assistant Examiner* — Sarah Dympna Grasmeder
(74) *Attorney, Agent, or Firm* — Morgan, Lewis & Bockius LLP

(57) ABSTRACT

An injector including: a housing, a cap detachably coupled to the housing, a ram assembly having a ram configured to pressurize a medicament container for expelling a medicament therefrom, the ram assembly including a trigger engagement member, an energy source associated with the ram for powering the ram to expel medicament from the medicament container, a trigger member disposed about an axis, the trigger member moveable between a pre-firing configuration and a firing configuration, wherein medicament is expelled from the medicament container when the trigger member is in the firing configuration, a needle guard moveably coupled to the housing, the needle guard movable between a storage position and a pre-injection position, wherein the needle guard moves from the storage position to the pre-injection position as the cap is detached from the housing.

26 Claims, 44 Drawing Sheets

(58) Field of Classification Search
CPC ........ A61M 5/20; A61M 5/30; A61M 5/3204; A61M 2005/2013; A61M 2005/3247; A61M 2005/3267; A61K 31/485
See application file for complete search history.

(56) References Cited

U.S. PATENT DOCUMENTS

| | | | |
|---|---|---|---|
| 6,210,369 | B1 | 4/2001 | Wilmot et al. |
| 6,805,686 | B1 | 10/2004 | Fathallah et al. |
| 6,976,976 | B2 | 12/2005 | Doyle |
| 7,449,012 | B2 | 11/2008 | Young et al. |
| 7,488,308 | B2 | 2/2009 | Lesch, Jr. |
| 7,500,963 | B2 | 3/2009 | Westbye et al. |
| 7,794,432 | B2 | 9/2010 | Young et al. |
| 7,811,261 | B2 | 10/2010 | Rubinstein et al. |
| 7,824,379 | B2 | 11/2010 | Doyle |
| 8,048,035 | B2 | 11/2011 | Mesa et al. |
| 8,110,209 | B2 * | 2/2012 | Prestrelski ........... A61K 9/0021 424/423 |
| 8,241,255 | B2 | 8/2012 | Doyle |
| 8,251,947 | B2 | 8/2012 | Kramer et al. |
| 8,376,998 | B2 | 2/2013 | Daily et al. |
| 8,496,619 | B2 | 7/2013 | Kramer et al. |
| 8,579,865 | B2 | 11/2013 | Wotton et al. |
| 8,591,465 | B2 | 11/2013 | Hommann |
| 8,696,618 | B2 | 4/2014 | Kramer et al. |
| 8,734,402 | B2 | 5/2014 | Sharp et al. |
| 8,801,674 | B2 | 8/2014 | Rolfe et al. |
| 8,870,827 | B2 | 10/2014 | Young et al. |
| 8,900,200 | B2 | 12/2014 | Doyle |
| 8,945,063 | B2 | 2/2015 | Wotton et al. |
| 9,033,933 | B2 | 5/2015 | Boyd et al. |
| 9,216,256 | B2 | 12/2015 | Olson et al. |
| 9,220,847 | B2 | 12/2015 | Holmqvist et al. |
| 9,233,213 | B2 | 1/2016 | Olson et al. |
| 9,364,610 | B2 | 6/2016 | Kramer et al. |
| 9,364,611 | B2 | 6/2016 | Kramer et al. |
| 9,375,536 | B2 | 6/2016 | Doyle |
| 9,446,195 | B2 | 9/2016 | Kramer et al. |
| 9,526,845 | B2 | 12/2016 | Roberts et al. |
| 9,586,007 | B2 | 3/2017 | Roervig et al. |
| 9,586,010 | B2 | 3/2017 | Mesa et al. |
| 9,616,183 | B2 | 4/2017 | Wozencroft |
| 9,656,025 | B2 | 5/2017 | Bostrom et al. |
| 9,744,302 | B2 | 8/2017 | Travanty |
| 9,750,881 | B2 | 9/2017 | Wotton et al. |
| 9,808,582 | B2 | 11/2017 | Kramer et al. |
| 9,844,634 | B2 | 12/2017 | Lewkonya et al. |
| 9,867,949 | B2 | 1/2018 | Sund et al. |
| 9,895,496 | B2 | 2/2018 | Doyle |
| 9,901,680 | B2 | 2/2018 | Roervig et al. |
| 9,907,910 | B2 | 3/2018 | Constantineau et al. |
| 9,907,911 | B2 | 3/2018 | Constantineau et al. |
| 9,925,335 | B2 | 3/2018 | Constantineau et al. |
| 9,950,115 | B2 | 4/2018 | Standley et al. |
| 9,950,125 | B2 | 4/2018 | Wotton et al. |
| 9,987,436 | B2 | 6/2018 | Giambattista et al. |
| 10,105,496 | B2 | 10/2018 | Aneas |
| 10,124,115 | B2 | 11/2018 | Swanson et al. |
| 10,220,147 | B2 | 3/2019 | Constantineau et al. |
| 10,238,662 | B2 | 3/2019 | Wotton et al. |
| 10,238,810 | B2 | 3/2019 | Daily et al. |
| 10,252,005 | B2 | 4/2019 | Row et al. |
| 10,272,203 | B2 | 4/2019 | Holmqvist |
| 10,279,131 | B2 | 5/2019 | Kramer et al. |
| 10,300,198 | B2 | 5/2019 | Constantineau et al. |
| 10,300,199 | B2 | 5/2019 | Standley et al. |
| 10,335,554 | B2 | 7/2019 | Rubinstein et al. |
| 10,350,364 | B2 | 7/2019 | Standley et al. |
| 10,357,609 | B2 | 7/2019 | Kramer et al. |
| 10,357,617 | B2 | 7/2019 | Holmqvist |
| 10,485,931 | B2 | 11/2019 | Olson et al. |
| 10,493,215 | B2 | 12/2019 | Giambattista et al. |
| 10,500,348 | B2 | 12/2019 | Olson et al. |
| 10,525,213 | B2 | 1/2020 | Stefanov |
| 10,537,680 | B2 | 1/2020 | Constantineau et al. |
| 10,555,954 | B2 | 2/2020 | Wotton et al. |
| 2004/0225262 | A1 | 11/2004 | Fathallah et al. |
| 2005/0171477 | A1 | 8/2005 | Rubin et al. |
| 2005/0251850 | A1 | 11/2005 | Kiehn et al. |
| 2010/0298770 | A1 | 11/2010 | Rubinstein et al. |
| 2011/0137247 | A1 | 6/2011 | Mesa et al. |
| 2012/0046609 | A1 | 2/2012 | Mesa et al. |
| 2012/0101475 | A1 | 4/2012 | Wilmot et al. |
| 2013/0035644 | A1 | 2/2013 | Giambattista et al. |
| 2014/0228769 | A1 | 8/2014 | Karlsson et al. |
| 2014/0257200 | A1 | 9/2014 | Auerbach et al. |
| 2014/0303556 | A1 * | 10/2014 | Travanty ................. A61P 15/08 604/111 |
| 2015/0011944 | A1 | 1/2015 | Young et al. |
| 2015/0073383 | A1 | 3/2015 | Wilmot et al. |
| 2015/0174061 | A1 * | 6/2015 | Wyse ..................... A61K 47/12 514/282 |
| 2015/0290400 | A1 | 10/2015 | Roberts et al. |
| 2016/0067144 | A1 | 3/2016 | Chang |
| 2016/0158460 | A1 | 6/2016 | Mesa et al. |
| 2016/0325044 | A1 | 11/2016 | Tschirren et al. |
| 2016/0346487 | A1 | 12/2016 | Kramer et al. |
| 2017/0106146 | A1 | 4/2017 | Folk et al. |
| 2017/0173269 | A1 | 6/2017 | Wozencroft |
| 2017/0173271 | A1 | 6/2017 | Young et al. |
| 2017/0182250 | A1 | 6/2017 | Bostrom et al. |
| 2018/0001025 | A1 | 1/2018 | Sarkinen et al. |
| 2018/0028753 | A1 | 2/2018 | Wilmot et al. |
| 2018/0043108 | A1 | 2/2018 | Mesa et al. |
| 2018/0050156 | A1 | 2/2018 | Travanty |
| 2018/0093045 | A1 | 4/2018 | Mehawej et al. |
| 2018/0110931 | A1 | 4/2018 | Standley et al. |
| 2018/0161501 | A1 | 6/2018 | Standley et al. |
| 2018/0161521 | A1 | 6/2018 | Sanders et al. |
| 2018/0161522 | A1 | 6/2018 | Sanders et al. |
| 2018/0193562 | A1 | 7/2018 | Gibson et al. |
| 2018/0221584 | A1 * | 8/2018 | Grimoldby ....... A61M 5/31505 |
| 2018/0272073 | A1 | 9/2018 | Giambattista et al. |
| 2019/0030260 | A1 | 1/2019 | Wotton et al. |
| 2019/0046728 | A1 | 2/2019 | Swanson et al. |
| 2019/0224215 | A1 | 7/2019 | Wotton et al. |
| 2019/0240407 | A1 | 8/2019 | Constantineau et al. |
| 2019/0240415 | A1 | 8/2019 | Holmqvist |
| 2019/0255257 | A1 | 8/2019 | Daily et al. |
| 2019/0262542 | A1 | 8/2019 | Row et al. |
| 2019/0275250 | A1 | 9/2019 | Constantineau et al. |
| 2019/0374717 | A1 | 12/2019 | Swanson et al. |
| 2019/0381255 | A1 | 12/2019 | Young et al. |
| 2019/0388623 | A1 | 12/2019 | Rubinstein et al. |
| 2020/0023141 | A1 | 1/2020 | Giambattista et al. |
| 2020/0054838 | A1 | 2/2020 | Olson et al. |
| 2020/0054840 | A1 | 2/2020 | Olson et al. |

FOREIGN PATENT DOCUMENTS

| | | | |
|---|---|---|---|
| EP | 1039942 | B1 | 10/2004 |
| EP | 1487522 | B1 | 7/2009 |
| EP | 2204201 | A1 | 7/2010 |
| EP | 1680160 | B1 | 7/2013 |
| EP | 2311510 | B1 | 5/2014 |
| EP | 2179759 | B1 | 11/2015 |
| EP | 1786491 | B1 | 2/2016 |
| EP | 2471564 | B1 | 3/2016 |
| EP | 2381987 | B1 | 6/2016 |
| EP | 3079740 | A2 | 10/2016 |
| EP | 2650033 | B1 | 11/2016 |
| EP | 2978471 | B1 | 4/2017 |
| EP | 2968768 | B1 | 8/2017 |
| EP | 2488237 | B1 | 4/2018 |
| EP | 2866857 | B1 | 4/2018 |
| EP | 3096819 | B1 | 6/2018 |
| EP | 2531238 | B1 | 8/2018 |
| EP | 1646414 | B1 | 9/2018 |
| EP | 2983748 | B1 | 12/2018 |
| EP | 3434305 | A1 | 1/2019 |
| EP | 3310413 | B1 | 2/2019 |
| EP | 2654845 | B1 | 4/2019 |
| EP | 2934628 | B1 | 9/2019 |

(56) References Cited

FOREIGN PATENT DOCUMENTS

| | | | |
|---|---|---|---|
| EP | 3566733 | A1 | 11/2019 |
| EP | 3183015 | B1 | 1/2020 |
| EP | 3183016 | B1 | 1/2020 |
| EP | 3235530 | B1 | 1/2020 |
| JP | 2006-511582 | A | 4/2006 |
| JP | 2016-507305 | A | 3/2016 |
| JP | 2018-502653 | A | 2/2018 |
| WO | 9714455 | | 4/1997 |
| WO | 9930759 | | 6/1999 |
| WO | 200382386 | A1 | 10/2003 |
| WO | 2005104424 | A1 | 7/2004 |
| WO | 200509520 | A1 | 2/2005 |
| WO | 200525636 | A2 | 3/2005 |
| WO | 200544344 | A1 | 5/2005 |
| WO | 200617732 | A2 | 2/2006 |
| WO | 2009148969 | A1 | 12/2009 |
| WO | 201076569 | A2 | 7/2010 |
| WO | 201147298 | A2 | 4/2011 |
| WO | 201195486 | A1 | 8/2011 |
| WO | 2012000839 | A2 | 1/2012 |
| WO | 201285580 | A1 | 6/2012 |
| WO | 2012096620 | A1 | 7/2012 |
| WO | 2013012745 | A1 | 1/2013 |
| WO | 201332389 | A1 | 3/2013 |
| WO | 2014001319 | A1 | 1/2014 |
| WO | 201495424 | A1 | 6/2014 |
| WO | 2014139939 | A1 | 9/2014 |
| WO | 2014150201 | A1 | 9/2014 |
| WO | 2014154490 | A2 | 10/2014 |
| WO | 2014164823 | A1 | 10/2014 |
| WO | 201573740 | A2 | 5/2015 |
| WO | 2015107180 | A1 | 7/2015 |
| WO | 201603813 | A1 | 1/2016 |
| WO | 201628814 | A2 | 2/2016 |
| WO | 201628815 | A1 | 2/2016 |
| WO | 201628817 | A2 | 2/2016 |
| WO | 201628820 | A1 | 2/2016 |
| WO | 2016040360 | A1 | 3/2016 |
| WO | 201651395 | A1 | 4/2016 |
| WO | 201678864 | A1 | 5/2016 |
| WO | 2016118688 | A1 | 7/2016 |
| WO | 2016138434 | A1 | 9/2016 |
| WO | 2016202555 | A1 | 12/2016 |
| WO | 201727876 | A1 | 2/2017 |
| WO | 2017029032 | A1 | 2/2017 |
| WO | 201762005 | A1 | 4/2017 |
| WO | 2017089259 | A1 | 6/2017 |
| WO | 2018111815 | A1 | 6/2018 |
| WO | 2018111816 | A2 | 6/2018 |
| WO | 2019237082 | A1 | 12/2019 |

OTHER PUBLICATIONS

Supplementary European Search Report for corresponding Application No. EP19850030 dated Mar. 11, 2022, 2 pages.

Translation of Japanese Office Action for corresponding Application No. JP 2021-503550 dated Mar. 10, 2022, 4 pages.

International Search Report and Written Opinion dated Jun. 2, 2020 for International Patent Application No. PCT/US2019/043821, 9 pages.

Third Party Observation for European Application No. EP20190850030, dated Dec. 23, 2022, 7 pages.

Office Action issued in corresponding Japanese Application No. 2023-016519, dated Jan. 16, 2024, 12 pages, with English translation.

Office Action issued in Japanese Patent Application No. 2023-016519, mailed Jul. 31, 2024, 4 pages, with English translation.

* cited by examiner

INJECTOR

CROSS REFERENCE TO RELATED APPLICATIONS

This application is a U.S. National Phase of International Patent Application No. PCT/US2019/043281 filed on Jul. 24, 2019, which claims the benefit of U.S. Provisional Patent Application No. 62/702,661 filed Jul. 24, 2018 entitled "Naloxone Hydrochloride Injection in Pre-Filled Syringe", each of which is incorporated by reference herein in its entirety.

FIELD OF THE DISCLOSURE

The present disclosure relates to an injector and, more particularly, to an injector for injecting a medicament comprising Naloxone.

BACKGROUND OF THE INVENTION

Various injection devices exist that employ an automated mechanism to actuate injection of a liquid medicament into a patient. Examples of such devices include jet injectors (both needle-free and needle-assisted) and traditional, low-pressure auto-injectors (that provide, for example, mechanized delivery of a traditional, finger-powered hypodermic syringe injection). Although the precise mechanisms used to complete an injection can vary, most include a feature that stores kinetic energy that can be used to drive an injection mechanism during use. Further, many injectors include a trigger mechanism configured to ensure that the kinetic energy remains stored until an injection is desired, whereby actuation of the trigger releases the injection mechanism, allowing the stored kinetic energy to drive the injection mechanism to cause injection.

Examples of needle-free jet injectors are described, for example, in U.S. Pat. Nos. 5,599,302 and 4,790,824. These high force injectors are button activated and administer medication as a fine, high velocity jet delivered under sufficient pressure to enable the jet to pass through the skin. The injection mechanism in such needle-free jet injectors can apply a force to a medicament storing chamber within the device such that the pressure required to inject the medicament is created within the chamber.

Traditional self-injectors or auto-injectors like the ones described, for example, in U.S. Pat. Nos. 4,553,962 and 4,378,015 and PCT Publication WO/9714455 inject medicament at a rate and in a manner similar to hand-operated hypodermic syringes. The described self-injectors or auto-injectors have needles that are extended at the time of activation to penetrate the user's skin to deliver medicament through movement of the drug container and related needle. Thus, the mechanism that provides the force to deliver the medicament in traditional, low-pressure self-injectors and auto-injectors can also be used to extend the needle and displace the drug container to cause the insertion of the needle through the user's skin and to apply a force to a plunger movably disposed within the drug container to cause the medicament to be expelled from the container through the needle. The auto-injectors manufactured, for example by Owen Mumford, thus use very low pressures to inject the medicament, which is typically injected through a needle in a relatively slow stream. Another self-injector includes the Simponi injector, which includes a window in the housing through which a yellow ram is visible inside a clear medicament container once the injector has been used.

Additionally, needle-assisted jet injectors have also been developed with higher injection forces that utilize a needle to initially penetrate the skin allowing a range of needle insertion depth at times less than that of a traditional hypodermic injector or low-pressure auto-injectors. Once the skin is penetrated with the needle, a jet mechanism is activated, causing the medicament containing liquid within the injector to be pressurized and expelled through the needle and into the skin. The injection mechanism in needle-assisted jet injectors can be configured to move the drug container and the needle forward to penetrate the skin and exert the necessary injection force to a plunger moveably disposed within the container. Alternatively, the needle and drug container can be positioned to penetrate the skin while keeping the needle and drug container in a stationary position, and the injection mechanism can be structured to pressurize the container. The pressure applied to the medicament within the injector can be less than that of a traditional jet injector, because the outer layers of the skin have already been penetrated by the needle. Similarly, the pressure applied to the medicament is preferably higher than that of a traditional auto-injector or the like, causing the medicament to penetrate the skin and be dispersed into the tissue or injected in the tissue below the skin to a depth that is sufficient so that the medicament remains substantially within the body. An additional benefit of the higher pressure includes a faster time of injection resulting in less psychological trauma to the patient and a decreased likelihood of the user inadvertently terminating the injection prematurely by removing the injector from the injection site.

Because of the stored energy associated with the trigger and injection mechanisms, accidental firing can occur due to sudden movements during shipping or due to mishandling of the device by a user including accidental actuation of the trigger mechanism. Accidental firing of the injection mechanism can cause the medicament to be expelled from the device, which can be at a dangerously high pressure, depending on the type of injection device. Further, accidental firing can cause an injection needle to move forward with respect to the device with sufficient force to penetrate the skin.

Additionally, the dimensions of many components incorporated in injectors typically constrain the design of many injectors. For example, many injectors utilize front firing-initiation mechanisms that typically require an axial translation and engagement with a triggering structure located at the back of the injector. However, this configuration typically promotes binding of the communicating triggering components due to but not limited friction between components in slidable communication and component distortion, which can be advantageous for, e.g., reducing the size of the injection device, being able to view the drug container within the device, etc.

Naloxone is an opioid antagonist, which prevents or reverses the effects of opioids including respiratory depression, sedation and hypotension. Naloxone was approved by FDA in 1971 as Naloxone hydrochloride injection in the brand name of Narcan.

SUMMARY OF THE INVENTION

In some embodiments, the invention may be an injector including a housing, a cap detachably coupled to the housing, a ram assembly having a ram configured to pressurize a medicament container for expelling a medicament therefrom, the ram assembly including a trigger engagement member, an energy source associated with the ram for powering the ram to expel medicament from the medicament container, a trigger member disposed about an axis, the trigger member moveable between a pre-firing configuration and a firing configuration, wherein medicament is expelled from the medicament container when the trigger member is in the firing configuration, a needle guard moveably coupled to the housing, the needle guard movable between a storage position and a pre-injection position, wherein the needle guard moves from the storage position to the pre-injection position as the cap is detached from the housing.

In some embodiments, the injector may include a needle in fluid communication with the medicament container, and a needle shield at least partially surrounding the needle.

In some embodiments, the needle shield may axially extend past the cap in a distal direction.

In some embodiments, the cap may include an end wall with an end wall opening.

In some embodiments, at least a portion of the needle shield may be within the end wall opening when the cap is coupled to the housing.

In some embodiments, the cap may include a needle shield remover which may remove the needle shield from the needle as the cap is detached from the housing.

In some embodiments, the needle guard may move to the pre-injection position as the cap is detached from the housing and the needle shield is removed from the needle.

In some embodiments, an end of the needle guard may be further away from the housing in the pre-injection position than in the storage position.

In some embodiments, an end of the needle guard may be further away from the housing in the storage position than in an injection position.

In some embodiments, the needle guard may be in the pre-injection position before a proximal end of the cap is moved axially beyond a distal end of the needle.

In some embodiments, in the storage position, the trigger member may be in the pre-firing configuration and the needle guard may be partially retracted with respect to the housing.

In some embodiments, the needle guard may move the trigger member in a proximal direction from the pre-firing configuration to the firing configuration wherein the trigger engagement member may be released to allow the energy source to fire the ram.

In some embodiments, the energy source may act on the ram to deliver medicament from the medicament container when the needle guard is in the injection position.

In some embodiments, the needle guard may include a firing initiation member associated with the trigger member and the needle guard may be movable proximally with respect to the housing from the pre-injection position to the injection position. As the needle guard moves proximally, the firing initiation member may move the trigger member from the pre-firing configuration to the firing configuration.

In some embodiments, the injector may include an end cap. The end cap may include a ram holding member that axially retains the ram assembly in a proximal position against action of the energy source in the pre-firing configuration.

In some embodiments, the ram holding member may engage the trigger engagement member to axially retain the ram assembly in a proximal position against action of the energy source in the pre-firing configuration.

In some embodiments, the trigger member may include an aperture and in the firing configuration, the ram may be disengaged from the aperture, and the energy source may overcome the engagement between the trigger engagement member and the ram holding member.

In some embodiments, the ram holding member may include a projection that includes a bulge and a groove that are engaged with the trigger engagement member, and the aperture of the trigger member may retain the engagement of the trigger engagement member with the bulge and groove in the pre-firing configuration.

In some embodiments, the injector may include a container support that is may be for holding the medicament container during injection. The ram assembly may be configured to engage the container support to prevent movement of the ram assembly after an injection.

In some embodiments, the needle guard may be movable to a post injection position, the post injection position being when proximal movement of needle guard is blocked by the ram assembly.

In some embodiments, the medicament may include naloxone or a pharmaceutically acceptable salt thereof.

In some embodiments, the medicament may include naloxone hydrochloride

In some embodiments, the medicament may include 1 mg/mL naloxone hydrochloride

In some embodiments, the medicament may include 5 mg/mL naloxone hydrochloride.

In some embodiments, the medicament may include 0.4 mL naloxone hydrochloride solution.

In some embodiments, the naloxone hydrochloride solution may be an aqueous solution.

BRIEF DESCRIPTION OF THE SEVERAL VIEWS OF THE DRAWINGS

These and other objects, features and advantages of the invention will be apparent from a consideration of the following non-limiting detailed description considered in conjunction with the drawing figures, in which.

Figure 1:
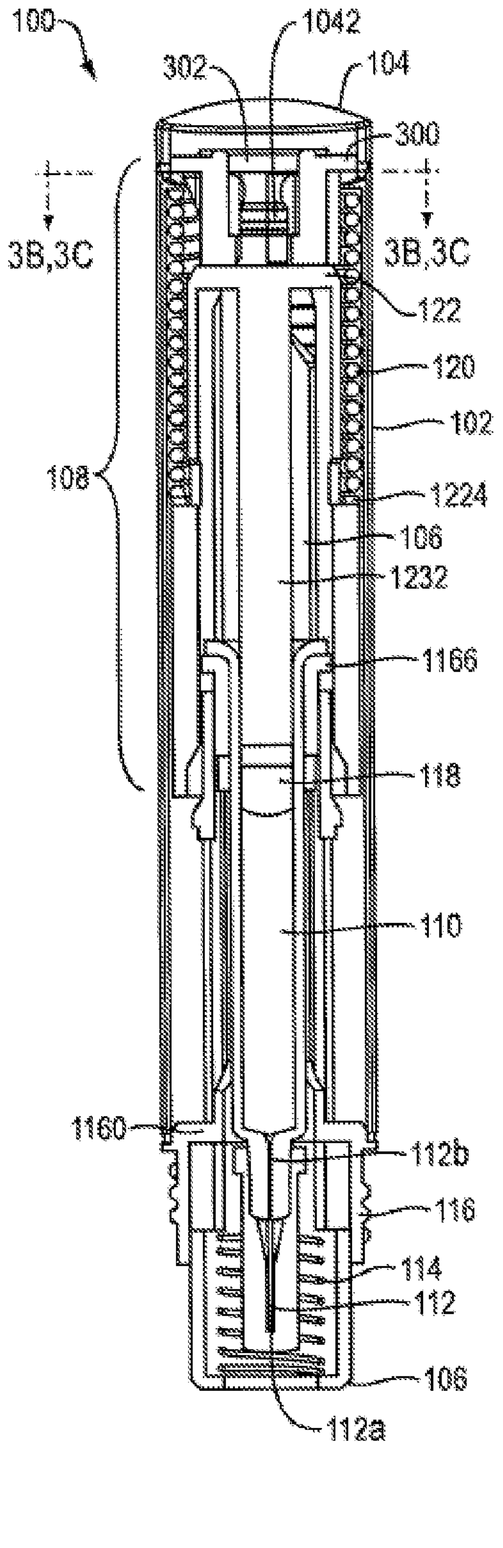
FIG. 1 is a cross-sectional view of an exemplary injection device according to an exemplary embodiment of the present disclosure.

Throughout the figures, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF THE EXEMPLARY EMBODIMENTS OF THE INVENTION

With reference to the accompanying figures, various embodiments of the present invention are described more fully below. Some but not all embodiments of the present invention are shown. Indeed, various embodiments of the invention may be embodied in many different forms and should not be construed as limited to the embodiments expressly described. Like numbers refer to like elements throughout. The singular forms "a," "an," and "the" include the singular and plural unless the context clearly dictates otherwise.

FIG. 1 shows an exemplary injection device 100 according to an exemplary embodiment of the present disclosure. It is noted that, in the context of this disclosure, the terms "distal" and "proximal" are used in reference to the position of the injection device relative to a user of the injection device when held by a user. Accordingly, a point located distal to a second point would be further from the user (i.e., towards an injection end of the injection device) and vice versa. As shown in the drawings, an exemplary injection device 100 is a needle assisted jet injection device, although a person having ordinary skill in the art will understand alternative embodiments employing certain features herein can be configured as needle-free jet injectors, or as low-pressure auto-injectors or other mechanized injectors. According to certain exemplary embodiments, injection device 100 is a one-time disposable needle-assisted jet injector. In certain embodiments, injection device 100 can be modified to provide multiple and/or variable dosings upon repeated injections. According to certain exemplary embodiments, injection device 100 is a one-time disposable needle-assisted jet injector with a lock-out feature. For example, injection device 100 can facilitate a jet injection of medicament stored within injection device 100 and can include a locking feature that prevents a user from attempting to use injection device 100 once the medicament has been dispensed. In one embodiment, the locking feature is activated upon dispensing of the medicament and not upon use of injection device 100. For example, the locking feature can be activated, thus preventing injection device 100 from a subsequent attempted use by a user, even in the case where the injection device was not actually used by a user for an injection, but where a firing mechanism was inadvertently activated (e.g., during transport, handling, etc. of the device) and the medicament was dispensed. Operation of injection device 100, including the locking feature, is described in further detail below.

According to certain exemplary embodiments, injection device 100 can deliver any suitable liquid drug or medicament, including the medicament described herein. In an embodiment, the medicament is the Naloxone formulation described herein. Further, injection device 100 can allow the injection to be administered by individuals that do not have formal training (e.g., self-administered or administered by another individual family member or other caregiver who may not be a formally trained healthcare provider, such as a parent administering a drug to a child). Accordingly, injection device 100 can be useful in situations where self-injections/caregiver administered injections would be beneficial.

In one embodiment, as shown in FIG. 1, the exemplary injection device 100 can include an outer housing 102 and a housing end/end cap 104. As shown in FIG. 1, in one embodiment, the housing end/end cap 104 is coupled to a proximal end of housing 102. Injection device 100 can further include various components and/or assemblies housed within outer housing 102. As shown in FIG. 1, these components can include a guard 106, a container support, such as, e.g., a sleeve 116, a firing mechanism 108, a medicament chamber 110, a needle 112, and a spring 114. As shown in FIG. 1, outer housing 102 can be a single piece component, or alternatively, outer housing 102 multiple piece assembly that can be coupled together, for example, via a snap-fit connection, a press-fit connection, a threaded engagement, adhesives, welding, or the like.

Figure 7B:
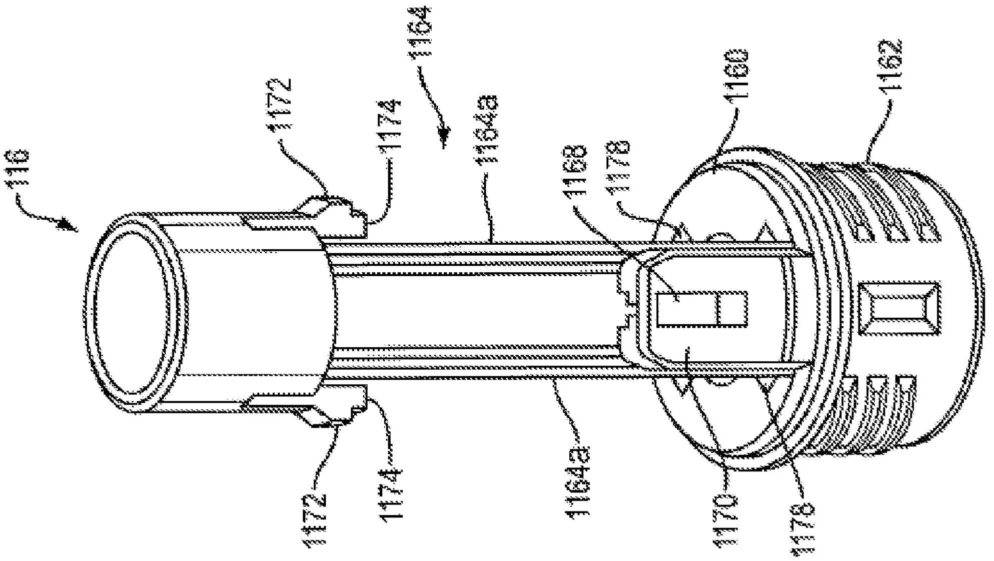
FIGS. 7A and 7B are side and perspective views of a sleeve of an exemplary injection device according to an exemplary embodiment of the present disclosure.
Figure 7A:
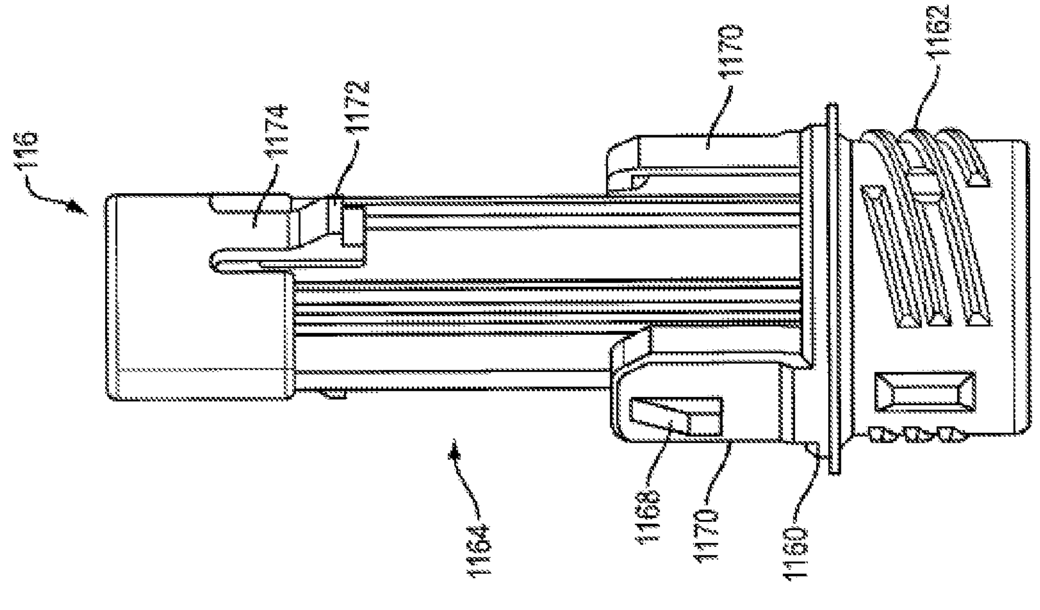

As shown in FIG. 1, in one embodiment, sleeve 116 is at least partially housed within outer housing 102 and mounted to outer housing 102 via, for example, a snap-fit connection, a press-fit connection, a threaded engagement, adhesives, welding, or the like. As shown in FIGS. 7A and 7B, for example, sleeve 116 can include projections 1168 configured to engage openings of housing 102. Sleeve 116 is configured to hold a medicament chamber 110, which can include a needle 112 at a distal end of medicament chamber 110. In certain exemplary embodiments, medicament chamber 110 can include, for example, a separate glass ampule and a needle, or a pre-filled syringe, or sleeve 116 itself can include an integral medicament chamber. In one embodiment, plunger 118 is provided in medicament chamber 110. Plunger 118 is in association with a ram 1232 of firing mechanism 108. During an injection, ram assembly 122 is urged by energy source 120 of firing mechanism 108 to displace plunger 118 distal, deeper into medicament chamber 110, dispensing the medicament through needle 112. In one embodiment, needle 112 includes an injecting tip 112*a* that is configured to penetrate the skin of a user and hollow bore 112*b* that is in fluid communication with medicament chamber 110 to facilitate delivery of medicament from medicament chamber 110 to a user during an injection. FIG. 1 shows injection device 100 in a pre-firing state. The operation of injection device 100, including its various stages and positions, are described in further detail below.

As also shown in FIG. 1, injection device 100 also, in certain embodiments, includes firing mechanism 108. In one embodiment, firing mechanism 108 includes a ram assembly 122 slidably mounted within housing 102 and an energy source 120. In an exemplary embodiment, energy source 120 includes a compression spring, however, other suitable energy source can be used, such as an elastomer or compressed-gas spring, or a gas generator, or other suitable energy storage members. In FIG. 1, ram assembly 122 is in a pre-firing proximal-most position. During an injection, ram assembly 122 is urged distally by energy released by energy source 120. Once an injection is completed, firing ram assembly 122 is disposed in a distal-most position. In this distal position, guard 106 is locked-out and extends over needle tip so that a user cannot attempt a subsequent injection and needle guard 106 can function as sharps protection. Although shown as a single piece, ram assembly 122 can be a multiple piece assembly that can be coupled together, for example, via a snap-fit connection, a press-fit connection, a threaded engagement, adhesives, welding, or other suitable couplings. Ram assembly 122 preferable includes various features that can be configured to facilitate firing of injection device 100 to dispense the medicament stored in medicament chamber 110. According to certain exemplary embodiments of the present disclosure, a trigger mechanism of injection device 100 can include ram assembly 122, floating trigger member 300, which can include retaining portion 306, and ram retaining holding member 1042.

Figure 2:
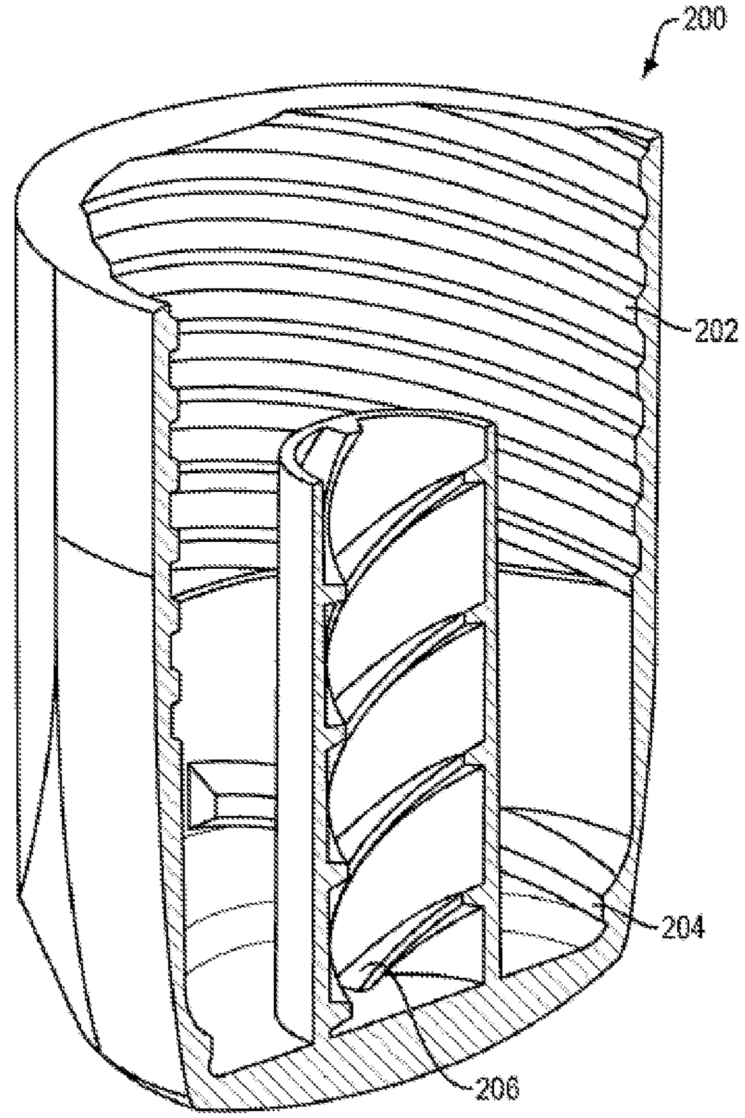
FIG. 2 shows a cross sectional view of a cap of an exemplary injection device according to an exemplary embodiment of the present disclosure.

In one embodiment, injection device 100 includes cap 200, as shown in FIG. 2. cap 200 may be removably affixable to a distal end of outer housing 102. In one embodiment, cap 200 may be removably affixable to the distal end of sleeve 116. For example, cap 200 can be removably affixed to the distal end of housing 102 via a threaded engagement and housing end/end cap 104 can include features (e.g., projections) configured to engage a portion of the proximal end of housing 102 (e.g., openings) to couple housing end/end cap 104 to housing 102. When affixed to injection device 100, cap 200 can ensure that an injection is not triggered by an inadvertent application of a force to guard 106. In one embodiment, cap 200 includes two engagement features. As shown in FIG. 2, cap 200 can include engagement features 202 and 204. Engagement features 202 and 204 can be threads configured to threadedly engage other features of injection device 100. For example, engagement feature 202 can be configured to secure cap 200 to the distal end of housing 102 or be configured to threadedly engage a distal portion of sleeve 116. In one embodiment, engagement feature 204 can be configured to threadedly engage features (e.g., threads) of guard 106 to prevent proximal displacement of guard 106.

As shown in FIG. 2, cap 200 has any regular or irregular shape and may be non-circular in cross-section viewed along its axis and in the initial, closed position aligns with or substantially matches the shape of the portion of the housing adjacent thereto. In one embodiment, features 202 and 204 may include a plurality of threads, having more than one thread starting point, only one of which will result in the cap lining up with the housing as in the initial closed position. Consequently, if the cap is removed and replaced, there is a chance that an incorrect starting point will be selected by the user, resulting in the cap no longer aligning with the injector housing, and providing an indication of tampering. In one embodiment, three threads are used, so there is a two in three chance that a removed and replaced cap will become immediately obvious based on an ill-fitting cap.

As shown in FIG. 1, in one embodiment, housing 102 includes openings configured to engage with sleeve 116 to couple and secure sleeve 116 to housing 102 and includes at least one window that can provide a visual indication of whether or not injection device 100 has been fired. For example, in an pre-firing state, the window allows a user to see medicament chamber 110, along with the stored medicament, and in a fired state, the window shows one or more internal components, such as a portion of firing mechanism 108, which can be a color specifically selected to alert the user that injection device 100 has been fired, and is, in one embodiment, sufficiently different than other colors visible to a user (in one embodiment, having ordinary eyesight) on the injector prior to firing, so as to be conspicuously different to, or contrast from, any other colors present or significantly present. For example, in one embodiment, the color differs from all the other components of injection device 100 pre-firing, or visible by the user pre-firing, so as to be conspicuous (e.g., introducing an entirely new color family). In one embodiment, the new color appearing after firing, is from a non-analogous part of the color wheel, or can contrast, or can be a complementary color, with respect to the colors visible on injection device 100. In one embodiment, the new color signifies caution, such as red or orange, etc. In one embodiment, the colors visible on the injector in the pre-firing condition, and, in one embodiment, including when cap 200 is on and/or off the injector, are grays and blues, for instance. In one embodiment, when the injector is fired, the color red is introduced. In one embodiment, this new color can be introduced after firing but prior to guard 106 being locked-out in the extended position.

Figure 3A:
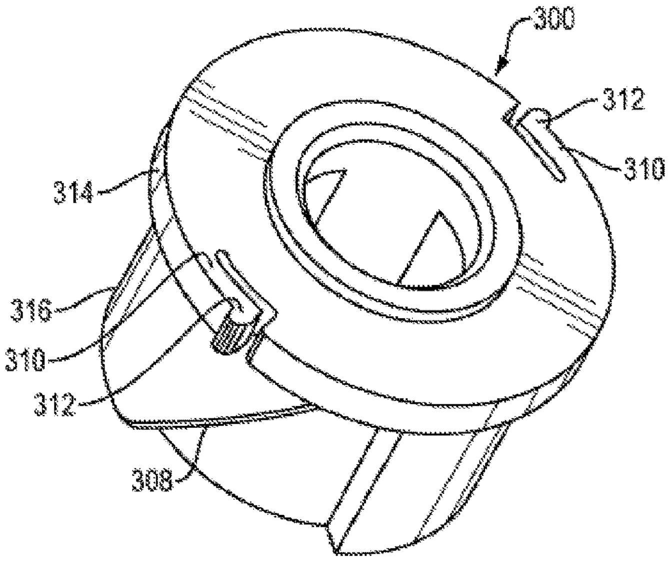
FIG. 3A is a perspective view of a floating trigger member of an exemplary injection device according to an exemplary embodiment of the present disclosure.
Figure 3B:
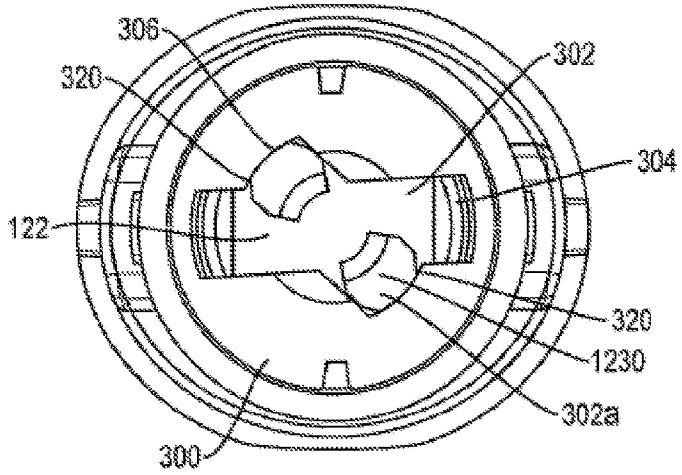
FIG. 3B is a cross-section view at section break 3B, 3C of an exemplary injection device according to an exemplary embodiment of the present disclosure in a ram retaining position.
Figure 3C:
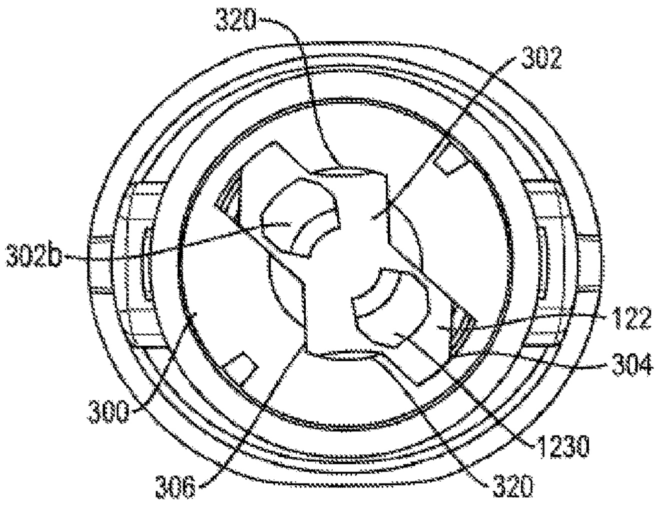
FIG. 3C is a cross-section view at section break 3B,3C of an exemplary injection device according to an exemplary embodiment of the present disclosure in a firing position.

In one embodiment, injection device 100 includes floating trigger member 300, as shown in FIGS. 3A, 3B and 3C. Floating trigger member 300 can have proximal portion 314 and distal portion 316. In one embodiment, floating trigger member 300 can include opening 302. Further, floating trigger member 300 can include opening 302 in distal portion 316. Opening 302 can include retaining portion 306 configured to receive and engage trigger engagement member 1230 of ram assembly 122 in facilitating firing of injection device 100. Opening 302 is, in one embodiment, configured to engage trigger engagement member 1230 of ram assembly 122 such that they are aligned in one of two positions. For example, in first position 302*a* (e.g., retaining position), trigger engagement members 1230 of ram assembly 122 are aligned so that they can be restrained by the retaining portion 306, thereby preventing firing mechanism 108 from firing and dispensing the medicament. In second position 302*b* (e.g., firing position), opening 302 can include firing portions 304 such that the trigger engagement members 1230 of ram assembly 122 are aligned such that trigger engagement members 1230 can splay apart, thereby permitting firing mechanism 108 to fire. FIG. 3B shows trigger engagement members 1230 aligned in the first position (302*a*) and FIG. 3C shows trigger engagement members 1230 aligned in the second position (302*b*). Further, retaining portion 306 of opening 302 (e.g., in the first position 302*a*) is, in one embodiment, curved to facilitate rotation of the floating trigger member 300 from the first and second positions. An exterior surface of distal portion 316 of floating trigger member 300 can include camming surfaces 308. In one embodiment, a portion of trigger engagement members 1230 optionally engage rests 320, such that when floating trigger member 300 rotates, trigger engagement members 1230 disengage rests 320 allowing firing mechanism 108 to fire.

Figure 6A:
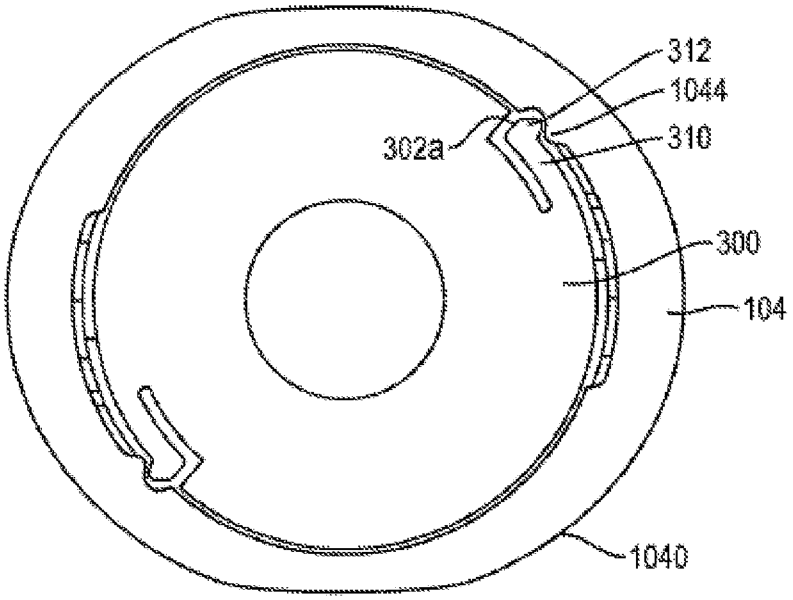
FIG. 6A is a cross-section view at section break 6B, 6C of an end housing portion and floating trigger member of an exemplary injection device according to an exemplary embodiment of the present disclosure in a retaining position.
Figure 6B:
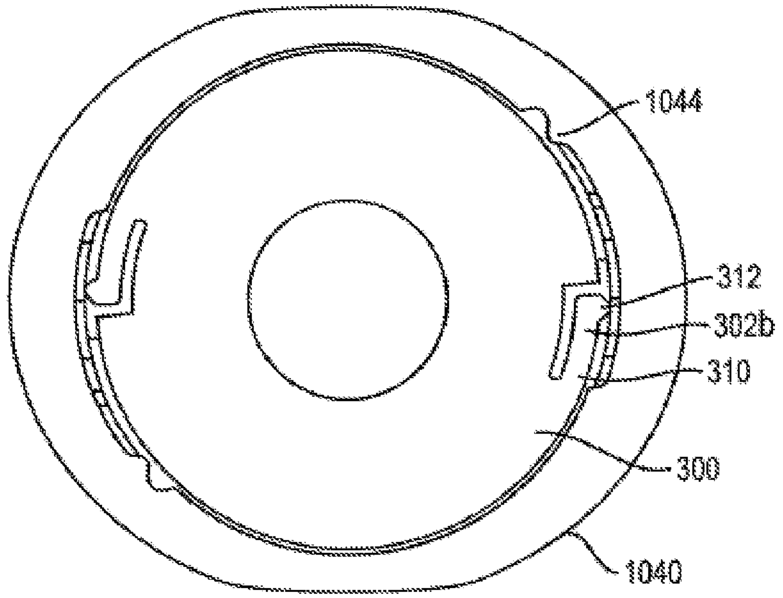
FIG. 6B is a cross-section view at section break 6B, 6C of an end housing portion and floating trigger member of an exemplary injection device according to an exemplary embodiment of the present disclosure in a firing position.

Proximal portion 314 of floating trigger member 300 can include flanges 310 having lips 312, described further below with reference to FIG. 6.

In one embodiment, as shown in FIG. 1, energy source 120 (e.g., a spring) is decoupled from guard 106. In one embodiment, the proximal end energy source 120 is coupled to housing 102. By decoupling energy source 120 from guard 106, the apparent friction of rotation of floating trigger member 300 is significantly reduced. This in turn substantially reduces the amount of force necessary to move guard 106 from an extended position to the firing position as described with reference to FIGS. 9A and 9B, below. Specifically, the compression of components caused by energy source 120 is substantially eliminated thereby significantly reducing the amount of apparent friction and resistance to movement of guard 106 during use of injection device 100.

Figure 4:
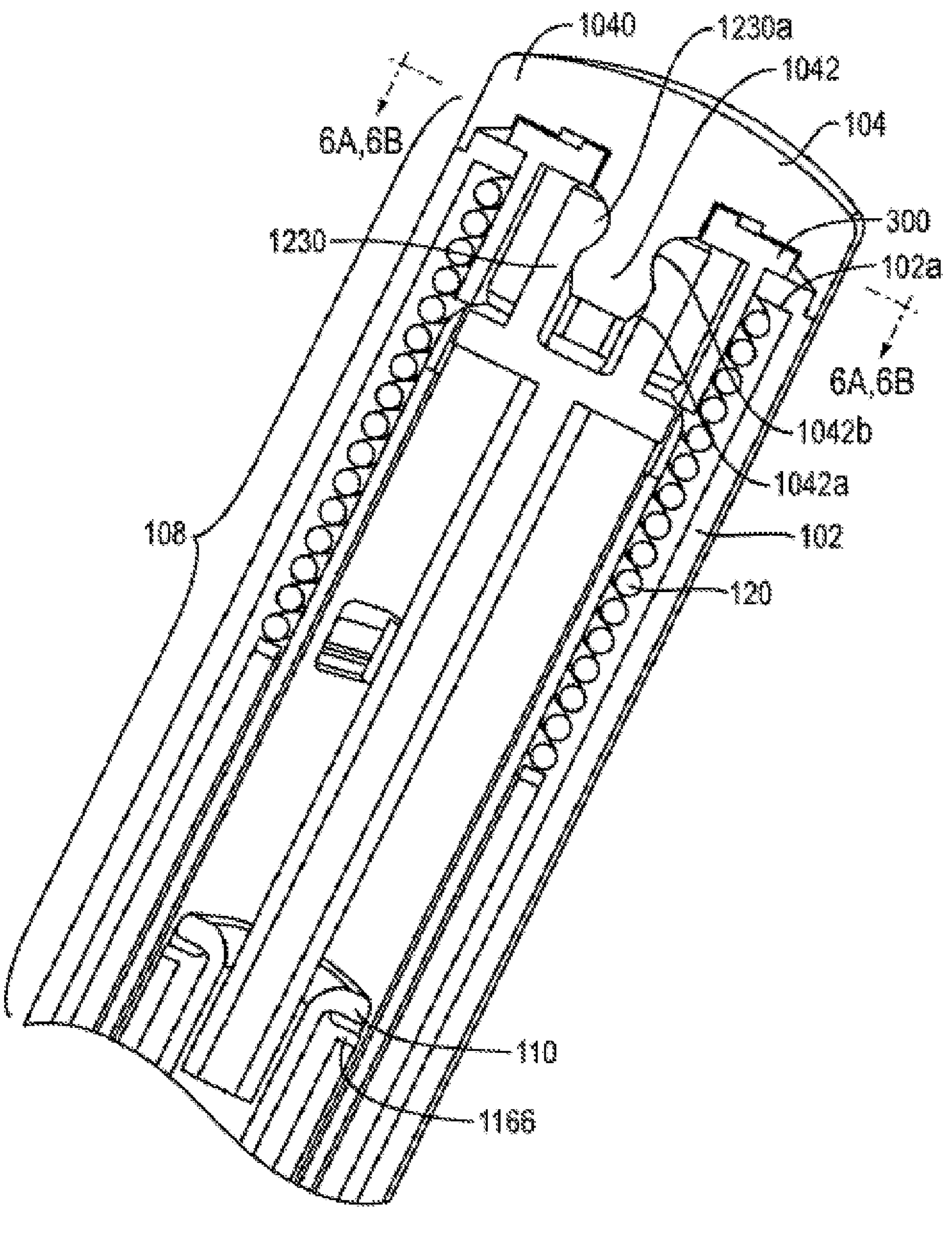
FIG. 4 is a partial cross-sectional view of an exemplary injection device according to an exemplary embodiment of the present disclosure.
Figure 5A:
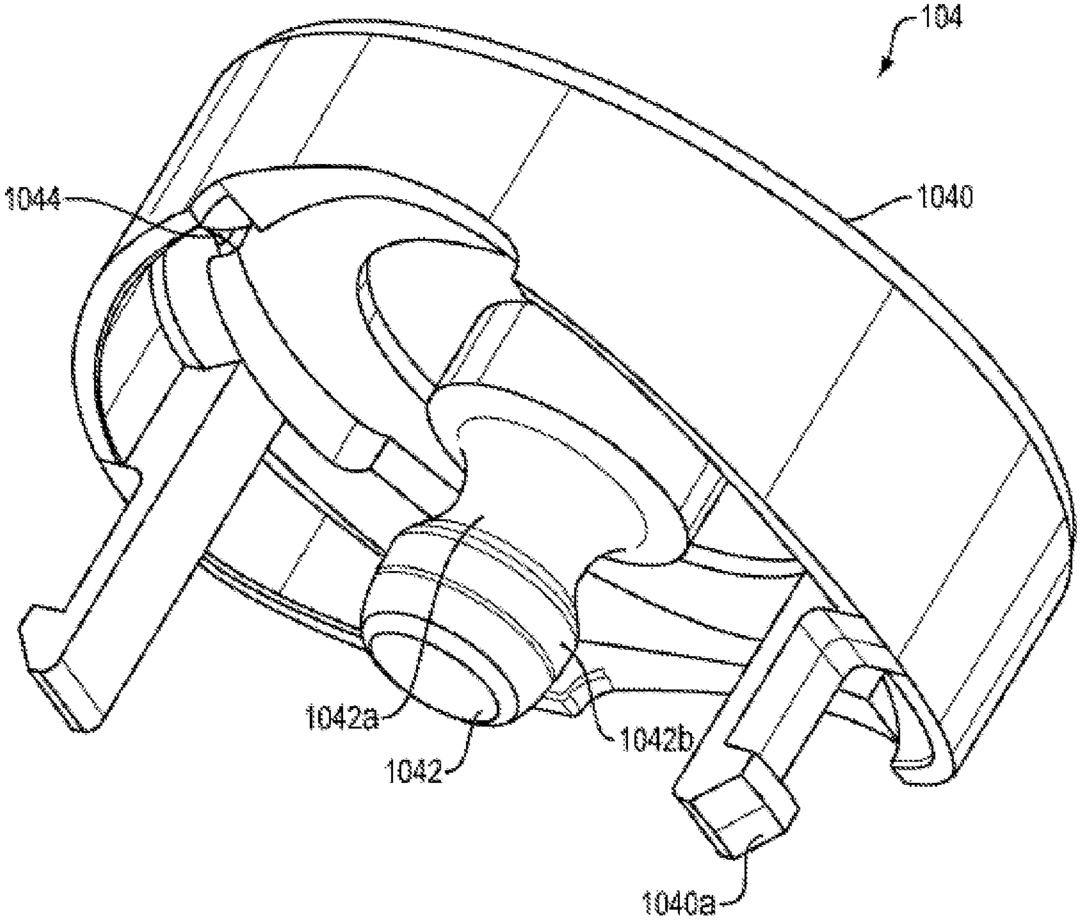
FIG. 5A is a perspective view of an end housing portion of an exemplary injection device according to an exemplary embodiment of the present disclosure.
Figure 5B:
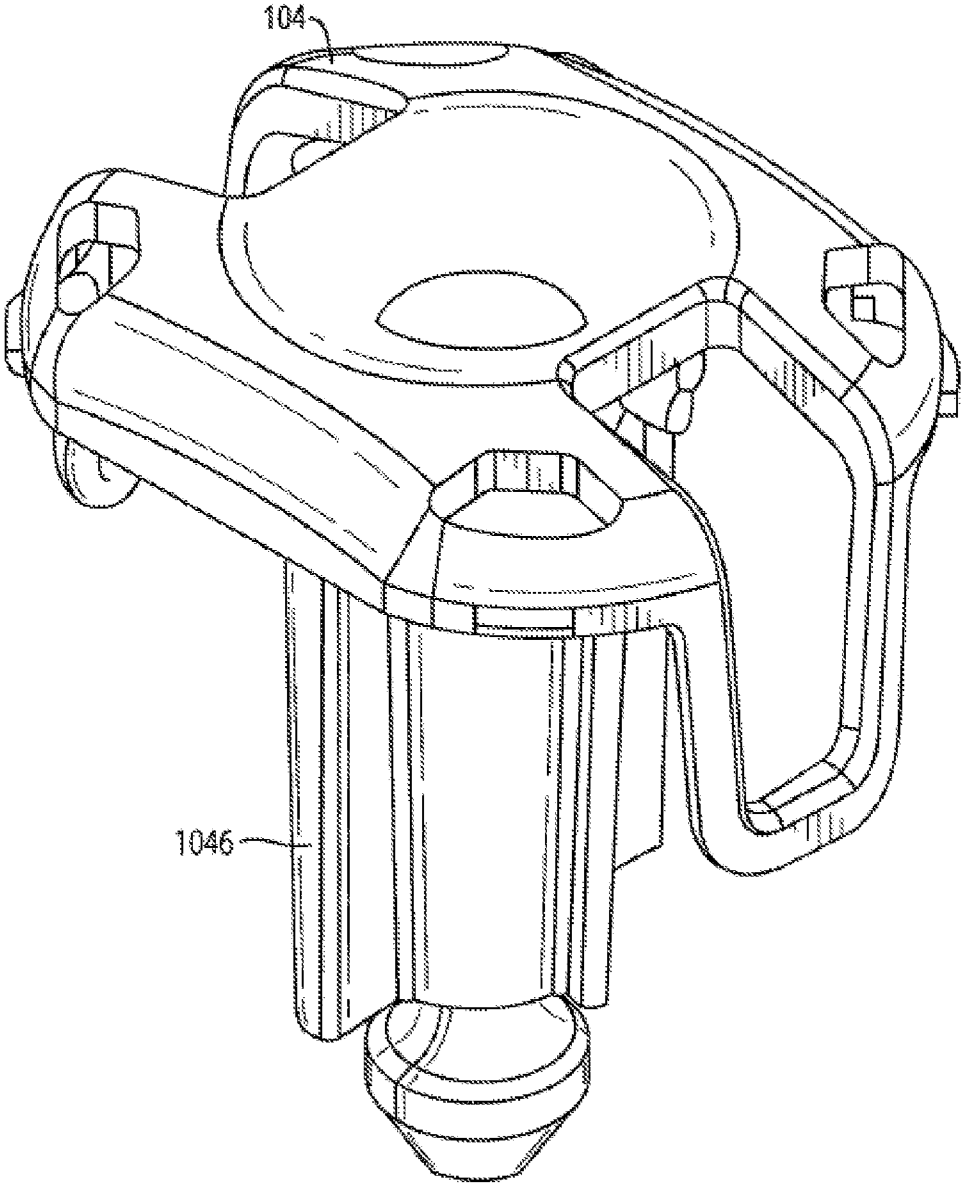
FIG. 5B is a perspective view of an end housing portion of an exemplary injection device according to an exemplary embodiment of the present disclosure.

As shown in FIG. 1, in one embodiment, injection device 100 also includes housing end/end cap 104. One embodiment of a housing end/end cap 104 is shown in FIG. 5A. As shown in FIG. 5A, in one embodiment, housing end/end cap 104 includes a body portion 1040 and a ram holding member 1042. In one embodiment, ram holding member 1042 is a projection, and is configured to engage a trigger engagement member of firing mechanism 108. For example, as shown in FIG. 4, in one embodiment, ram holding member 1042 is a bell-shaped projection, and is engaged with a complementary shaped feature (e.g., projections) 1230*a* of firing mechanism 108. As shown in FIG. 4, in an exemplary embodiment, ram holding member 1042 can include a groove 1042*a* and a bulge 1042*b*, and features 1230*a* of firing mechanism 108 can be configured to align with groove 1042*a* so as to hold bulge 1042*b* to prevent firing of injection device 100. In one embodiment, ram holding member 1042 and the features 1230*a* of firing mechanism 108 engaging with ram holding member 1042 include a circular cross section to allow rotation of the features of firing mechanism 108 relative to ram holding member 1042 during firing of injection device 100. As shown in FIG. 5A, further, body portion 1040 can include projections 1040*a* configured to engage openings in outer housing 102 to couple housing end/end cap 104 to housing 102. FIG. 5B shows another embodiment of a housing end/end cap 104.

In an exemplary embodiment, housing end/end cap 104 optionally includes an engagement member 1044, as shown in FIG. 5A. As further detailed in FIGS. 6A and 6B, the engagement member 1044 engages lip 312 of floating trigger member 300 when floating trigger member 300 is rotated from the first position to the second position. In certain embodiments having engagement member 1044 and lip 312, a threshold breakaway force is needed to overcome the resistance on floating trigger member 300 caused by the engagement portion 1044 when floating trigger member 300 is moved at least partially from the first position to the second position. In certain embodiments, the breakaway feature serves as a safety to prevent unintended rotation of floating trigger member 300.

Figure 13:
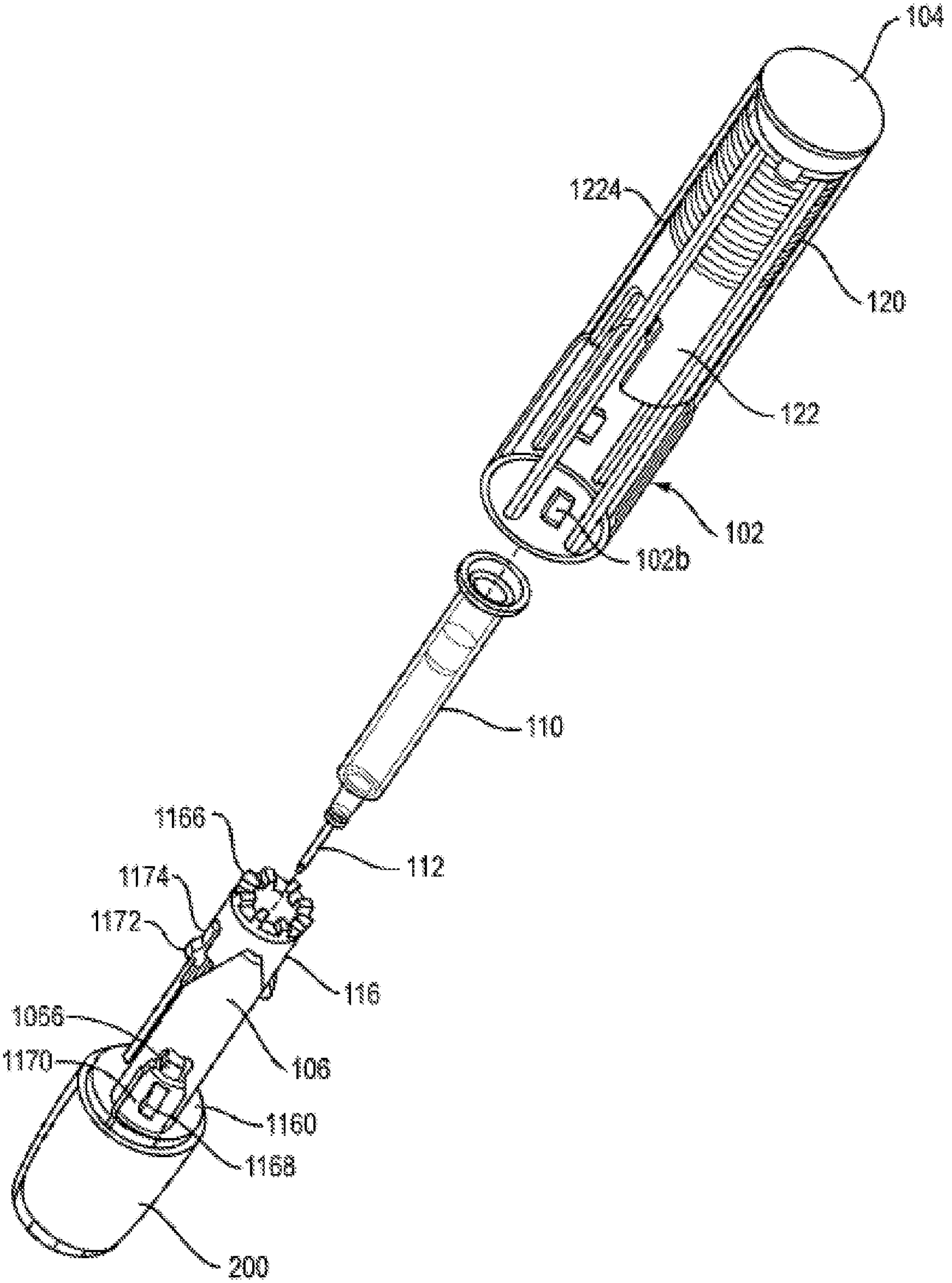
FIG. 13 is an exploded view of an exemplary injection device according to an exemplary embodiment of the present disclosure.

As shown in FIGS. 7A and 7B, in one embodiment, sleeve 116 includes a ring-like structure 1160, a coupling arrangement 1162, and a body portion 1164. Coupling arrangement 1162 can be disposed at a distal portion of sleeve 116 and can be configured to releasably engage cap 200. For example, as seen in FIGS. 1 and 2, coupling arrangement 1162 can include threads configured to provide threaded engagement between sleeve 116 and cap 200. Further, sleeve 116 can include a body portion 1164 configured to secure medicament chamber 110. Body portion 1164 can include guides, such as grooves 1164*a*, configured to engage with features of guard 106 to align and guide axial displacement of guard 106. As shown in FIG. 13, a proximal end of sleeve 116 can include a medicament chamber support 1166 configured to support and secure a proximal portion of medicament chamber 110. For example, support 1166 can be configured as a syringe support configured to hold a proximal end of syringe (e.g., flanges of a prefilled syringe) and can support medicament chamber 110 during the forces exerted on it during firing. Further, support 1166 can include an elastomer or a rubber, and can be configured to distribute the force exerted on surfaces of the medicament chamber 110 during an injection and protect the medicament container from shock during transport or inadvertent damage during use. Additionally, as shown in FIGS. 7A and 13, sleeve 116 can include various features, such as projections 1168, configured to couple sleeve 116 to outer housing 102. For example, projections 1168 can be concentrically symmetrical and configured to engage openings 102*b* in outer housing 102 to secure sleeve 116 to outer housing 102. In an exemplary embodiment, projections 1168 can be disposed on legs 1170, which can be concentrically symmetrical and configured to engage with features of outer housing 102. Additionally, sleeve 116 can include locking features, such as locking projections 1172, disposed on legs 1174, which can be concentrically symmetrical, and can be configured to engage with features of guard 106 of firing mechanism 108 resulting in locking out injection device 100 to prevent a user from attempting to use an already-fired injection device 100.

In one embodiment, ring-like structure 1160 includes several features configured to engage sleeve 116 with medicament chamber 110 (e.g., a glass medicament chamber 110), firing mechanism 108, and guard 106. For example, ring-like structure 1160 can include an opening through which needle 112 can be received. Further, ring-like structure 1160 can include concentrically symmetrical openings 1178 which can be configured to receive legs of guard 106. Additionally, ring-like structure 1160 can be configured to support a distal portion of medicament chamber 110 and engage firing mechanism 108 in preventing further axial displacement of firing mechanism 108 during dispensing of the medicament. Operations of these components are described in further detail below.

Figure 9B:
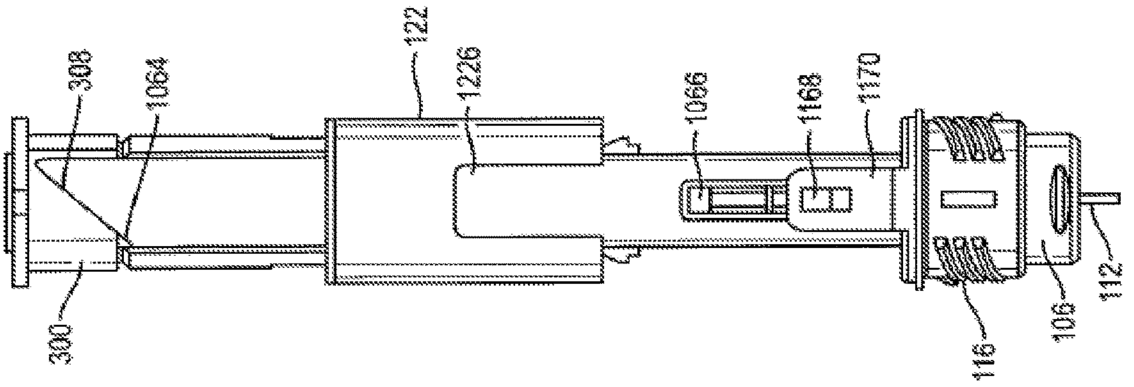
FIGS. 9A and 9B are side views of a ram assembly, needle guard, floating trigger member, sleeve an of an exemplary injection device according to an exemplary embodiment of the present disclosure in unfired and fired positions, respectively.
Figure 9A:
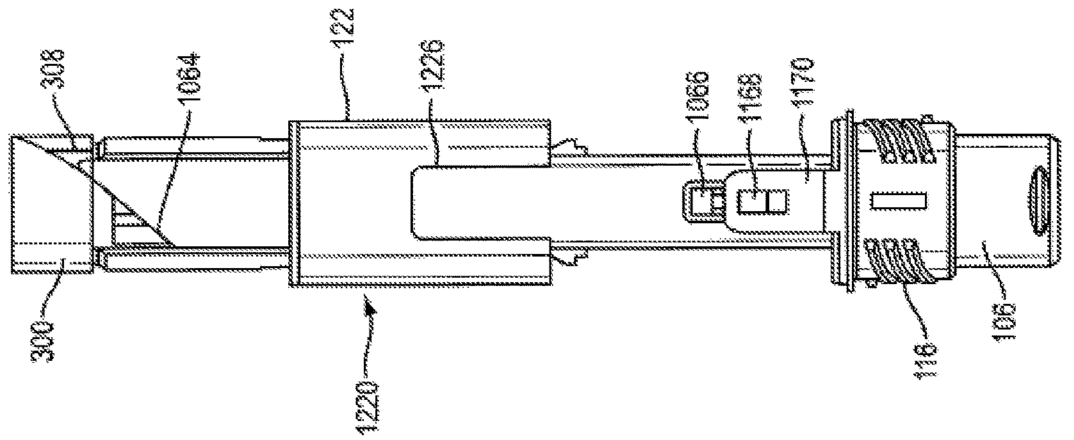

As shown in FIG. 1, in one embodiment, injection device 100 includes a guard 106 slidably mounted at least partially within outer housing 102 and configured to engage trigger member 300 to actuate firing of injection device 100. As shown in FIGS. 9A and 9B, in one embodiment, guard 106 is slidably movable relative to outer housing 102 between an extended (e.g., a distal, protective) position and a retracted (e.g., proximal) position, respectively. In the extended position, guard 106, in one embodiment, covers needle 112, and in the retracted position, needle 112 is not covered by guard 106 and is thereby exposed. For example, FIG. 9A shows guard 106 in the extended position, and FIG. 9B shows guard 106 in the retracted position. As shown in FIG. 1, in one embodiment, guard 106 is resiliently biased toward the extended position via a spring 114, which can be disposed, for example, between a distal surface of ring-like structure 1160 of sleeve 116 and an interior surface of a distal end of guard 106.

In an exemplary embodiment, guard 106 includes a distal portion 1060 and legs 1062. In an exemplary embodiment, the distal end of guard 106 includes a skin-contacting member. Distal portion 1060 includes an opening through which needle 112 can pass and projections 1060*a*. In an exemplary embodiment, projections 1060*a* can be configured to engage engagement features 204 of cap 200 so that guard 106 cannot be proximally displaced when engaged with engagement features 204 of cap 200. In an exemplary embodiment, guard 106 includes a stop surface 1070. In an exemplary embodiment, stop surface 1070 can be configured to abut an inside surface of ring like structure 1160 of sleeve 116 so as to limit the proximal displacement of guard 106. For example, as guard 106 is proximally displaced under a force applied by a user during an injection, stop surface 1070 will come into contact with the inside surface of ring like structure 1160 of sleeve 116 so that guard 106 cannot be further proximally displaced.

Figure 8:
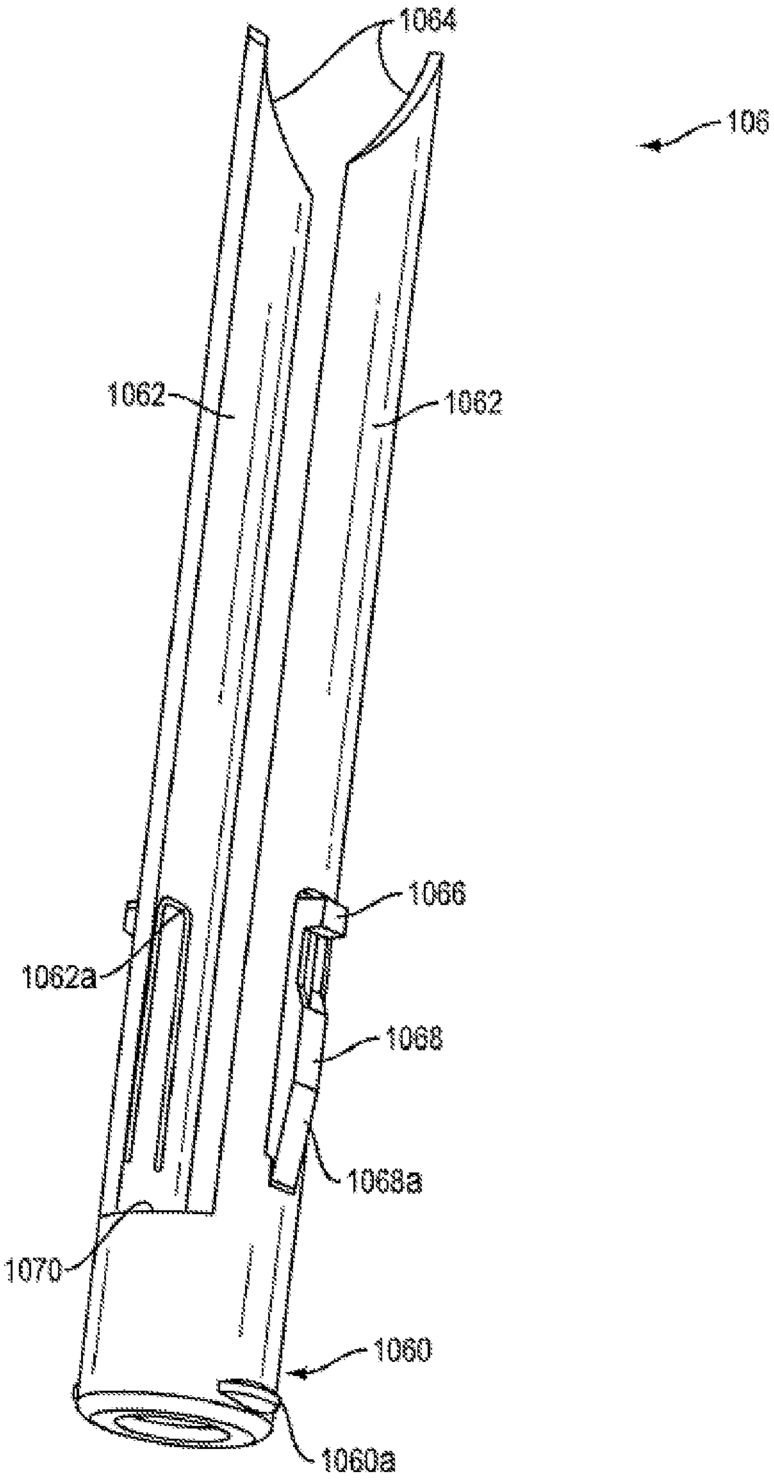
FIG. 8 is a side and perspective views of a needle guard of an exemplary injection device according to an exemplary embodiment of the present disclosure.

In one embodiment, legs 1062 of guard 106 are configured to be received in openings 1178 of ring-like structure 1160. Further, legs 1062 can include ridges 1062*a* configured to engage grooves 1164*a* of sleeve 116, to facilitate alignment and guiding of legs 1062 as guard 106 is axially displaced. As shown in the exemplary embodiment of FIG. 8, legs 1062 also include firing-initiation members, such as camming surfaces 1064 at a proximal end of legs 1062. Cutout 1062*a* may space legs 1062 from the body of guard 106. In an exemplary embodiment, legs 1062 and camming surface 1064 can be concentrically symmetrical. Camming surfaces 1064 are configured to engage trigger member 300 in initiating a firing of injection device 100 and performing an injection of the medicament stored in medicament chamber 110. The proximal ends of legs 1062 can also be sloped to facilitate legs 1062 being received within firing mechanism 108 when guard 106 is displaced from the extended position to the retracted position. As shown in FIGS. 9A and 9B, in an exemplary embodiment, the camming surfaces 1064 are configured to engage camming surfaces 308 of the floating trigger member 300. In one embodiment, legs 1062 include projections 1066 disposed on springs 1068 which can also include sloped surfaces 1068*a*. As shown in FIG. 13, projections 1066 can be configured to engage proximal surfaces of legs 1170 of sleeve 116 to oppose a force exerted by spring 114, which biases guard 106 in the extended position. Further, sloped surfaces 1068*a* of legs 1062 of guard 106 can be configured to engage an interior surface of legs 1170 of sleeve 116 so that as guard 106 is displaced from the extended position to the retracted position, sloped surfaces 1068*a* of legs 1062 of guard 106 engage the interior surfaces of legs 1170 of sleeve 116 so as to bias springs 1068 of legs 1062 of guard 106 towards an interior of injection device 100.

FIG. 9A shows engagement of camming surfaces 1064 of the guard with camming surfaces 308 of the floating trigger member 300 in a pre-firing "ready-to-use" state. FIG. 9B shows engagement of camming surfaces 1064 of guard 106 with camming surfaces 308 of floating trigger member 300 in a triggered or "just-fired" state. As guard 106 is moved in the proximal direction, the axial movement of guard 106 is translated into a rotational movement of floating trigger member 300 via the engagement of camming surfaces 1064 and 308.

Figure 10B:
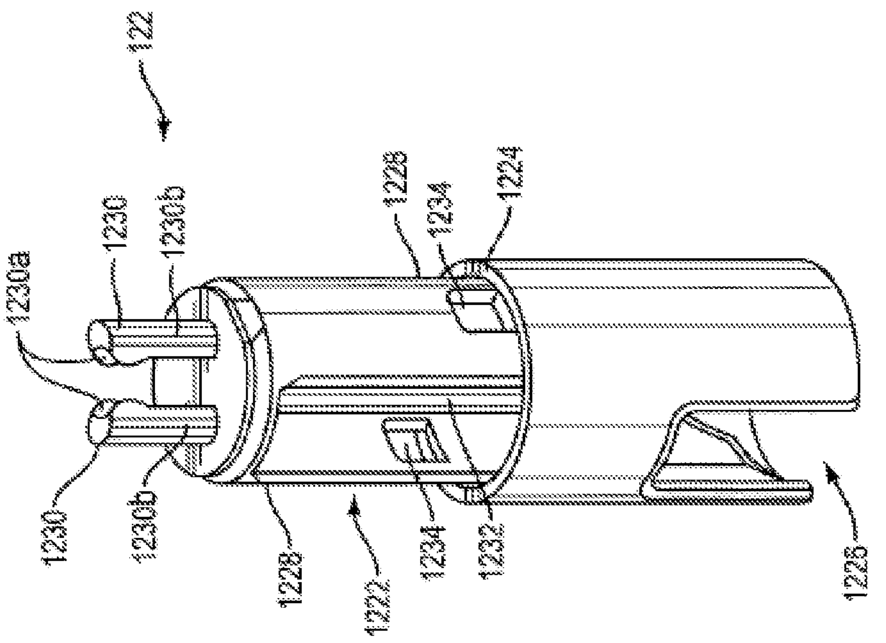
FIGS. 10A and 10B are side and perspective views of a ram assembly of an exemplary injection device according to an exemplary embodiment of the present disclosure.
Figure 10A:
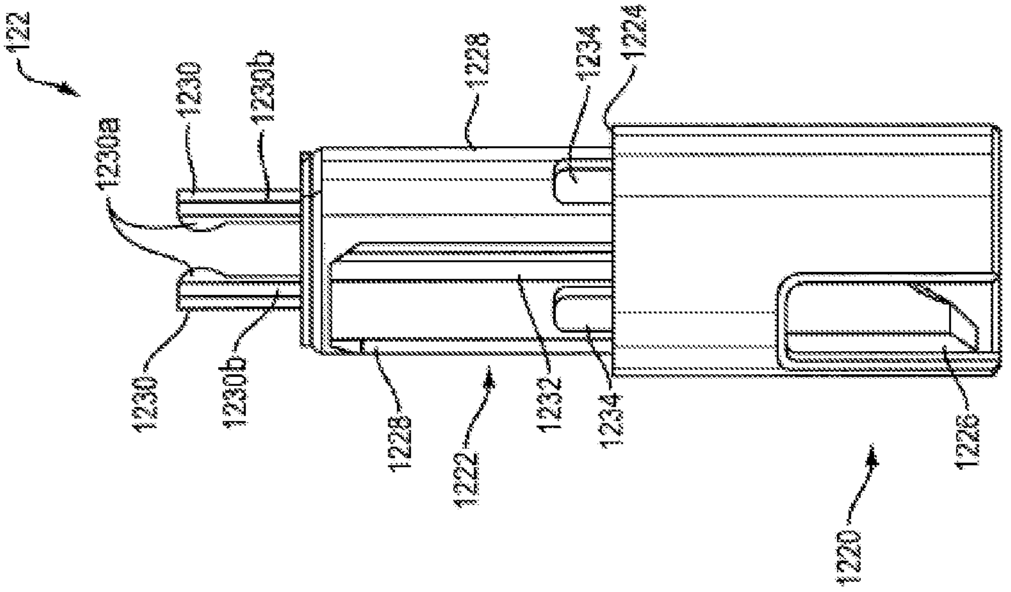

In an exemplary embodiment as shown in FIGS. 10A and 10B, ram assembly 122 containing ram 1232 can include a distal portion 1220 and a proximal portion 1222 separated by a feature 1224, such as a lip, a ledge, that can be configured to act as a seat for energy source 120. As shown in FIG. 13, in an exemplary embodiment, compression spring as energy source 120 can be disposed between a proximal end of housing 102 and feature 1224. As shown in FIG. 4, in an exemplary embodiment, housing 102 includes a feature 102*a*, such as a lip, that is configured to act as a seat for energy source 120. Feature 102*a* can be designed or include elements that reduce friction due to compression spring rotation when energy source 120 is in contact with feature 102*a* in housing 102. Ram assembly 122 including distal portion 1220 can be substantially cylindrical and can be configured to concentrically receive at least a portion of sleeve 116 and guard 106. Distal portion 1220 can also include openings 1226 configured to receive legs 1170 of sleeve 116 and projection 1066 of guard 106.

In one embodiment, proximal portion 1222 includes legs 1228, a ram 1232, and a trigger engagement member 1230. Although trigger engagement member 1230 is shown as projections, alternative implementations are contemplated. Trigger engagement member 1230 can include any feature (e.g., an elongated tab, a thinned tab, a recess, a protrusion, a bulge, a thread, etc.) that can be held by ram retaining member in the pre-firing state, and released upon rotation of the floating trigger member.

As shown in FIGS. 9A and 9B, in one embodiment, camming surface 1064 of guard 106 and camming surface 308 of floating trigger member 300 are oriented at an angle with respect to the longitudinal axis of the device to achieve a selected force and throw required to depress the guard 106 from the extended to the retracted position to fire the device. In some embodiments, the camming surfaces are angled at between 15° and 75° with respect to the axis, and, in one embodiment, between about 20° and 45°. In one embodiment, the camming surfaces are angles at about 30° with respect to the axis.

Figure 11:
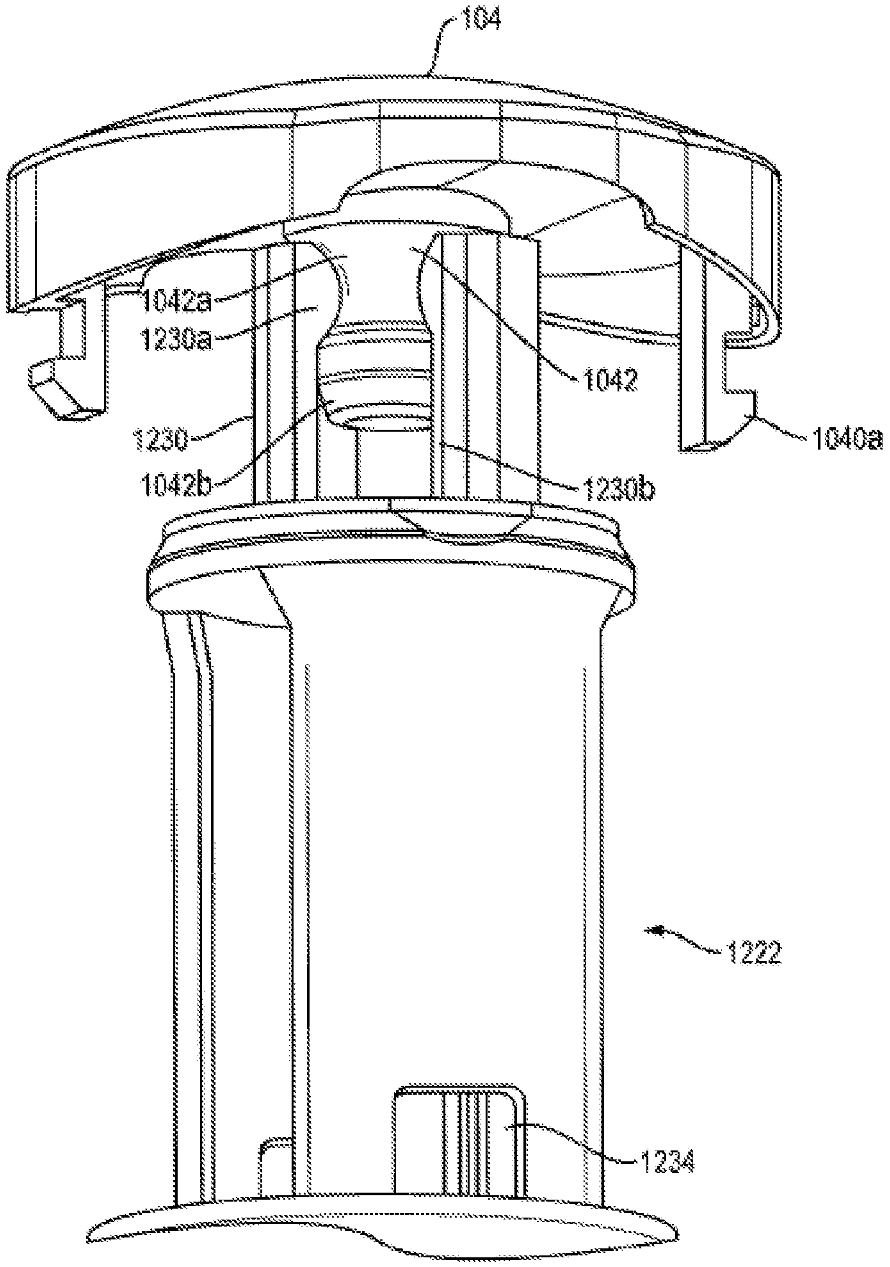
FIG. 11 shows a close-up view of an engagement of a trigger engagement member and a ram retaining member of an exemplary injection device according to an exemplary embodiment of the present disclosure.

As shown in FIGS. 10A and 10B, legs 1228 include openings 1234 configured to engage locking projections 1172 of sleeve 116. It is understood that openings 1234 accommodating alternate specific delivery volumes may be configured on distal portion 1220 to engage locking projections 1172 of sleeve 116. As shown in FIG. 10, for example, locking projections 1172 of sleeve 116 can engage openings 1234 of ram assembly 122 after injection device 100 has been fired, locking-out injection device 100 so that a user cannot initiate subsequent retraction of guard 106 exposing needle 112. Ram 1232 is configured to be in association with plunger 118, and distally displace plunger 118 under the force of energy source 120 to dispense the medicament contained in medicament chamber 110 during an injection. Additionally, trigger engagement members 1230 can be disposed at a proximal end of proximal portion 1222 and can be configured to engage opening 302 of floating trigger member 300 and ram holding member 1042 of housing end/end cap 104. The engagement of trigger engagement members 1230 with opening 302 and ram holding member 1042, as well as the alignment of trigger engagement members 1230 within opening 302 can control and enable firing of injection device 100. For example, trigger engagement members 1230 can include bulges 1230*a* configured to engage groove 1042*a* of ram holding member 1042, and shapes 1230*b* configured to engage bulge 1042*b* of ram holding member 1042. As noted above, trigger engagement members 1230 and ram holding member 1042 preferably include circular cross-sections to allow rotation of floating trigger member 300 during firing of injection device 100. FIG. 11 shows a close-up view of an embodiment of the engagement of trigger engagement member 1230 (e.g., projections) with one embodiment of ram holding member 1042.

In certain embodiments, as shown in FIGS. 17A, 17B, 17C, and 17D, the engagement of bulges 1230*a* of trigger engagement members 1230 of ram assembly 122 with ram holding member 1042 of housing end/end cap 104 creates a latch retention angle 172. In one embodiment, latch retention angle 172 is defined by axis 170 and the contact surface of a distal portion of groove 1042*a* of ram holding member 1042 and bulges 1230*a* of ram assembly 122. In certain embodiments, projections 1230 and ram holding member 1042 are sized and shaped to create, when engaged, a latch retention angle 172 of about 10°, about 11°, about 12°, about 13°, about 14°, about 15°, about 16°, about 17°, about 18°, about 19°, about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, about 40°, about 41°, about 42°, about 43°, about 44°, about 45°, about 46°, about 47°, about 48°, about 49°, about 50°, about 51°, about 52°, about 53°, about 54°, about 55°, about 56°, about 57°, about 58°, about 59°, about 60°, about 61°, about 62°, about 63°, about 64°, about 65°, about 66°, about 67°, about 68°, about 69°, about 70°, about 71°, about 72°, about 73°, about 74°, about 75°, about 76°, about 77°, about 78°, about 79°, about 80°, about 81°, about 82°, about 83°, about 84°, about 85°, about 86°, about 87°, about 88°, about 89° or any range determinable from the preceding angles (for example, about 39° to about 41° or about 79° to about 81°).

In certain embodiments, in a pre-fired state, trigger engagement members 1230 are engaged with the wall of the opening of the trigger member (e.g., opening 302 of floating trigger member 300 or opening 1408 of trigger member 1400 (as discussed in more detail below)), bulges 1230*a* of ram assembly 122 and ram holding member 1042 of housing end/end cap 104 are engaged, and energy source 120 is acting on ram assembly 122. In one embodiment, the engagement of bulges 1230*a* and ram holding member 1042 hold ram assembly 122 in place against the distally-directed force being applied to ram assembly 122 by energy source 120. In one embodiment, in a pre-fired state, energy source 120 is applying axial force on ram assembly 122, which causes bulges 1230*a* of projections 1230 of ram assembly 122 to engage bulge 1042*b* of ram holding member 1042. In one embodiment, the engagement of trigger engagement members 1230 of ram assembly 122 with ram holding member 1042 causes a transfer of force from energy source 120 through to ram holding member 1042. In one embodiment, bulges 1230*a* are configured to bias such that exertion of force by bulges 1230*a* on ram holding member 1042 causes trigger engagement members 1230 to splay and exert a radial force on the wall of the opening of trigger member (e.g., opening 302 of floating trigger member 300 or opening 1408 of trigger member 1400). In one embodiment, the exertion of the radial force by trigger engagement members 1230 on the wall of the opening of the trigger member (e.g., opening 302 of floating trigger member 300 or opening 1408 of trigger member 1400) is such that it causes any movement of the trigger member (e.g., floating trigger member 300 or trigger member 1400) to be met with a friction force. In one embodiment, the factors that affect the amount of friction force between the trigger member and trigger engagement members 1230 include the amount of radial force being applied on the wall of the opening of the trigger member by trigger engagement members 1230 and the interaction between the contacting surfaces of the trigger engagement members 1230 and the wall of the opening of the trigger member. In one embodiment, generally, when holding all other variables constant, the greater the amount of radial force being applied on the wall of the opening of the trigger member by trigger engagement member 1230, the greater the frictional force generated by movement of the trigger member. In one embodiment, generally, when holding all other variables constant, the lower the amount of radial force being applied on the wall of the opening of the trigger member by trigger engagement member 1230, the lower the frictional force generated by movement of the trigger member. In one embodiment, to actuate injection device 100, the user must apply a force on the distal end of guard 106, which cause guard 106 to engage the trigger member (e.g., floating trigger member 300 or trigger member 1400) and actuate injection device 100. In one embodiment, the force being applied to the distal end of guard 106 must be sufficient to overcome the friction force caused by the contact between the trigger member and the trigger engagement members 1230.

The embodiments of designs where main spring force, in its compressed pre-fired state, acts on the restraining components in such a manner where the force of the compressed main spring is more axial than radial with the result of a potentially lower triggering force. This is especially important where the compressed forces of the main spring are high spring forces as described. In one embodiment, in a pre-fired state, bulges 1230*a* on trigger engagement member 1230, when engaged with ram holding member 1042, distribute both an axial force and a radial force on ram holding member 1042. However, in one embodiment, bulges 1230*a* are configured to bias the forces toward a radial force directed on ram holding member 1042 by trigger engagement member 1230 to cause trigger engagement members 1230 to splay outward and engage the wall of opening of trigger member (e.g., opening 302 of floating trigger member 300 or opening 1408 of trigger member 1400). In one embodiment, latch retention angle 172 determines the amount of axial force and radial force that is translated to the ram holding member 1042. In one embodiment, as latch retention angle 172 increases, less radial force is exerted on ram holding member 1042 by trigger engagement member 1230 and, thus, the frictional force resulting from the splaying of ram engagement members 1230 is decreased. In one embodiment, as the force acting to cause the splaying of trigger engagement member 1230 is decreased, less force is exerted on the wall of the opening of trigger member (e.g., opening 302 of floating trigger member 300 or opening 1408 of trigger member 1400) and, thereby, less force is required to actuate injection device 100 than in an embodiment having a larger latch retention angle 172. In one embodiment, where energy source 120 is a high force spring of about 19 lbs. load capacity and latch retention angle 172 is 40°, a user must overcome about 2.5 lbs., about 2.6 lbs., about 2.7 lbs., about 2.8 lbs., about 2.9 lbs. about 3.0 lbs, about 3.1 lbs, about 3.2 lbs. about 3.3 lbs., about 3.4 lbs., about 3.5 lbs., about 3.6 lbs., about 3.7 lbs., about 3.8 lbs., about 3.9 lbs., about 4.0 lbs., about 4.1 lbs., about 4.2 lbs., about 4.3 lbs., about 4.4 lbs., about 4.5 lbs., about 4.6 lbs., about 4.7 lbs., about 4.8 lbs., about 4.9 lbs., about 5.0 lbs., about 5.1 lbs., 5.2 lbs., about 5.3 lbs., about 5.4 lbs., about 5.5 lbs., about 5.6 lbs., about 5.7 lbs., about 5.8 lbs., about 5.9 lbs., about 6.0 lbs., about 6.1 lbs., about 6.2 lbs., about 6.3 lbs., about 6.4 lbs., about 6.5 lbs., about 6.6 lbs., about 6.7 lbs., about 6.8 lbs., about 6.9 lbs., about 7.0 lbs., about 7.1 lbs., about 7.2 lbs., about 7.3 lbs., about 7.4 lbs., about 7.5 lbs., about 7.6 lbs., about 7.7 lbs., about 7.8 lbs., about 7.9 lbs., about 8.0 lbs., about 8.1 lbs., about 8.2 lbs., about 8.3 lbs., about 8.4 lbs., about 8.5 lbs., about 8.6 lbs., about 8.7 lbs., about 8.8 lbs., about 8.9 lbs., about 9.0 lbs., about 9.1 lbs., about 9.2 lbs., about 9.3 lbs., about 9.4 lbs., about 9.5 lbs., about 9.6 lbs., about 9.7 lbs., about 9.8 lbs., about 9.9 lbs., about 10.0 lbs. or any range determinable from the preceding pounds (for example, about 2.5 lbs. to about 3.5 lbs. or about 3.4 lbs. to about 8.7 lbs.) of friction force to actuate injection device 100. In another embodiment, where energy source 120 is a high force spring with 18 lbs. load capacity and latch retention angle 172 is 80°, a user will need only overcome about 0.25 lbs, about 0.30 lbs, about 0.35 lbs, about 0.40 lbs, about 0.45 lbs, about 0.50 lbs, about 0.55 lbs, about 0.60 lbs, about 0.65 lbs, about 0.70 lbs, about 0.75 lbs, about 0.80 lbs, about 0.85 lbs, about 0.90 lbs, about 0.95 lbs, about 1.00 lbs, about 1.05 lbs, about 1.10 lbs, about 1.15 lbs, about 1.20 lbs, about 1.25 lbs, about 1.30 lbs, about 1.35 lbs, about 1.40 lbs, about 1.45 lbs, about 1.50 lbs, about 1.55 lbs, about 1.60 lbs, about 1.65 lbs, about 1.70 lbs, about 1.75 lbs, about 1.80 lbs, about 1.85 lbs, about 1.90 lbs, about 1.95 lbs, about 2.00 lbs, about 2.05 lbs, about 2.10 lbs, about 2.15 lbs, about 2.20 lbs, about 2.25 lbs, about 2.30 lbs, about 2.35 lbs, about 2.40 lbs, about 2.45 lbs, about 2.50 lbs, about 2.55 lbs, about 2.60 lbs, about 2.65 lbs, about 2.70 lbs, about 2.75 lbs, about 2.80 lbs, about 2.85 lbs, about 2.90 lbs, about 2.95 lbs, about 3.00 lbs, about 3.05 lbs, about 3.10 lbs, about 3.15 lbs, about 3.20 lbs, about 3.25 lbs, about 3.30 lbs, about 3.35 lbs, about 3.40 lbs, about 3.45 lbs, about 3.50 lbs, about 3.55 lbs, about 3.60 lbs, about 3.65 lbs, about 3.70 lbs, about 3.75 lbs, about 3.80 lbs, about 3.85 lbs, about 3.90 lbs, about 3.95 lbs, about 4.00 lbs, about 4.05 lbs, about 4.10 lbs, about 4.15 lbs, about 4.20 lbs, about 4.25 lbs, about 4.30 lbs, about 4.35 lbs, about 4.40 lbs, about 4.45 lbs, about 4.50 lbs, about 4.55 lbs, about 4.60 lbs, about 4.65 lbs, about 4.70 lbs, about 4.75 lbs, about 4.80 lbs, about 4.85 lbs, about 4.90 lbs, about 4.95 lbs, about 5.00 lbs, or any range determinable from the preceding pounds (for example, about 0.25 lbs. to about 1.15 lbs. or about 2.10 lbs. to about 3.80 lbs.) of friction force to actuate injection device 100.

Table 1 shows exemplary force values needed to overcome the friction force to actuate injection device 100 where energy source 120 is a high force spring with 18 lbs. load capacity and the latch retention angle 172 is 80° (Design A) and 40° (Design B).

TABLE 1

| Test | Trigger Force Design A (in lbs) | Trigger Force Design B (in lbs) |
|---|---|---|
| 1 | 1.01 | 3.50 |
| 2 | 0.95 | 3.80 |
| 3 | 1.00 | 2.90 |
| 4 | 0.96 | 4.00 |
| 5 | 1.07 | 3.20 |
| Average | 1.00 | 3.48 |

In certain embodiments, a user will need to overcome both the friction force and the force resiliently biasing guard 106 toward the extended position via spring 114 to actuate injection device 100.

In certain embodiments, energy source 120 is configured to generate sufficient force to cause disengagement of bulges 1230*a* and trigger engagement member 1230 when trigger engagement members 1230 are no longer engaged with the wall of the opening of the trigger member (e.g., opening 302 of floating trigger member 300 or opening 1408 of trigger member 1400). In one embodiment, the minimum axial force needed to cause disengagement of bulges 1230*a* and trigger engagement member 1230 when trigger engagement members 1230 are no longer engaged with the wall of the opening of the trigger member (e.g., opening 302 of floating trigger member 300 or opening 1408 of trigger member 1400) is about 0.5 lbs., about 1.0 lbs., about 1.5 lbs., about 2.0 lbs., about 2.5 lbs., about 3.0 lbs., about 3.5 lbs., about 4.0 lbs., about 4.5 lbs., about 5.0 lbs., about 5.5 lbs., about 6.0 lbs., about 6.5 lbs., about 7.0 lbs., about 7.5 lbs., about 8.0 lbs., about 8.5 lbs., about 9.0 lbs., about 9.5 lbs., about 10.0 lbs., about 10.5 lbs., about 11.0 lbs., about 11.5 lbs., about 12.0 lbs., about 12.5 lbs., about 13.0 lbs., about 13.5 lbs., about 14.0 lbs., about 14.5 lbs., about 15.0 lbs., about 15.5 lbs., about 16.0 lbs., about 16.5 lbs., about 17.0 lbs., about 17.5 lbs., about 18.0 lbs., or any range determinable from the preceding loads (for example, about 2.5 lbs. to about 3.5 lbs. or about 8.5 lbs. to about 9.5 lbs.). In other embodiments, the minimum axial force needed to cause disengagement of bulges 1230*a* and trigger engagement member 1230 when members 1230 are no longer engaged with the wall of the opening of the trigger member (e.g., opening 302 of floating trigger member 300 or opening 1408 of trigger member 1400) is about 10%, about 15%, about 20%, about 25%, about 30%, about 35%, about 40%, about 45%, about 50%, about 55%, about 60%, about 65%, about 70% or any range determinable from the preceding percentages (for example, about 15% to about 20% or about 45% to about 55%) of the force generated by energy source 120 acting on ram assembly 122.

Figure 18:
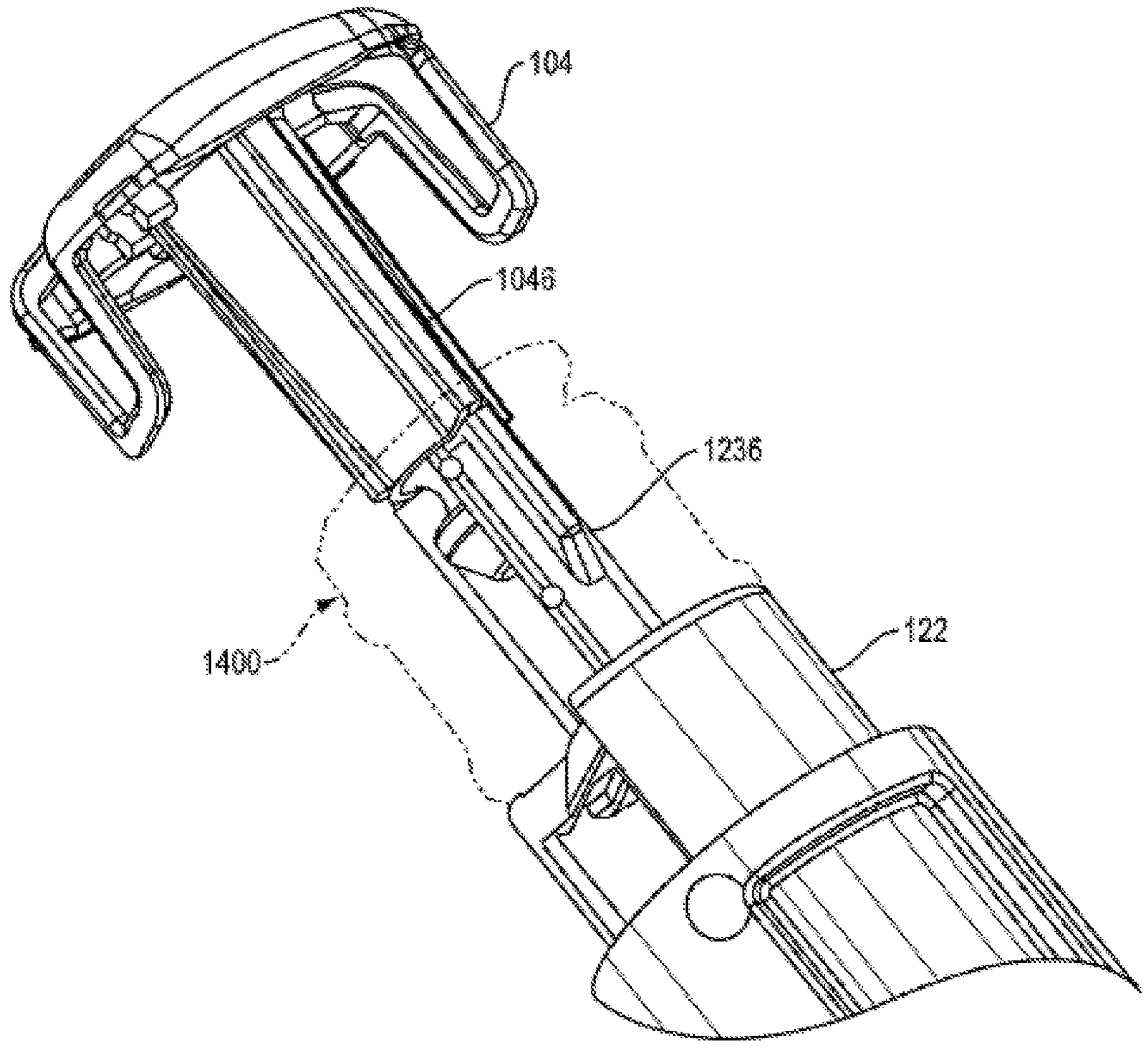
FIG. 18 shows a close-up view of an engagement of a trigger engagement member and a ram retaining member of an exemplary injection device according to an exemplary embodiment of the present disclosure.

In one embodiment, injection device 100 includes an anti-rotational mechanism that prevents ram assembly 122 from rotating relative to housing end/end cap 104. In one embodiment, the anti-rotational mechanism controls alignment of housing end/end cap 104 and ram assembly 122. In certain embodiments, improper alignment of housing end/end cap 104 and ram assembly 122 will prevent the disengagement of ram assembly 122 from housing end/end cap 104 or cause incomplete drug delivery. In one embodiment, as shown in FIG. 18, housing end/end cap 104 includes one or more anti-rotational ribs 1046. In other embodiments, ram assembly 122 has one or more anti-rotational ribs 1236. In one embodiment, in a pre-triggered, anti-rotational ribs 1046 of housing end/end cap 104 align with anti-rotational ribs 1236 of ram assembly 122 within a groove 1412 of trigger member 1400 such that ram assembly 122 is prevented from rotating relative to housing end/end cap 104.

In an exemplary embodiment, injection device 100 can be in a pre-firing "safeties-on" configuration. For example, in the pre-firing "safeties-on" configuration, injection device 100 is in a pre-firing state and cap 200 is affixed to injection device 100. In this configuration, guard 106 is in the extended position under force of spring 114 covering needle 112, ram assembly 122 is in its proximal position, and energy source 120 has not released its energy. Further, in this state, trigger engagement members 1230 of ram assembly 122 are engaged with opening 302 of floating trigger member 300 and aligned in the first position 302*a* (e.g., pre-firing condition) of opening 302. Further, trigger engagement members 1230 are also engaged with ram holding member 1042 of housing end/end cap 104. In this position, trigger engagement member 1230 with ram holding member 1042 of housing end/end cap 104 oppose the force of energy source 120. Further, with trigger engagement members 1230 aligned within the first position 302*a* of opening 302, retaining portion 306 of opening 302 prevents trigger engagement members 1230 from splaying open and disengaging ram holding member 1042 under the force of energy source 120.

In an exemplary embodiment, injection device 100 can be in a pre-firing "ready-to-use" state. For example, in a pre-firing "ready-to-use" configuration, cap 200 has been removed, but the user has not otherwise initiated an injection. Accordingly, in this state, the medicament is still in medicament chamber 110, guard 106 remains in an extended position covering needle 112, energy source 120 has not released the energy that it has stored, and trigger engagement member 1230 of ram assembly 122 remain engaged with ram holding member 1042 and aligned in the first position (302*a*) of opening 302 of floating trigger member.

In an exemplary embodiment, injection device 100 can be in a triggered or "just-fired" state. For example, in a triggered or "just-fired" state, guard 106 has been proximally slidably displaced (e.g., by application of a force on the distal end of guard 106) from the extended position to the retracted position, thereby exposing needle 112. Energy source 120 is just beginning to release its stored energy (e.g., the exemplary compression spring remains compressed), and ram assembly 122 remains in the proximal-most position. Injection device 100 may be in this state, for example, during an initial stage of use by a user. For example, this can be observed when the user has pressed guard 106 of injection device 100 against an injection site to perform an injection. Accordingly, the force exerted by the user in pressing guard 106 of injection device 100 against the injection site may have proximally displaced guard 106 against the force of spring 114, thereby displacing guard 106 into the retracted position and exposing needle 112 to penetrate the user's skin at the injection site.

In on embodiment, in this triggered state, guard 106 has been displaced into the retracted position, camming surfaces 1064 of guard 106 engage camming surfaces 308 of floating trigger member 300, thereby camming floating trigger member 300. This camming action rotates floating trigger member 300, causing trigger engagement members 1230 to become unaligned with the first position of opening 302 and become aligned with the second position of opening 302. In this position, trigger engagement members 1230 are no longer restrained from splaying open by retaining portion 306 of opening 302. Accordingly, trigger engagement members 1230 splay open under the force of, energy source 120, causing bulges 1230*a* to disengage with ram holding member 1042 of housing end/end cap 104. The disengagement of bulges 1230*a* with ram holding member 1042 allows ram assembly 122 to be distally slidably displaced relative to housing 102 under the force generated by energy source 120. In one embodiment, the distal displacement of ram assembly 120 is restrained by ram assembly 120 abutting a proximal surface of ring-like structure 1160 of sleeve 116.

In an exemplary embodiment, injection device 100 can be in a "just-injected" state. This state follows the disengagement of bulges 1230*a* with ram holding member 1042 and the distal displacement of ram assembly 122 described above. In this state, energy source 120 (e.g., a compression spring) has released its energy, thereby distally displacing ram assembly 122. Further, guard 106 remains compressed in the retracted position. This state may be observed during use of injection device 100 immediately following the trigger or "just-used" state. As described above, camming of floating trigger member 300 aligns projections 1230 with the second position defined by opening 302, allowing trigger engagement members 1230 to splay open and disengage ram holding member 1042 under the force released by energy source 120. Accordingly, energy source 120 has released at least some, if not all, of its stored energy (e.g., compression spring is less compressed), and ram assembly 122, as well as ram 1232, has been distally displaced into a distal position. The distal displacement of ram 1232 urges plunger 118 in a distal direction, injecting the medicament into the user by dispensing the medicament in medicament chamber 110 through needle 112 and into the user. Although the injection has, in certain embodiments, been completed in this state, injection device 100 is still likely pressed against the injection site since guard 106 remains in a retracted position exposing needle 112. Further, in certain embodiments, this distal displacement of ram assembly 122 positions ram assembly 122 such that it is displayed in a window of housing 102. In an exemplary embodiment, after the distal displacement of ram assembly 122, it is disposed between medicament container 110 and housing 102 such that it is entirely occluding the window so that only ram assembly 122 is visible through the window, and medicament container 110 is no longer visible (e.g., ram assembly is disposed between medicament container 110 and the window). Further, ram assembly 122 can have a color (as described above) that would be a clear indicator to a user that injection device 100 has been used, and different than the other colors visible from the outside of the injector before firing.

In an exemplary embodiment, injection device can be in a "locked-out" state. For example, the "locked-out" state can be observed after the user has removed injection device 100 from the injection site. In this state, nothing is restraining guard 106 in the retracted position against the force of spring 114, and accordingly, guard 106 is distally displaced from the retracted position to the extended position under the force of spring 114, thereby covering needle 112. As guard 106 moves distally from the retracted position to the extended position under the force of spring 114, projections 1066, which are disposed on springs 1068 biased in an outward direction, engage the openings created between proximal surfaces of legs 1170 of sleeve 116 and proximal walls of openings 1226. Accordingly, the association of projections 1066 with the proximal walls of openings 1226 prevents guard 106 from being displaced proximally, and the association of projections 1066 with the proximal surfaces of legs 1170 prevents guard 106 from being displaced distally. Thus, guard 106 is in a locked position, thereby locking-out injection device 100 such that needle 112 is covered and guard 106 is locked in place so that a user cannot attempt a subsequent injection. Afterwards, the user may affix cap 200 back onto the distal end of injection device 100.

Advantageously, in one embodiment, this "locked-out" state is not dependent on displacement of guard 106, but rather, is dependent on dispensing of the medicament stored in medicament chamber 110 and/or movement of ram assembly 122. For example, injection device 100 becomes locked-out in situations where the medicament is inadvertently dispensed, even if guard 106 has not been displaced. Injection device 100 can become locked-out in any instance where energy source 120 is activated and ram assembly 122 is distally displaced, causing ram 1232 to displace plunger 118, thereby dispensing the medicament in medicament chamber 110.

Figure 12:
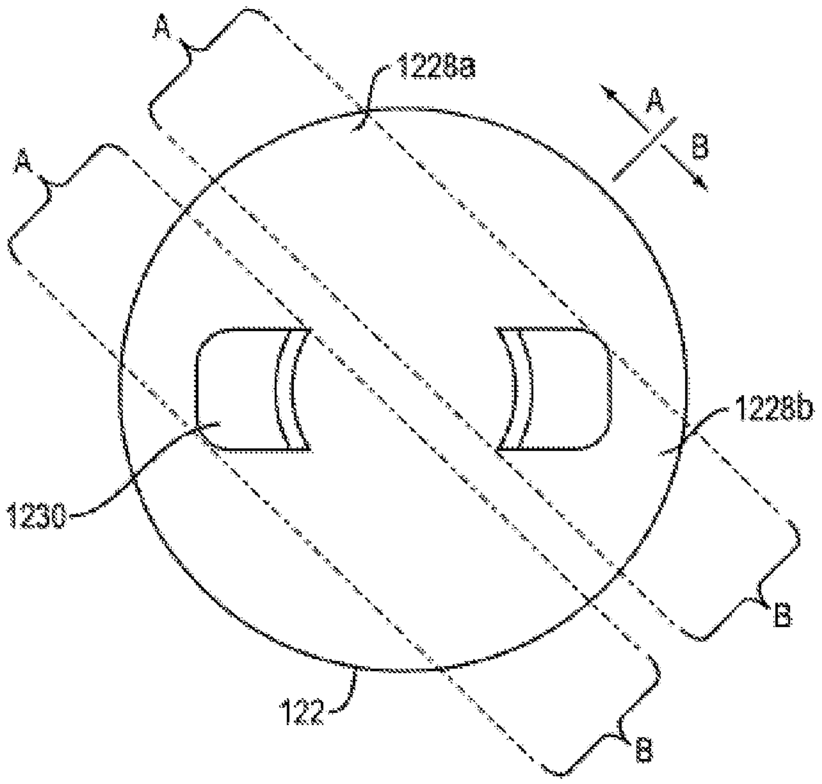
FIG. 12 shows a top view of a ram assembly of an exemplary injection device according to an exemplary embodiment of the present disclosure.

In an exemplary embodiment, many of the components of injection device 100 are made of a resilient plastic or polymer, or a metal. In one embodiment, projections 1230 of ram assembly 122 are oriented so that ram assembly 122 can be molded using a single mold. For example, as shown in FIG. 10, projections 1230 (which are in certain embodiments concentrically symmetrical to each other) can be aligned at an angle relative to the alignment of the other features of ram assembly 122, such as legs 1228 (which are in certain embodiments concentrically symmetrical to each other). For example, as shown in FIG. 12, a single mold can form the portion of ram assembly 120 designated A (including all the features, components, openings, etc. 1228A), and a single mold can form the portion of ram assembly designated B (including all the features, components, openings, etc. 1228B). Thus, in certain embodiments, each surface of projections 1230 is accessible along a direction of separating the two molds, and the two molds can be separated linearly without a concave portion of projections 1230 facing orthogonal to the separation direction impeding separation and removal of the molds.

Further, cap 200 can be configured helically so that it can be molded without a hole/opening. For example, cap 200 can include threads 206 that permit cap 200 to be threadedly removed from a mold. Further, outer housing 102 can include a translucent material to allow users to view the inner workings of injection device 100, and ascertain if it is malfunctioning (e.g., as shown in FIG. 1). Additionally, injection device 100 can include various gripping elements, such as ridges, pads, contours, or the like, to make injection device 100 more ergonomic, easy to use, and comfortable to the user. Further, injection device 100 can include markings, such as a sticker, brand markings, drug information, numerals, arrows, or the like, to indicate the steps needed to perform an injection, and areas for promotional markings such as brand and logo designations.

Figure 14A:
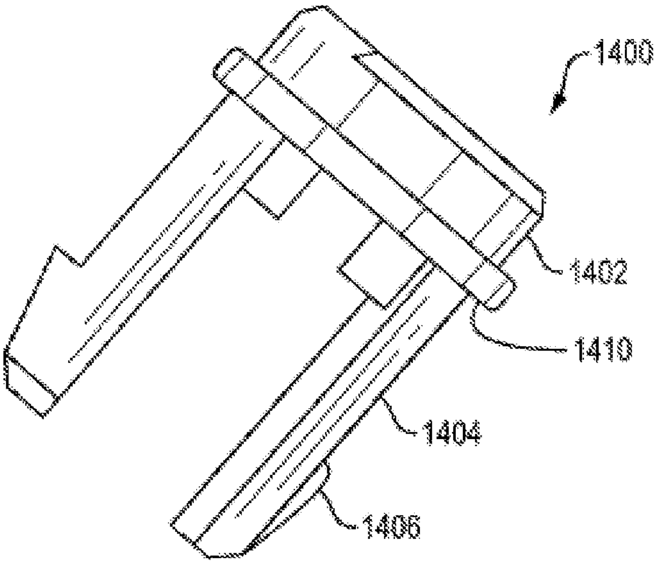
FIG. 14A is a perspective view of a trigger member of an exemplary injection device according to an exemplary embodiment of the present disclosure.
Figure 14B:
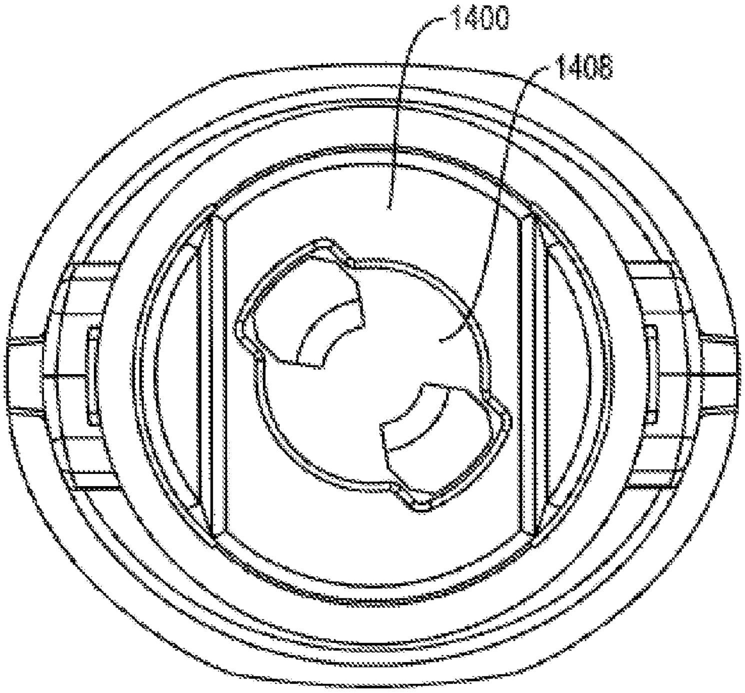
FIG. 14B is a cross-section view of an exemplary injection device according to an exemplary embodiment of the present disclosure.
Figure 14C:
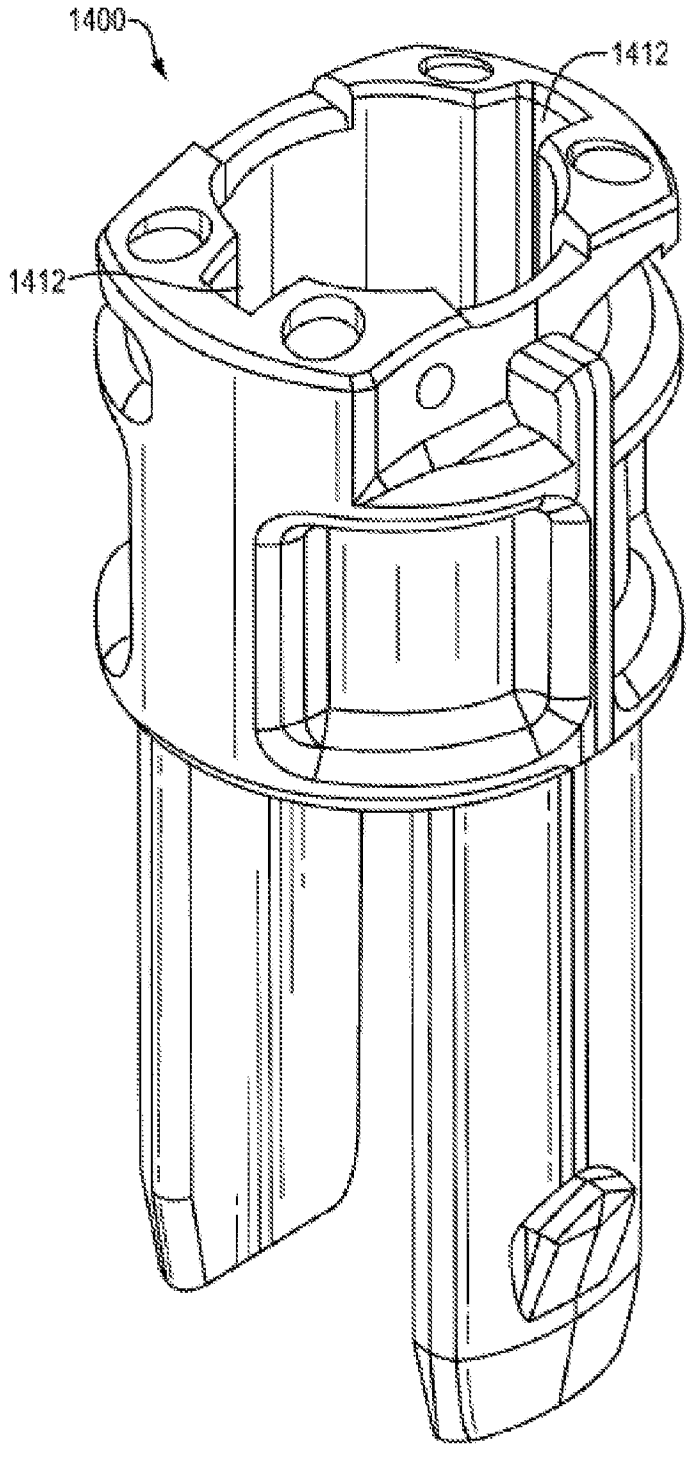
FIG. 14C is a perspective view of a trigger member of an exemplary injection device according to an exemplary embodiment of the present disclosure.
Figure 15B:
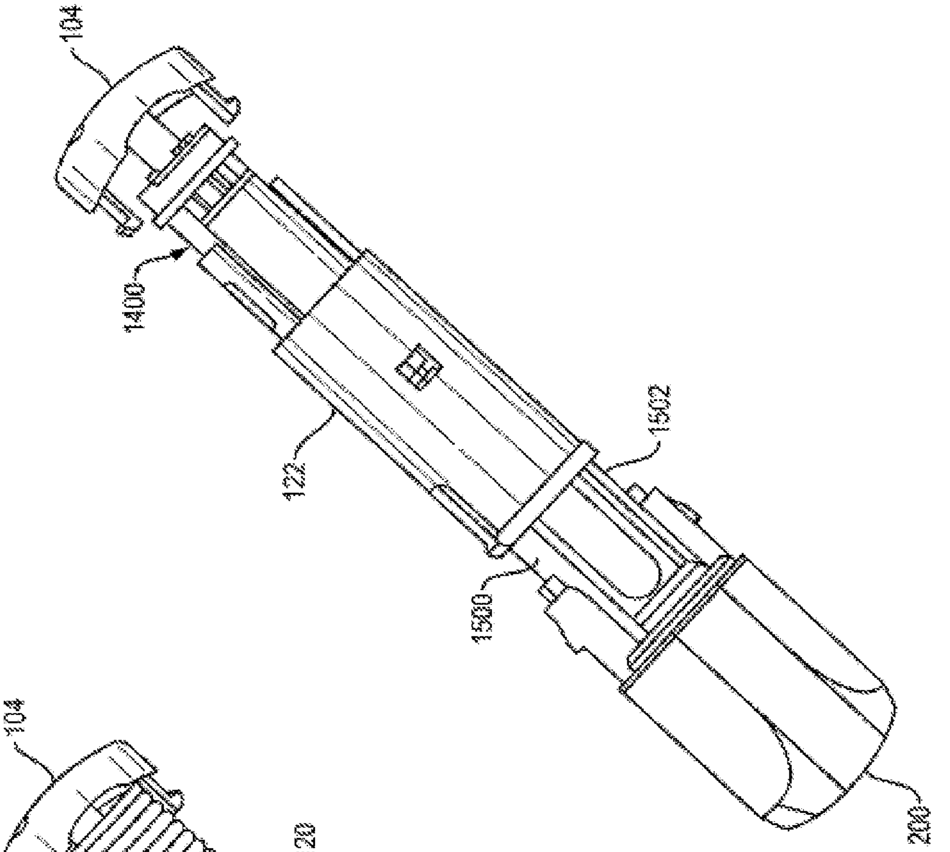
FIGS. 15A and 15B are various side views of a ram assembly, needle guard, housing end/end cap, and trigger member an of an exemplary injection device according to an exemplary embodiment of the present disclosure.
Figure 15A:
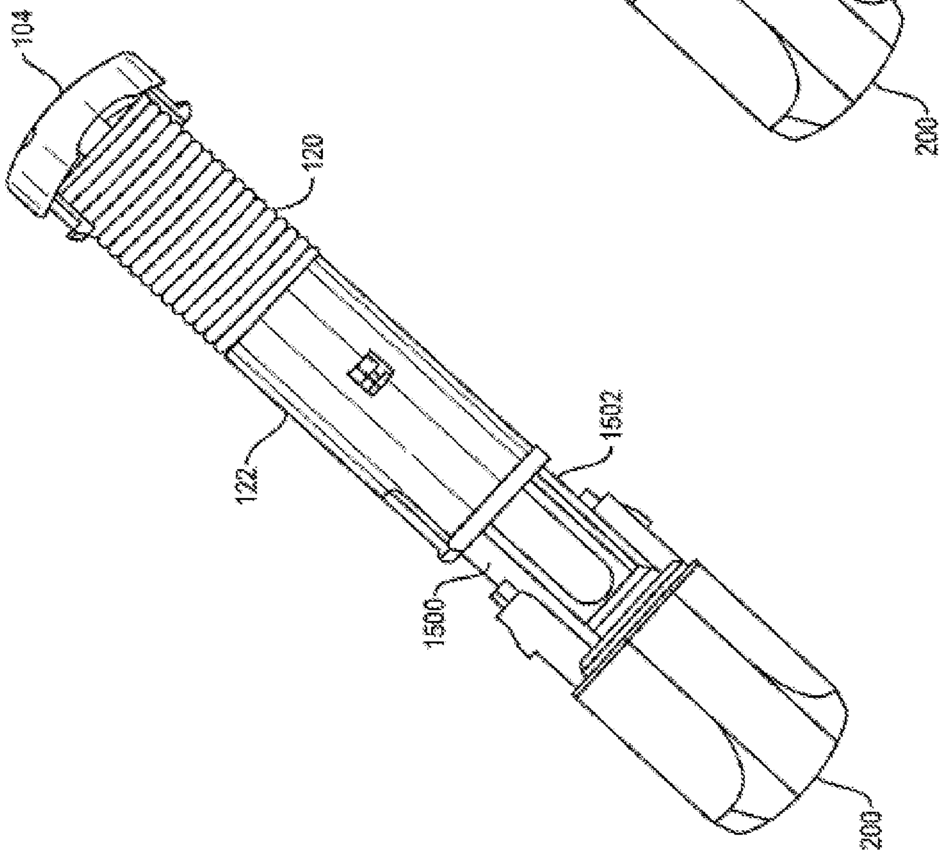
Figure 15D:
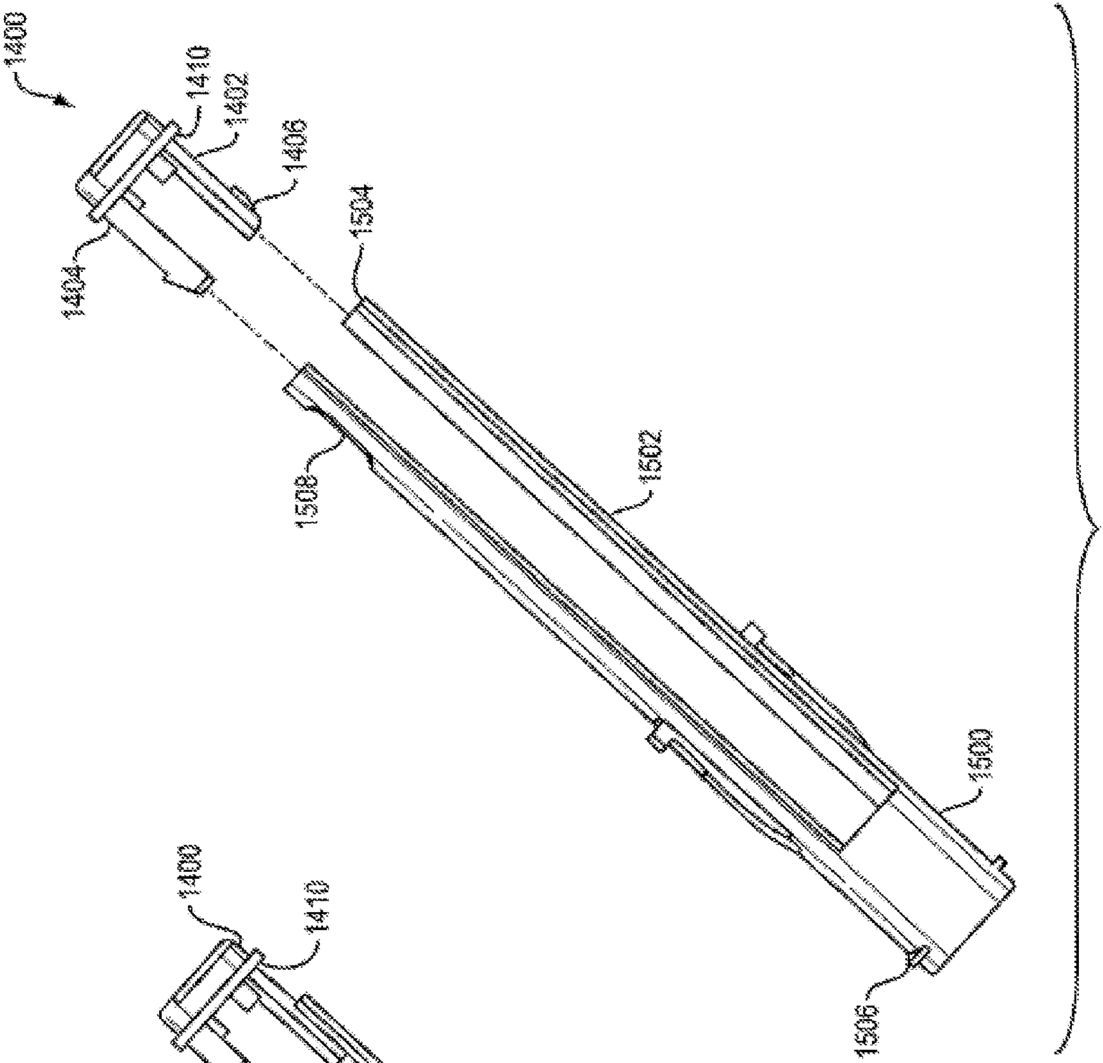
FIGS. 15C and 15D are side views of a trigger member of an exemplary injection device according to an exemplary embodiment of the present disclosure.
Figure 15C:
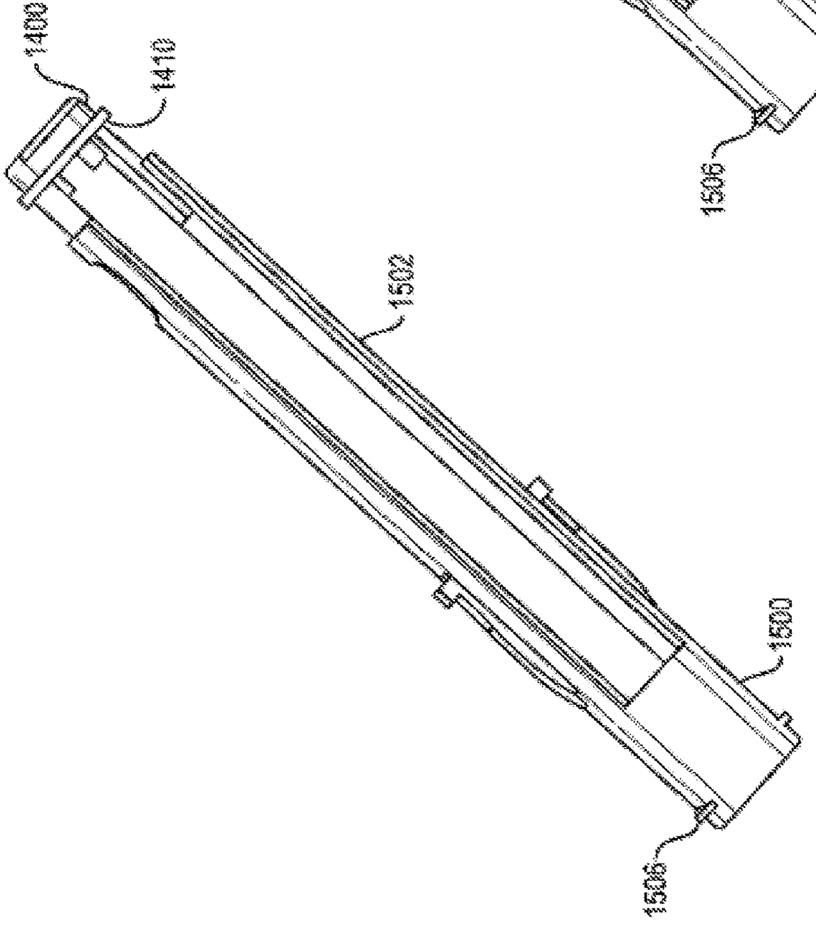
Figure 15F:
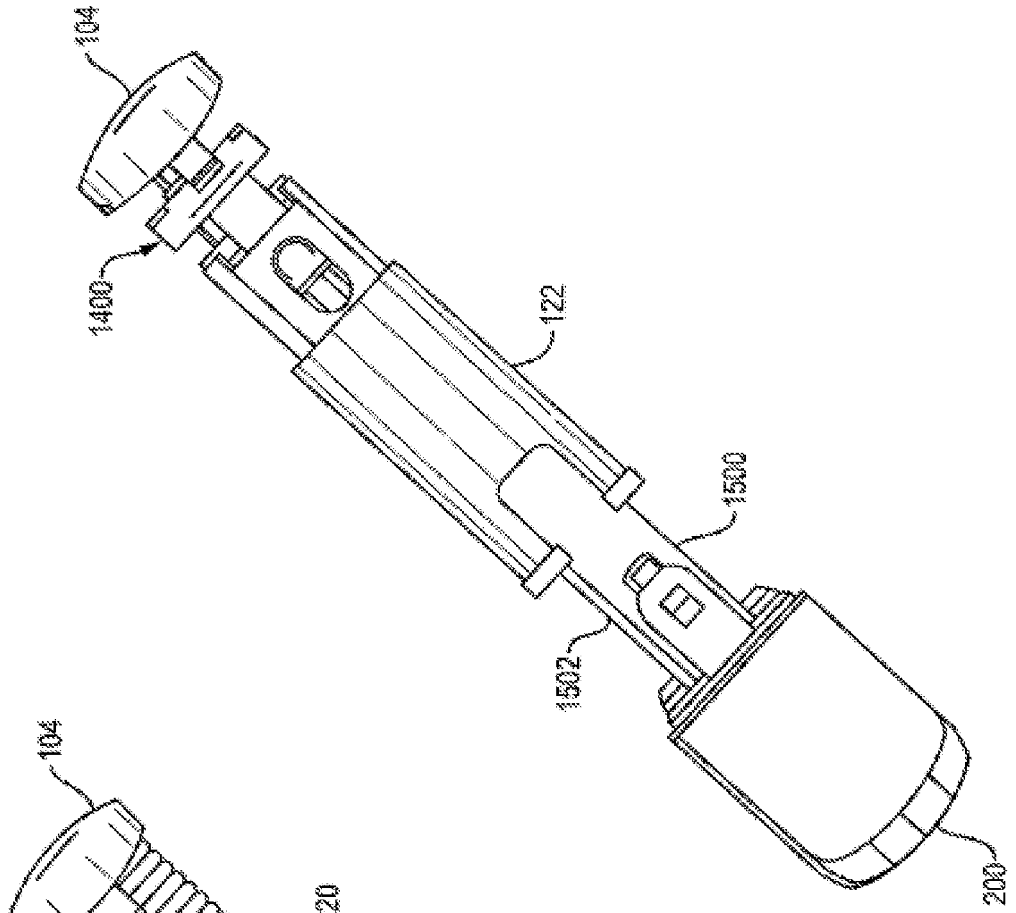
FIGS. 15E and 15F are various side views of a ram assembly, needle guard, housing end/end cap, and trigger member an of an exemplary injection device according to an exemplary embodiment of the present disclosure.
Figure 15E:
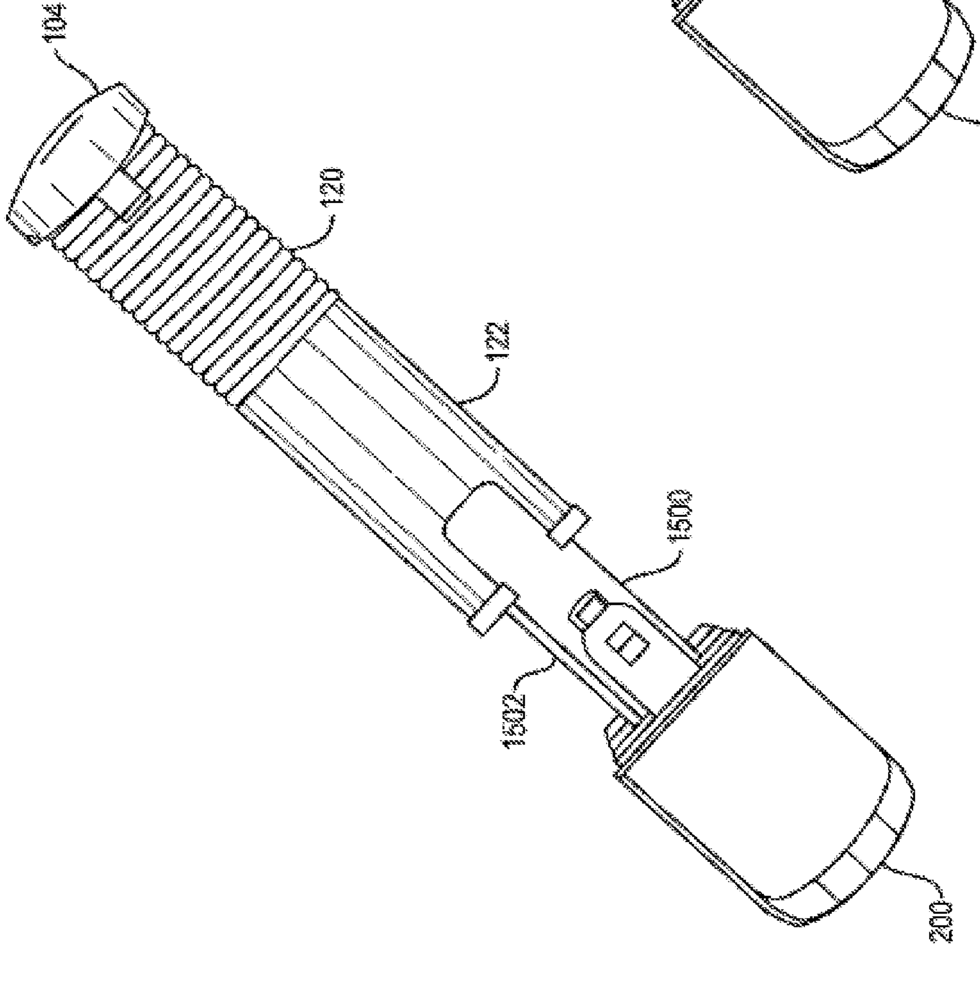
Figures 15G, 15H:
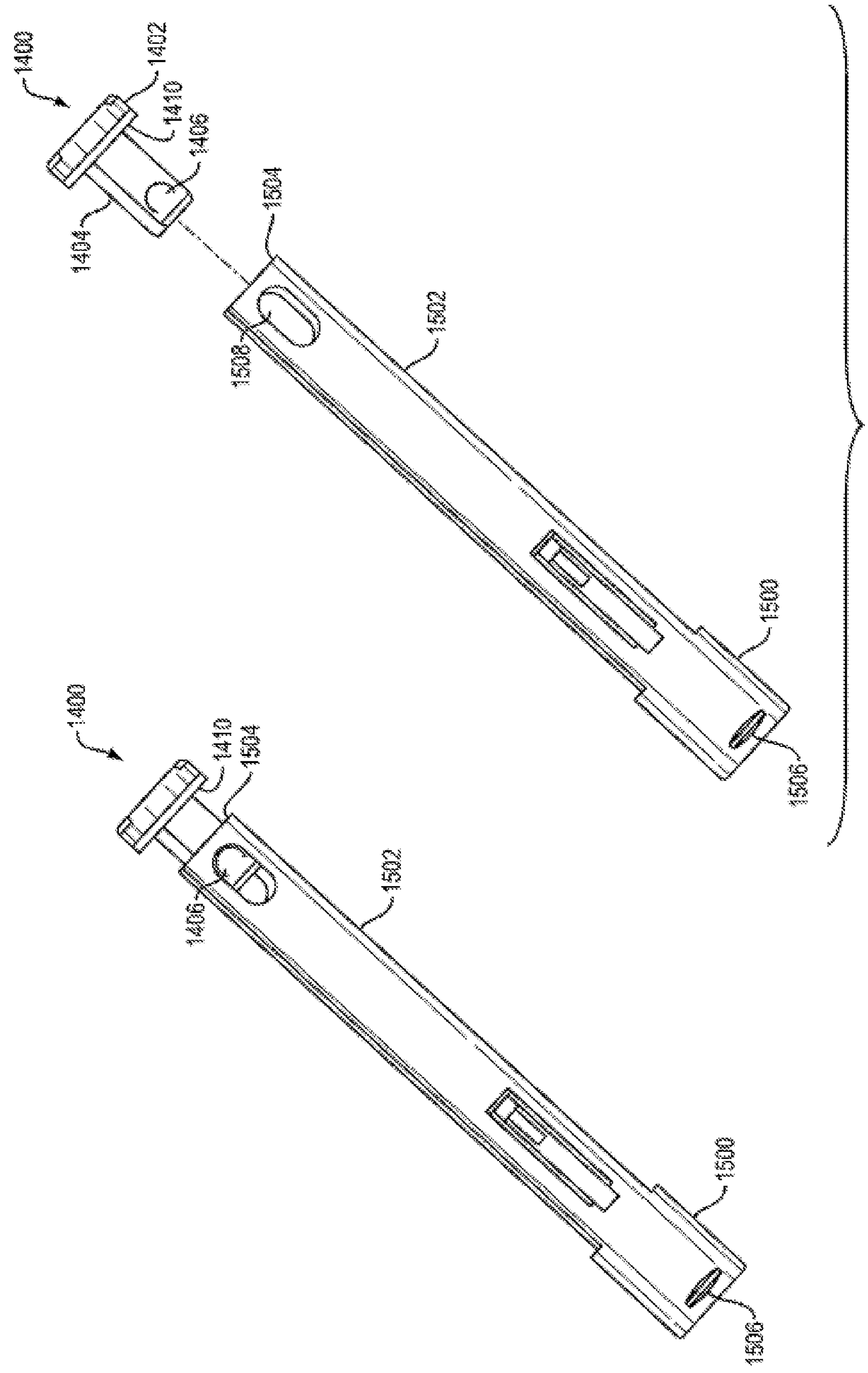
FIGS. 15G and 15H are side views of a trigger member of an exemplary injection device according to an exemplary embodiment of the present disclosure.

While illustrative embodiments of the invention are disclosed herein, it will be appreciated that numerous modifications and other embodiments may be devised by those skilled in the art. For example, the features for the various embodiments can be used in other embodiments. Other embodiments can include different mechanisms to cause the release of ram assembly 122 by actions on the trigger engagement member 1230 and a triggering member. For example, in one embodiment, injection device 100 includes a trigger member 1400, as shown in FIGS. 14A and 14B. In one embodiment, trigger member 1400 has a body 1402 and legs 1404 extending from body 1402. In one embodiment, body 1402 includes lip 1410. In one embodiment, lip 1410 is configured to engage surface 1504 of guard 1500 (described in more detail below and as seen in FIG. 15D). In certain embodiments, legs 1402 have tabs 1406 extending from a distal end of legs 1404. In one embodiment, tabs 1406 are shaped and dimensioned to slidably engage guard 1500. Further, in one embodiment, trigger member 1400 includes an opening 1408 disposed through body 1402. In one embodiment, opening 1408 is configured to engage a trigger engagement member 1230 of firing mechanism 108. In one embodiment, engagement of bulges 1230 a on trigger engagement member 1230 prevent injection device from firing. In one embodiment, trigger member 1400 is configured such that axial movement in a proximal direction causes disengagement of opening 1408 and projections 1230. FIG. 14C shows another embodiment of trigger member 1400. In certain embodiments, trigger member 1400 includes a groove 1412 as part of an anti-rotational mechanism.

Figure 16A:
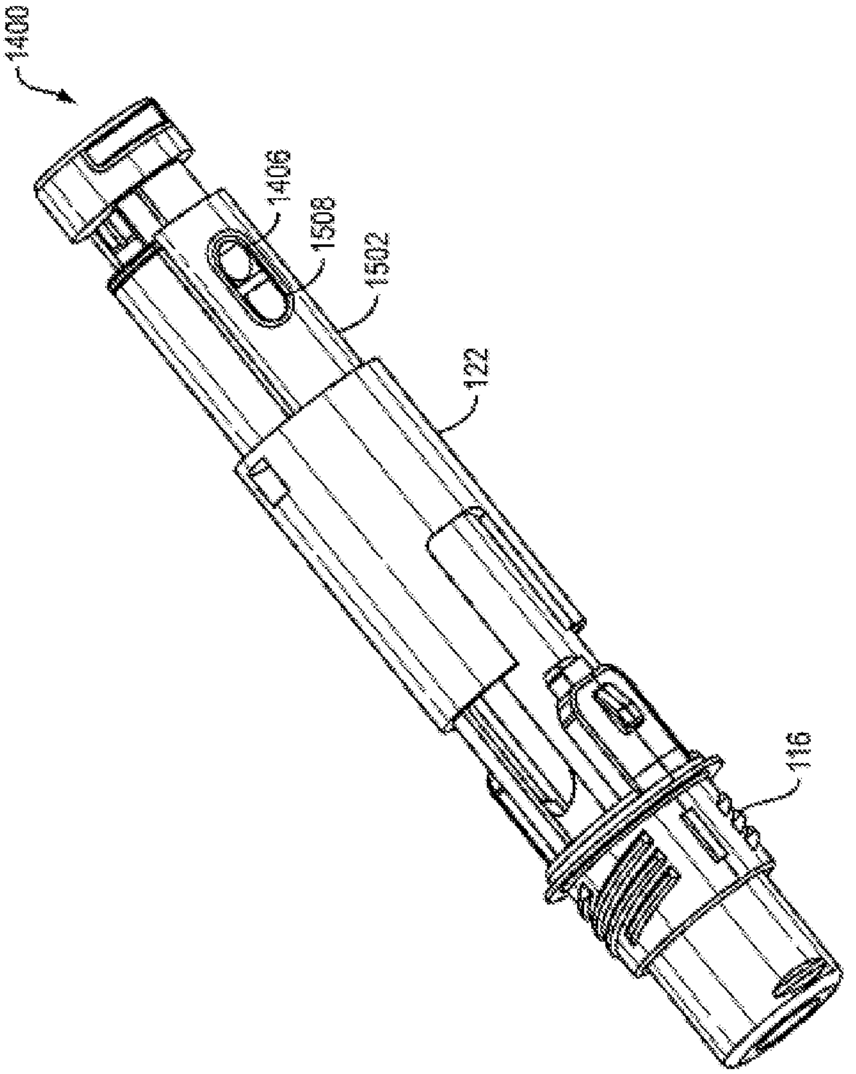
FIGS. 16A, 16B and 16C are various side views of an exemplary injection device according to an exemplary embodiment of the present disclosure in pre-triggered, triggering, and triggered positions, respectively.
Figure 16B:
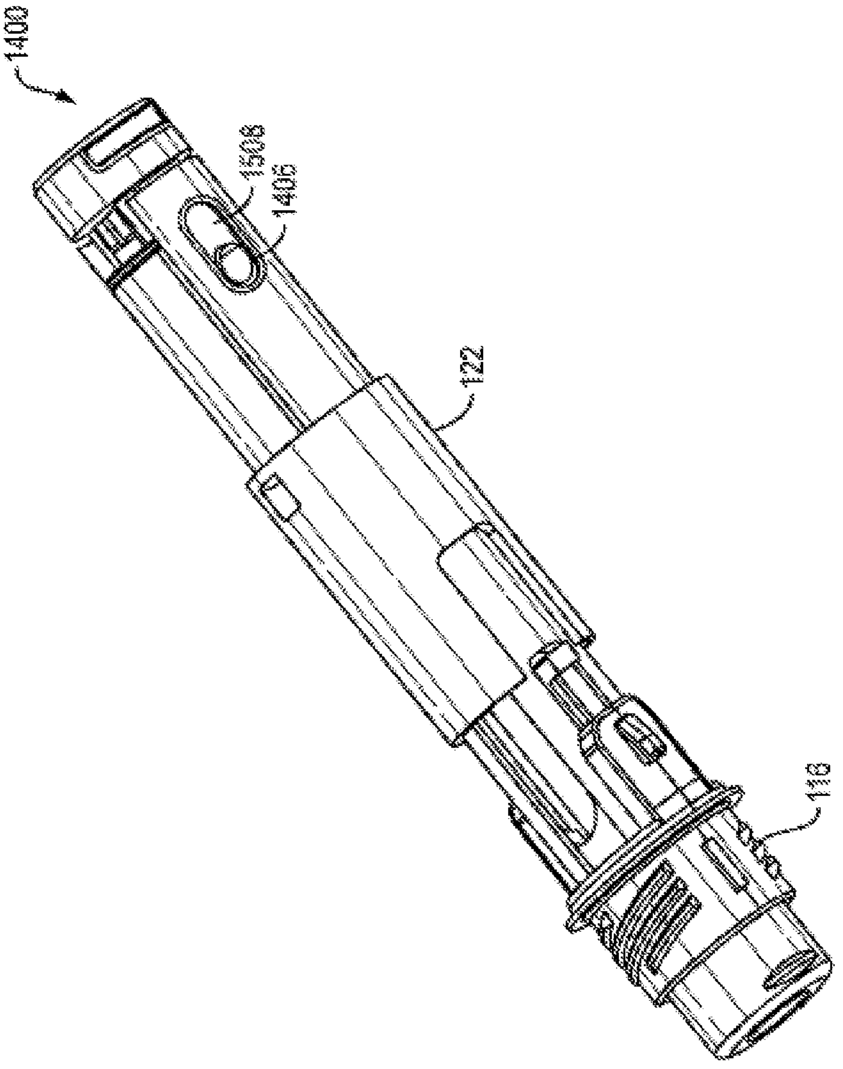
Figure 16C:
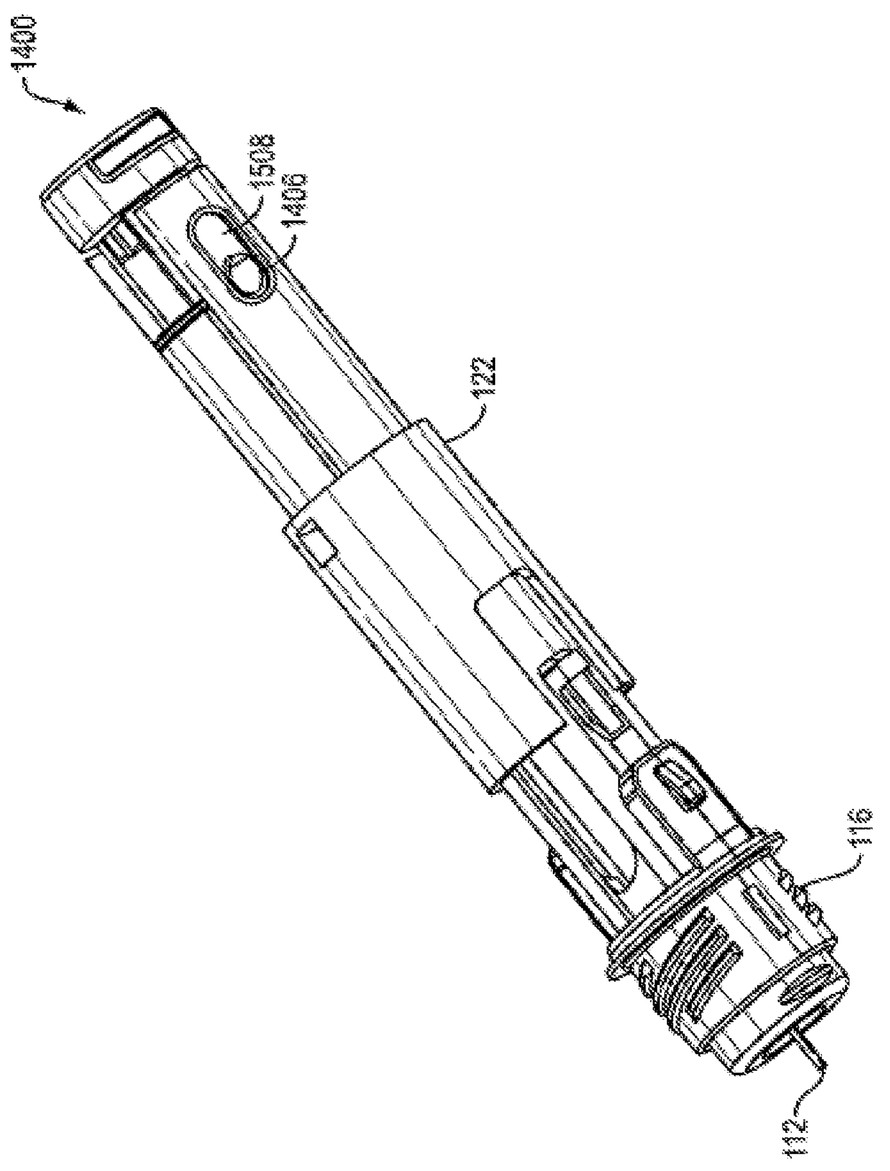
Figure 17B:
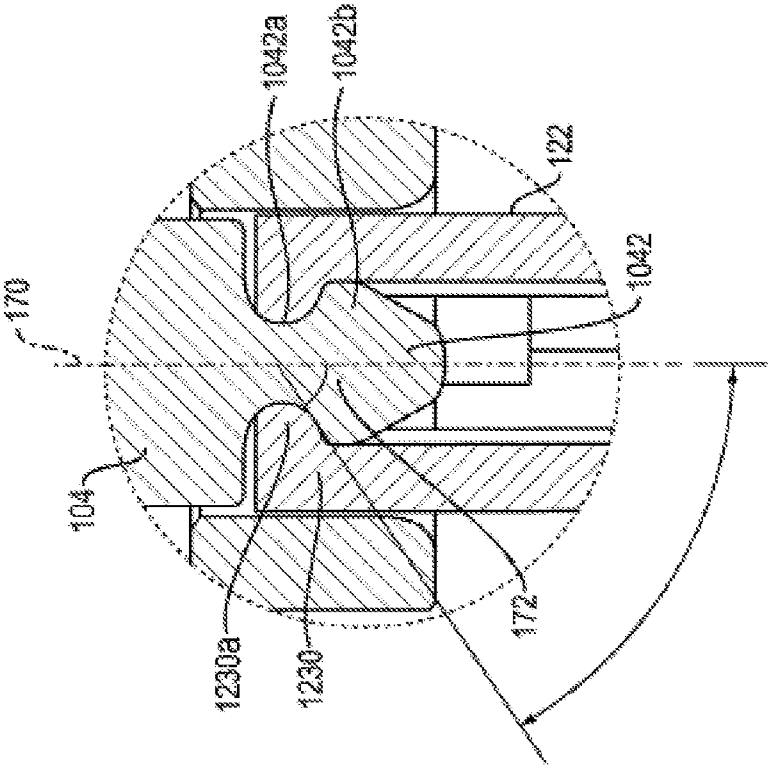
FIG. 17B is a magnified cross-section view of a portion of the end cap, ram assembly and trigger as shown in FIG. 17A.
Figure 17A:
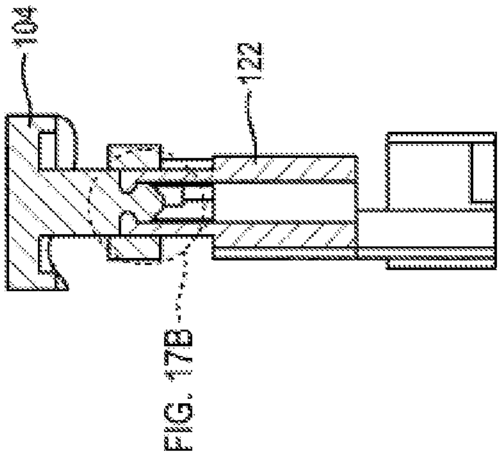
FIG. 17A is a cross-section view of a portion of the end cap, ram assembly and trigger as shown in FIG. 16A.
Figure 17D:
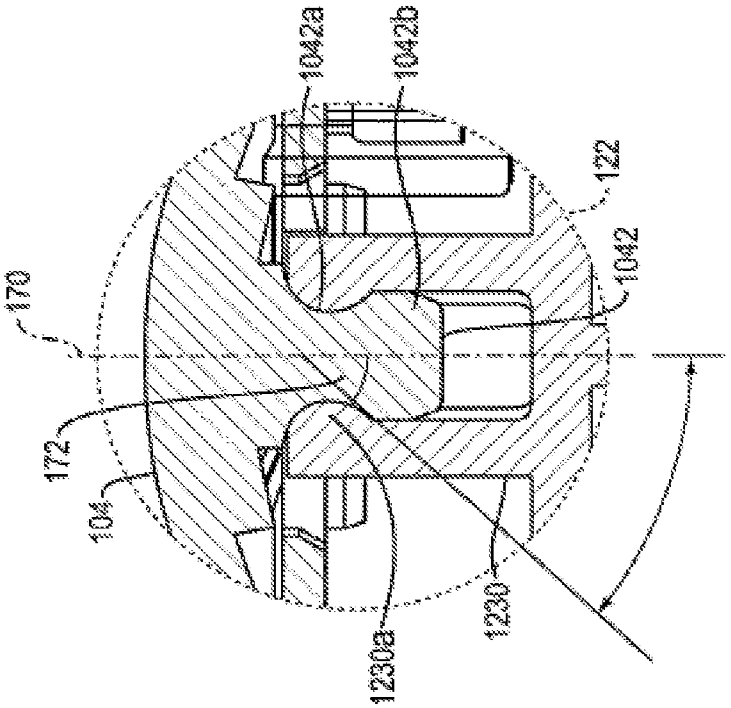
FIG. 17D is a magnified cross-section view of the end cap, ram assembly and trigger of the injection device shown in FIG. 17C.
Figure 17C:
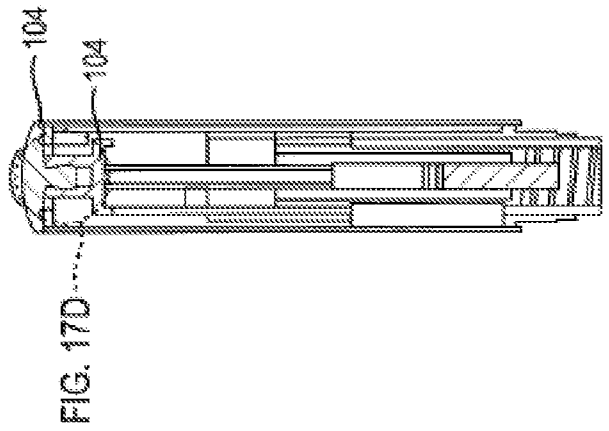
FIG. 17C is a cross-section view of the end cap, ram assembly and trigger of the injection device shown in FIG. 1.

As shown in FIGS. 15A through 15H, in one embodiment, injection device 100 includes a guard 1500. In one embodiment, guard 1500 includes legs 1502. In another embodiment, legs 1502 have firing-initiation members, such as surfaces 1504 at a proximal end of legs 1500. In one embodiment, surfaces 1504 are configured to engage lip 1410 of trigger member 1400. In one embodiment, legs 1502 are configured to be received in openings 1178 of ring-like structure 1160. In one embodiment, legs 1502 include ridges 1506 configured to engage grooves 1164*a* of sleeve 116, to facilitate alignment and guiding of legs 1502 as guard 1500 is axially displaced. In an exemplary embodiment, legs 1502 and surfaces 1504 are concentrically symmetrical. In one embodiment, surfaces 1504 are configured to engage firing mechanism 108 in initiating a firing of injection device 100 and performing an injection of the medicament stored in medicament chamber 110. In one embodiment, surfaces 1504 are shaped to engage lip 1410 of trigger member 1400 when guard 1500 is displaced from the extended position to the retracted position. In one embodiment, legs 1502 include apertures 1508. In one embodiment, apertures 1508 are sized and shaped to engage tabs 1406 of trigger member 1400. In one embodiment, apertures 1508 are sized and shaped to allow tabs 1406 to be slideably engageable with apertures 1508. In one embodiment, as shown in FIGS. 16A and 16B, when apertures 1508 and tabs 1406 are in a slideably engageable configuration, for a predetermine distance, guard 1500 can axially translate without movement of trigger member 300. In another embodiment, as shown in FIGS. 16A, 16B, and 16C, when apertures 1508 and tabs 1406 are in a slideably engageable configuration, after guard 1500 axially translates a predetermine distance without causing movement of trigger member 1400, axial translation of guard 1500 beyond the predetermined distance causes axial translation of trigger member 1400.

In one embodiment, apertures 1508 are sized and shaped to allow tabs 1406 to snap-fit within aperture 1508. In one embodiment, when apertures 1508 and tabs 1406 are in a snap-fit configuration, axial translation of guard 1500 causes direct axial translation of trigger member 1400 such that guard 1500 cannot axially translate without also translating trigger member 1400. In one embodiment, direct axial translation of trigger member 1400 in a proximal direction causes disengagement of opening 1408 of trigger member 1400 and trigger engagement members 1230 of firing mechanism, which causes disengagement of bulges 1230*a* and ram holding member 1042. In one embodiment, disengagement of ram holding member 1042 housing end/end cap 104 and trigger engagement members 1230 causes injections device 100 to fire Although not shown, it is also contemplated that a tab or protrusion can be located on legs 1502 of guard 1500 such that the tab can communicate, either slidingly or directly with an aperture located on trigger member 1400.

Other embodiments can include different mechanisms to cause the release of trigger engagement members 1230 from a trigger member, such as by direct rotation of the floating trigger member 300 by a user, such as via a slide or other element accessible on the outside of the housing, or by a button that is pushed with a finger, or another transmission mechanism to rotate the floating trigger member. Therefore, it will be understood that the appended claims are intended to cover all such modifications and embodiments that come within the spirit and scope of the present invention.

Referring to FIGS. 28-36, in one embodiment, injection device 100 may include safety cap 402. Safety cap 402 may be removably affixable to a distal end of injection device 100. In one embodiment, safety cap 402 is removably affixed to the distal end of injection device 100 via a threaded engagement. In other embodiments, safety cap 402 is removably coupled to injection device 100 via snap fit, interference fit, fastener, or adhesive. Safety cap 402 may be removed from injection device 100 by pulling, pushing, or twisting safety cap 402 relative to injection device 100. When safety cap 402 is affixed to injection device 100, safety cap 402 contributes to ensuring that injection device 100 cannot be inadvertently or accidentally triggered. For example, safety cap 402 may be configured to prevent unintended exposure of needle 406 (e.g., during manufacture, transportation, or prior to an intended use).

In one embodiment, safety cap 402 may include end wall 421 and end wall opening 403. End wall 421 and end wall opening 403 may be configured to allow needle 406 to be placed within safety cap 402. Safety cap 402 may include arms 410. Arms 410 may include an engagement feature configured to engage a rear surface of a needle shield. Arms may be flexible.

Figure 30:
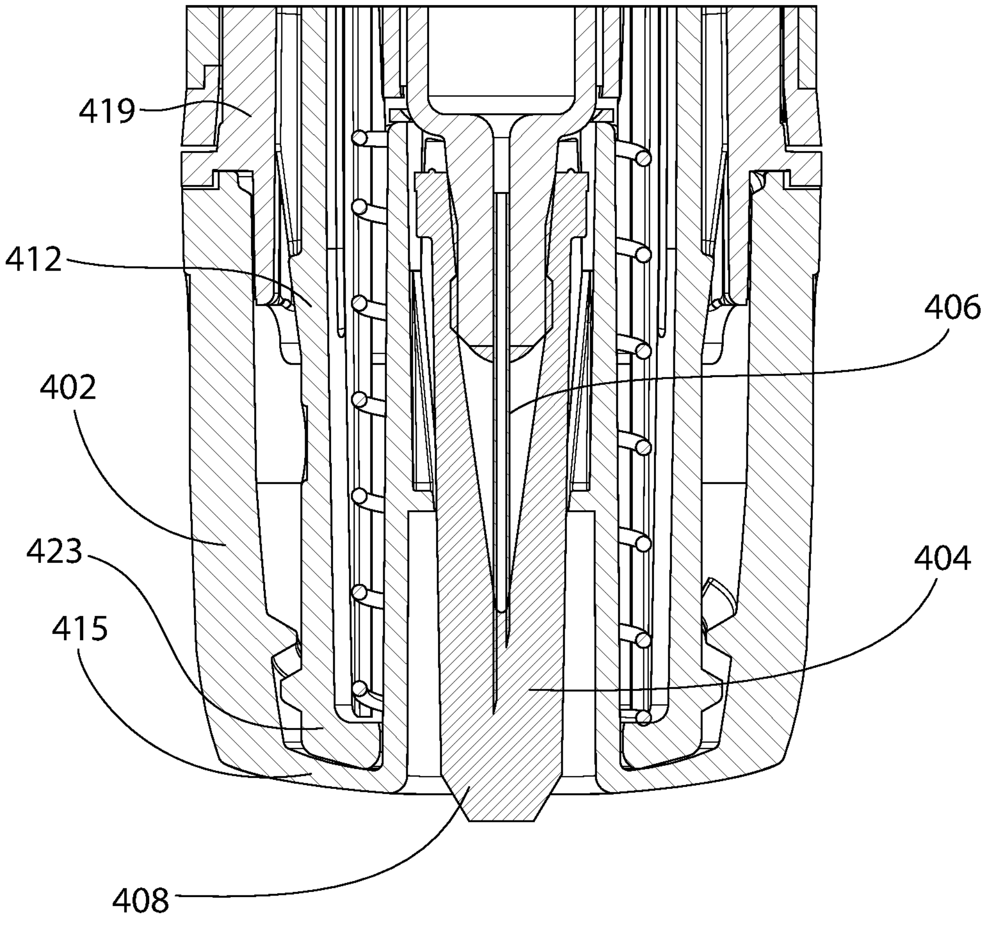
FIG. 30 is a close-up sectional view of the safety cap of FIG. 28 with a needle in the needle shield.
Figure 31:
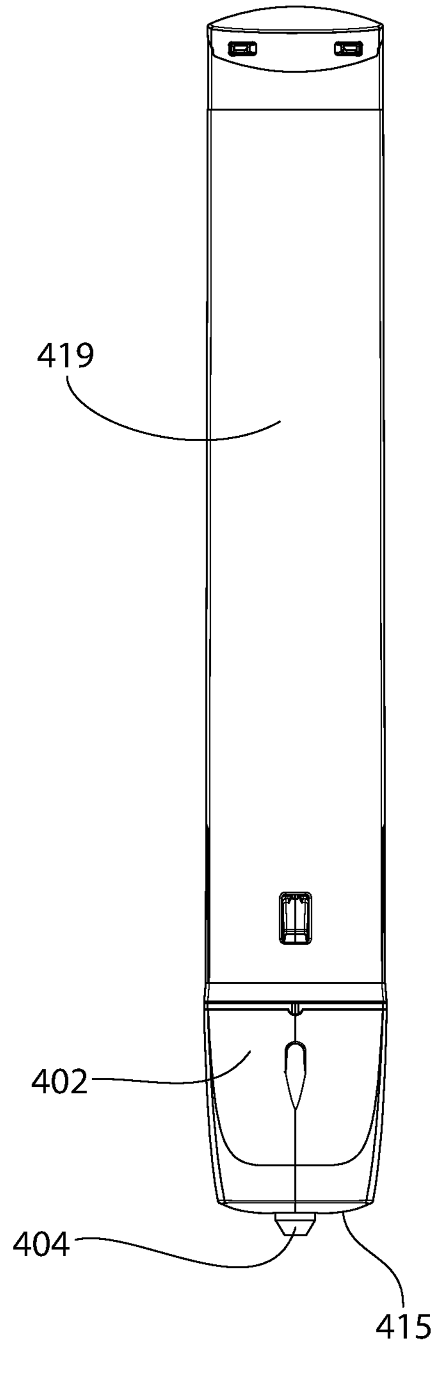
FIG. 31 is a side elevational view of the injection device of FIG. 28.

Referring to FIG. 30, in one embodiment, a needle shield 404 may be coupled to needle 406. Needle shield 404 may be disposed around needle 406 to protect needle 406. For example, needle shield 404 may be partially surrounding needle 406 to ensure that needle 406 is protected during assembly or storage. In some embodiments, needle shield 404 is flexible or resilient. In other embodiments, needle shield 404 is rigid or at least a portion of needle shield 404 is rigid. Arms 410 of safety cap 402 may flex radially outwardly as cap 402 is coupled to housing 419 and needle shield 404 is moved into the recess defined by arms 410. Needle shield 404 may be disposed around needle 406 when needle 406 is disposed within safety cap 402.

Still referring to FIG. 30, in one embodiment, at least a portion of needle shield 404 axially extends through distal end 408 of safety cap 402 when safety cap 402 is affixed to injection device 100. For example, when safety cap 402 is removably affixed to injection device 100, needle shield 404 may be disposed around needle 406 and may be disposed within safety cap 402 such that needle shield 404 extends out from distal end 408 of safety cap 402. In some embodiments, a portion of needle shield 404 is within end wall opening 403 when safety cap 402 is coupled to injection device 100. In other embodiments, needle shield 404 is not within end wall opening 403 when safety cap 402 is coupled to injection device 100. End wall opening 403 may be sized such that needle shield 404 engages the portion of end wall 421 defining end wall opening 403. Needle shield 404 may be compressible and needle shield 404 may be compressed (e.g., radially compressed or axially compressed) when a portion of needle shield 404 is within end wall opening 403.

Needle shield 404 may form a fluid tight seal with end wall 421 when needle shield 404 is within end wall opening 403.

In one embodiment, safety cap 402 may include needle shield remover 405. Needle shield remover 405 may be located at proximal end 407 of safety cap 402. Needle shield remover 405 may be configured to remove needle shield 404 from needle 406 while safety cap 402 is removed from injection device 100. For example, when injection device 100 is ready for use, safety cap 402 may be removed, thereby causing the removal of needle shield 404, thus exposing needle 406. Needle shield remover 405 may include arms 410.

Figure 32:
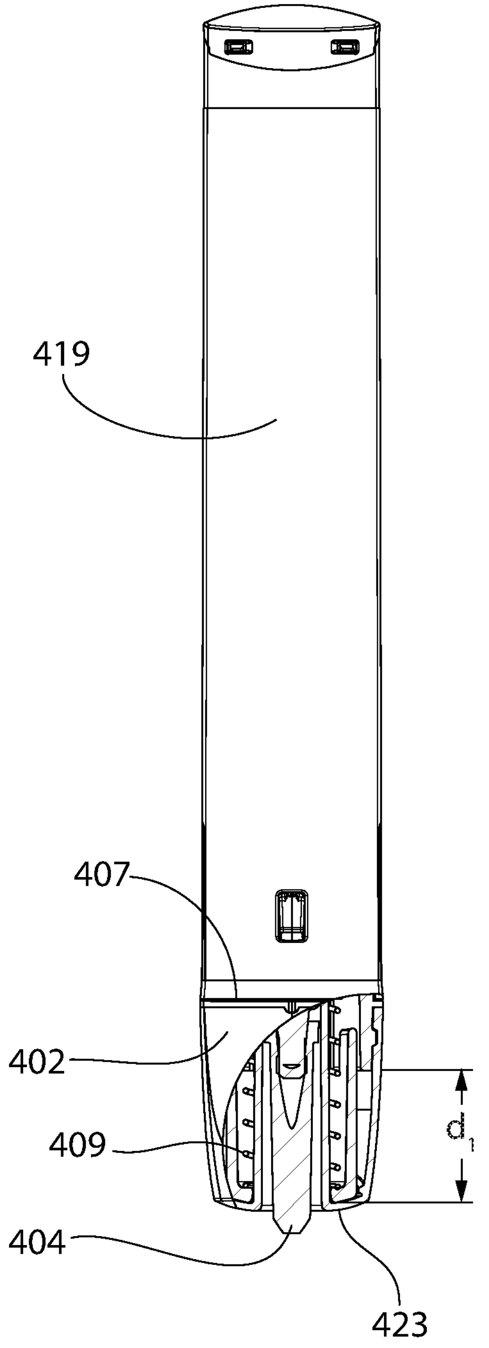
FIG. 32 is a side elevational view of the injection device of FIG. 28 with portions of the safety cap removed to show internal components.

Referring to FIGS. 31-36, injection device 100 may include needle guard 412. Needle guard 412 may be movably coupled to housing 419 of injection device 100. For example, needle guard 412 may be movable between a storage position, a pre-injection position, an injection position, and a post injection position. A biasing element 409 may bias needle guard 412 toward an extended position (FIG. 32). In one embodiment, when safety cap 400 is affixed to injection device 100, needle guard 412 may be in a storage position where needle guard 412 is partially retracted. For example, when safety cap 402 is affixed to injection device 100, distal end 423 of needle guard 412 may abut bottom surface 415 of safety cap 402, prevent needle guard 412 from fully extending under the force from the biasing element 409.

Referring to FIG. 32, a distal end 423 of needle guard 412 may extend a distance di from the housing 419 in the retracted position. Distance $d_1$ may be about 0.4 inches, about 0.5 inches, about 0.6 inches, about 0.7 inches, about 0.8 inches, about 0.9 inches, or about 1 inch. When needle guard 412 is in the storage position and thus partially retracted, the trigger member 300 or trigger member 1400 may be in a pre-firing configuration.

Figure 33:
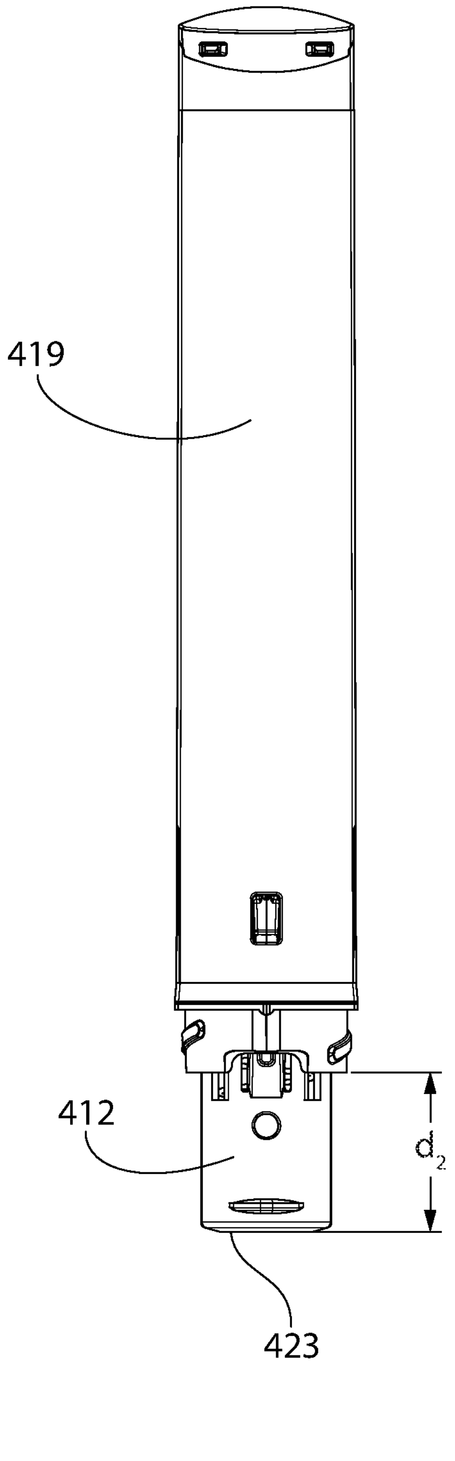
FIG. 33 is a side elevational view of the injection device of FIG. 28 with the safety cap removed and the needle guard in a pre-injection position.

Referring to FIG. 33, when safety cap 402 is removed from injection device 100, needle guard 412 may move to a pre-injection position where needle guard 412 is in a fully extended position. Biasing element 409 may move needle guard 412 as safety cap 402 is detached from housing 419. A distal end of needle guard 412 may extend a distance $d_2$ from housing 419 in the pre-injection position. Distance $d_2$ may be about 0.4 inches, about 0.5 inches, about 0.6 inches, about 0.7 inches, about 0.8 inches, about 0.9 inches, about 1 inch, about 1.1 inches, about 1.2 inches, about 1.3 inches, about 1.4 inches, or about 1.5 inches.

In one embodiment, decoupling safety cap 402 from housing 419 may simultaneously result in needle guard 412 moving to the pre-injection position. Needle guard 412 may be fully extended when needle guard 412 is in the pre-injection position. Removing safety cap 402 may also remove needle shield 404 from needle 406. In some embodiments, removing safety cap 402 from housing 419 simultaneously moves needle guard 412 to the pre-injection position and removes needle shield 404 from needle 406. Needle guard 412 may be in the pre-injection position before a proximal end 407 of safety cap 402 is moved axially beyond a distal end of needle 406. Needle guard 412 being in a pre-injection position and fully extended before needle shield 404 is fully removed from needle 406 may prevent inadvertent contact with needle 406. In one embodiment, when needle guard 412 is in a pre-injection position, distal end 423 of needle guard 412 may be further from housing 419 than when needle guard 412 is in the storage position. In some embodiments, distance $d_2$ is greater than distance di.

Figure 34:
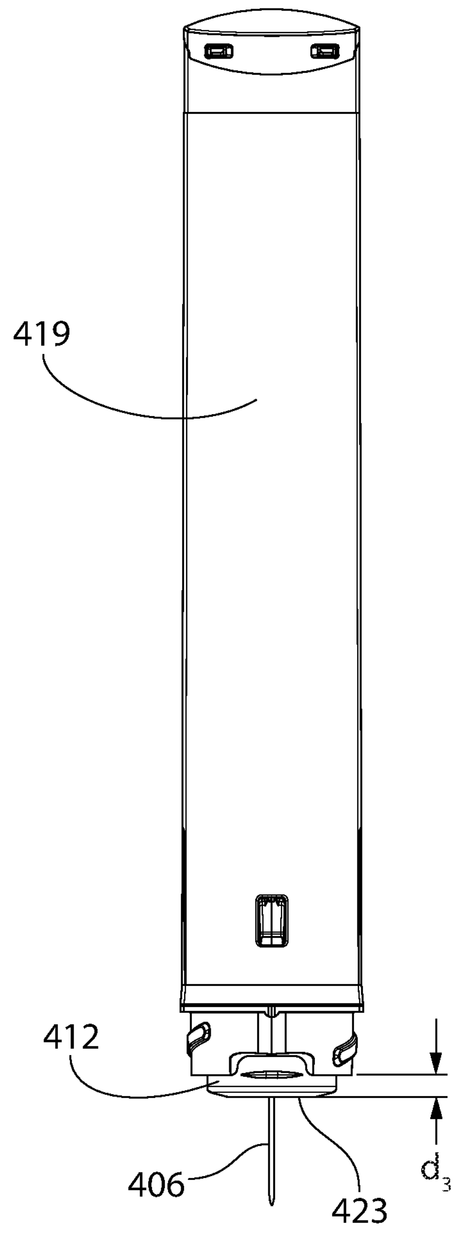
FIG. 34 is a side elevational view of the injection device of FIG. 28 with the safety cap removed and the needle guard in a triggering position.
Figure 35:
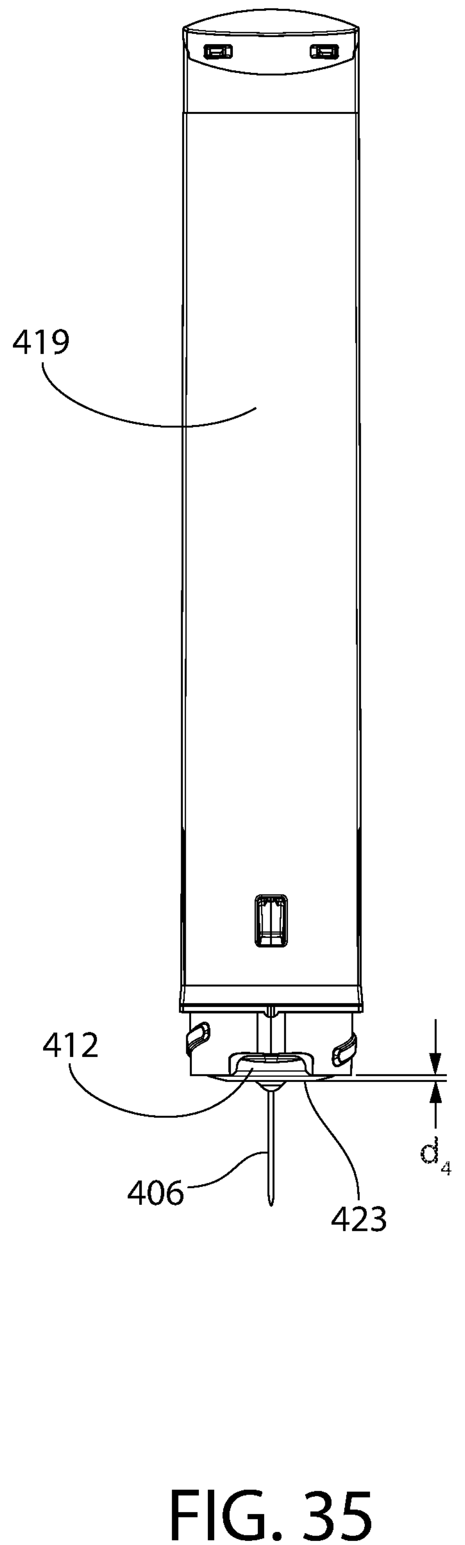
FIG. 35 is a side elevational view of the injection device of FIG. 28 with the safety cap removed and the needle guard in an injection position.

Referring to FIGS. 34-35, needle guard 412 may be retracted, or moved from the pre-injection position to the injection position, via a force applied to distal end 423 of needle guard 412. For example, when distal end 423 of needle guard 412 comes into contact with a surface, such as an injection site, a force may be applied to distal end 423 of needle guard 412 resulting in needle guard 412 retracting. As needle guard 412 is moved from the pre-injection position (FIG. 33) to the injection position (FIG. 35), needle guard 412 may move trigger member (e.g., trigger member 300 or trigger member 1400) to cause an injection. Needle guard 412 may move trigger member to begin the injection sequence prior to the needle guard being in the injection position (e.g., when needle guard is in a triggering position FIG. 34). Distal end 423 of needle guard 412 may be at a distance $d_3$ from housing 419 when needle guard 412 triggers the trigger member. In some embodiments, distance $d_3$ may be about 0.05 inches, about 0.1 inches, about 0.15 inches, about 0.2 inches, or about 0.25 inches.

Referring to FIG. 35, needle guard 412 may be moved to an injection position where needle guard 412 is retracted to expose needle 406 for injection of the medicament through needle 406. In some embodiments, needle guard 412 is fully retracted in the injection position. A distal end 423 of needle guard 412 may be at a distance $d_4$ when needle guard is in the injection position. In some embodiments, distance $d_4$ is about 0.01 inches, about 0.03 inches, about 0.05 inches, about 0.75 inches, or about 0.1 inches. When needle guard 412 is in the injection position, distal end 423 of needle guard 412 may be adjacent to housing 419. Distance $d_1$ may be greater than distance $d_4$. In one embodiment, when needle guard 412 is in the injection position and thus fully retracted, the trigger member may be in a firing configuration. Needle guard 412 being in the injection position and fully retracted may result in expelling of a medicament from injection device 100 through needle 406.

Figure 36:
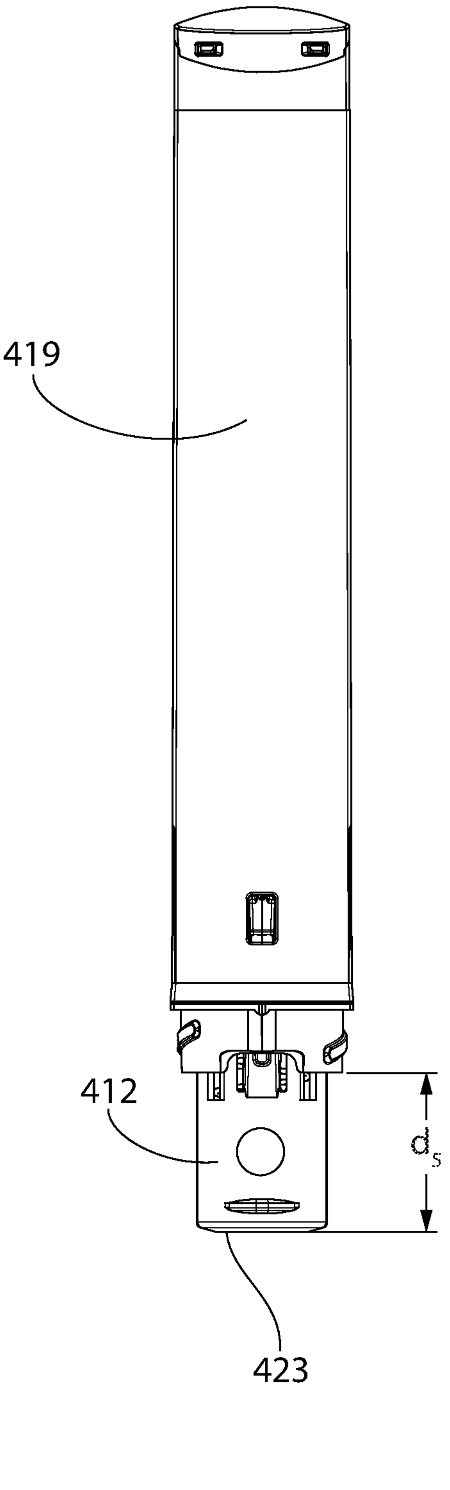
FIG. 36 is a side elevational view of the injection device of FIG. 28 with the safety cap removed and the needle guard in a post-injection position.

Referring to FIG. 36, needle guard 412 may move to a post-injection position when the injection device 100 is removed from the injection site. Needle guard 412 may move to the post-injection position after medicament is expelled. Biasing element 409 may move needle guard 412 to a post-injection position when injection device 100 is removed from the injection site. Needle guard 412 may be fully extended in the post-injection position. Post-injection position of needle guard 412 may be similar to the pre-injection position. Distal end 423 of needle guard 412 may be at a distance ds from housing 419 when needle guard 412 is in the post-injection position. In some embodiments, distance ds is about 0.4 inches, about 0.5 inches, about 0.6 inches, about 0.7 inches, about 0.8 inches, about 0.9 inches, or about 1 inch. In some embodiments, distance di and distance ds equal. In other embodiments, distance ds is greater than distance di. In still other embodiments, distance di is greater than distance $d_5$ Needle guard 412 being in the post-injection position, may result in needle guard 412 being locked out as previously described. Needle guard 412 being locked out may prevent needle guard 412 from retracting. Needle guard 412 being locked out in the post-injection position may prevent axial movement of needle guard 412 and thus exposure of needle 406. Further, needle guard 412 being in the post-injection position prevents repeat injections or inadvertent contact with needle 406.

In one embodiment, the medicament administered by injector 100 comprises Naloxone or a pharmaceutically acceptable salt, solvate, hydrate, cocrystal, or prodrug thereof. In one embodiment, the medicament comprises Naloxone hydrochloride. In one embodiment, the medicament comprises Naloxone hydrochloride dehydrates. In one embodiment, the medicament comprises Naloxone or a pharmaceutically acceptable salt thereof.

In one embodiment, the medicament further comprises a chelating agent selected from the group consisting of edetate disodium (EDTA), D-gluconic acid 8-lactone, sodium or potassium gluconate, sodium triphosphate, sodium hexametaphosphate, and pharmaceutically acceptable salts thereof.

In one embodiment, the medicament further comprises edetate disodium (EDTA). In one embodiment, the medicament further comprises EDTA in an amount of from about 0.001 to 1% wt/v %, about 0.002 to 1% wt/v %, about 0.003 to 1% wt/v %, about 0.004 to 1% wt/v %, about 0.005 to 1% wt/v %, about 0.006 to 1% wt/v %, about 0.007 to 1% wt/v %, about 0.008 to 1% wt/v %, about 0.009 to 1% wt/v %, about 0.01 to 1% wt/v %, about 0.02 to 1% wt/v %, about 0.03 to 1% wt/v %, about 0.04 to 1% wt/v %, about 0.05 to 1% wt/v %, about 0.06 to 1% wt/v %, about 0.07 to 1% wt/v %, about 0.08 to 1% wt/v %, about 0.09 to 1% wt/v %, about 0.1 to 1% wt/v %, about 0.2 to 1% wt/v %, about 0.3 to 1% wt/v %, about 0.4 to 1% wt/v %, about 0.5 to 1% wt/v %, about 0.6 to 1% wt/v %, about 0.7 to 1% wt/v %, about 0.8 to 1% wt/v %, about 0.9 to 1% wt/v %, about 0.01 to 0.1% wt/v %, about 0.02 to 0.1% wt/v %, about 0.03 to 0.1% wt/v %, about 0.04 to 0.1% wt/v %, about 0.05 to 0.1% wt/v %, about 0.06 to 0.1% wt/v %, about 0.07 to 0.1% wt/v %, about 0.08 to 0.1% wt/v %, about 0.09 to 0.1% wt/v %, about 0.02 to 0.09% wt/v %, about 0.03 to 0.08% wt/v %, about 0.04 to 0.07% wt/v %, or about 0.05 to 0.06% wt/v %.

In one embodiment, the medicament further comprises EDTA in an amount of about 0.001 wt/v %, about 0.002 wt/v %, about 0.003 wt/v %, about 0.004 wt/v %, about 0.005 wt/v %, about 0.006 wt/v %, about 0.007 wt/v %, about 0.008 wt/v %, about 0.009 wt/v %, about 0.01 wt/v %, about 0.02 wt/v %, about 0.03 wt/v %, about 0.04 wt/v %, about 0.05 wt/v %, about 0.06 wt/v %, about 0.07 wt/v %, about 0.08 wt/v %, about 0.09 wt/v %, about 0.1 wt/v %, about 0.15 wt/v %, about 0.20 wt/v %, about 0.25 wt/v %, about 0.30 wt/v %, about 0.35 wt/v %, about 0.40 wt/v %, about 0.45 wt/v %, about 0.50 wt/v %, about 0.55 wt/v %, about 0.60 wt/v %, about 0.65 wt/v %, about 0.70 wt/v %, about 0.75 wt/v %, about 0.80 wt/v %, about 0.85 wt/v %, about 0.90 wt/v %, about 0.95 wt/v %, or about 1 wt/v %.

In one embodiment, the medicament further comprises one or more tonicity-adjusting agents, such as, at least one of dextrose, glycerin, mannitol, potassium chloride, sodium chloride, or combinations thereof.

In one embodiment, the medicament further comprises one or more a pH-adjusting agent, such as, at least one of hydrochloric acid, citric acid, acetic acid, phosphoric acid, or combinations thereof.

In one embodiment, the medicament described herein is administered to a human subject in need thereof by injection device 100. In another embodiment, the medicament described herein is administered to a human subject in need thereof by injection device described in Appendix A.

Naloxone is known chemically as 17-allyl-4,5α-epoxy, 3-14-dihydroxymorphine-6-one. It is a weak base with pKa of 7.9 and log P of 1.92. The empirical formula is $C_{19}H_{21}NO_4$ and the molecular weight is 327.38. The structural formula of Naloxone is described below:

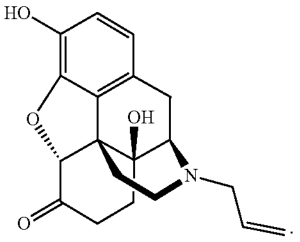

Naloxone hydrochloride is the active ingredient in Naloxone hydrochloride injection products and supplied as Naloxone hydrochloride dihydrate. Naloxone hydrochloride occurs as a white to slightly off-white powder, and is soluble in water, slightly soluble in alcohol, practically insoluble in ether and in chloroform. Naloxone hydrochloride dihydrate has molecular weight of 399.87 while Naloxone hydrochloride molecular weight is 363.84. Thus, 1.1 mg of Naloxone hydrochloride dihydrate is equivalent to 1.0 mg of Naloxone hydrochloride.

Figure 19:
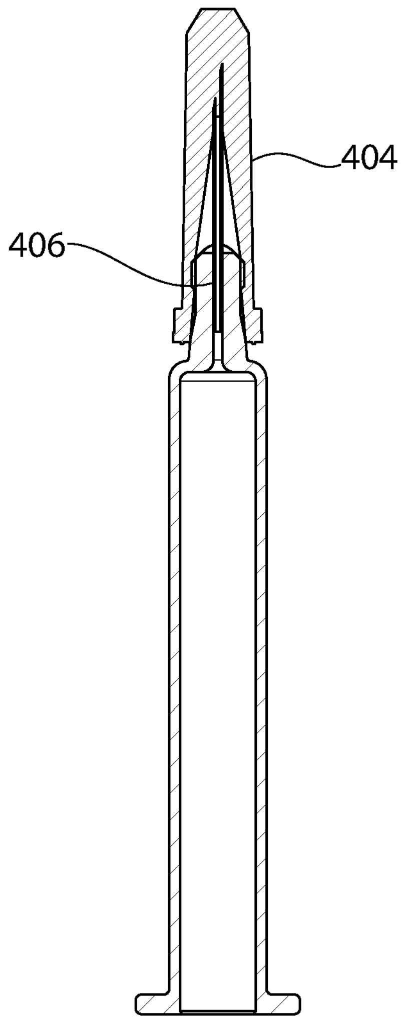
FIG. 19 shows a syringe in accordance with an exemplary embodiment of the present invention.
Figure 20:
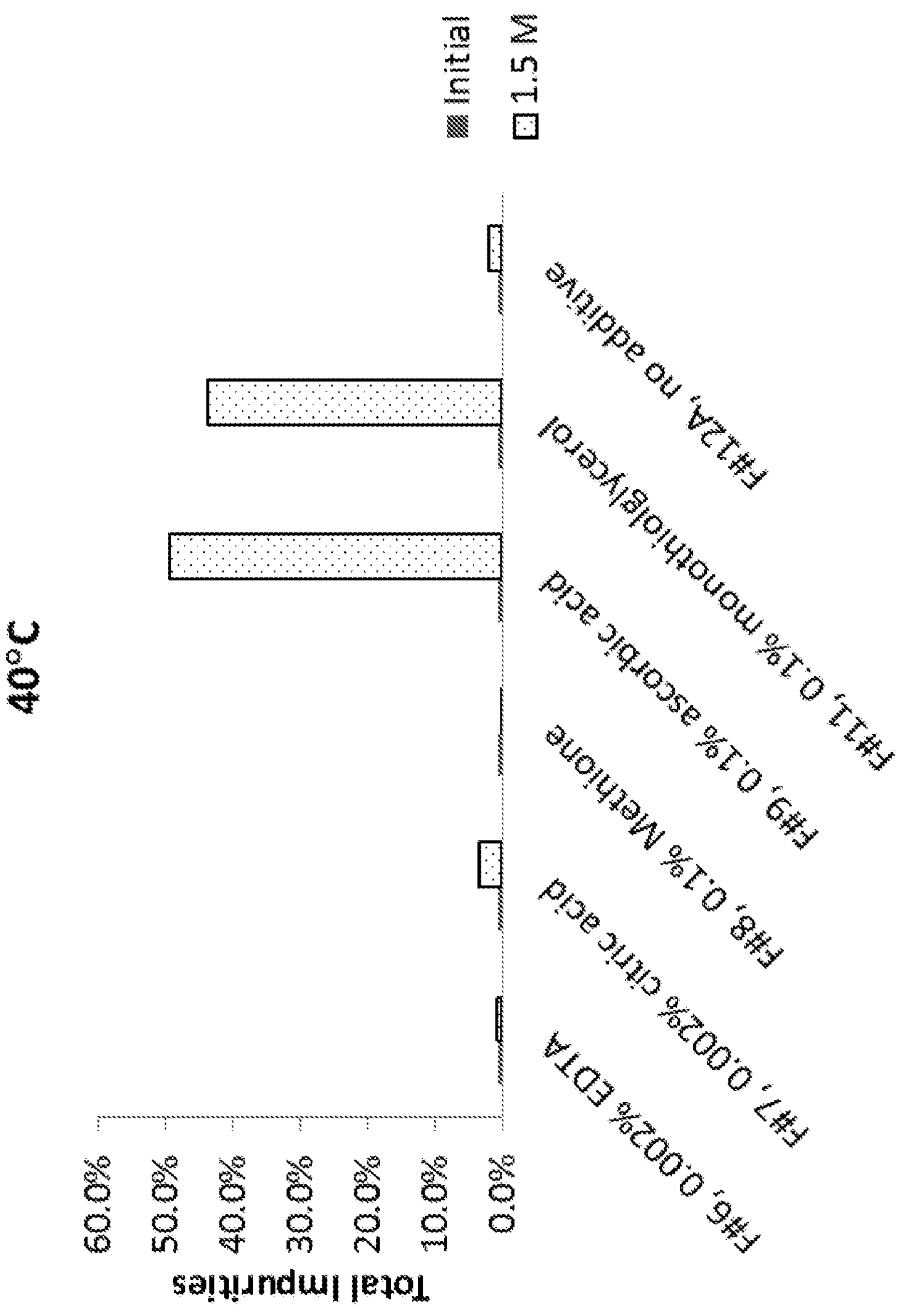
FIG. 20 is a bar graph depicting the stability results of formulations #6, #7, #8, #9. #11, and #12A at 40° C. for 1.5 months.

In an embodiment, the medicament container for Naloxone hydrochloride injection, includes standard packaging components for injection. Naloxone hydrochloride will be aseptically filled into a siliconized USP Type I clear glass syringe barrel fitted with a fixed siliconized stainless steel needle that is protected with a latex-free soft needle shield. The medicament container consists of a latex-free grey chlorobutyl elastomer plunger stopper. Syringes and stoppers used in development stability are provided in Table 5. In an embodiment, Ompi Syringe with 22G ⅝" needle is used for delivery through clothes. In an embodiment, Scott syringe with 27G ½" needle is used for delivery through clothes. The drawing of Ompi syringe is shown in FIG. 19. The two types of plunger stoppers evaluated are both siliconized gray chlorobutyl stoppers from West Pharmaceutical Services, while item 10149656 contains B2-40 flurotec coating. Stoppers with flurotec coating has advantages of very low particulate level and effective barrier minimizing interaction between the drug and the closure but needs the use of vacuum stoppering due to the film rigidity.

In an embodiment, the injector described herein, including injection device 100 and 5030, comprises a medicament comprising Naloxone hydrochloride. In an embodiment, the medicament contains a sterile, nonpyrogenic clear colorless solution in water comprising naloxone hydrochloride for injection administered through intramuscular or subcutaneous injection in a single 0.4 mL dose to yield a final delivered dose of naloxone hydrochloride at 0.4 mg or 2 mg. In an embodiment, the naloxone hydrochloride composition is contained in a 1 mL long pre-filled syringe with 22G ⅝" needle for emergency use possibly through clothes. In an embodiment, the medicament complies with USP monograph for Naloxone hydrochloride injection (USP 40, Naloxone hydrochloride injection). USP 40 defines Naloxone hydrochloride injection as a sterile, isotonic solution of Naloxone hydrochloride in water for injection. It contains not less than 90.0% and not more than 110.0% of the labeled amount of Naloxone hydrochloride ($C_{19}H_{21}NO_4 \cdot HCl$). Naloxone hydrochloride injection is light sensitive and needs protection from light. In an embodiment, the medicament is defined in Table 2.

TABLE 2

| Criteria | Naloxone hydrochloride injection |
|---|---|
| Product | Single-use Naloxone HCl Injection in prefilled syringe with Autoinjector |
| Dose strength | 0.4 mg, 2 mg |
| Dosage form | Sterile solution |
| Formula | Complies with USP Naloxone HCl Injection, isotonic, similar to marketed Naloxone HCl Injection |
| Dose concentration | 1 mg/mL, 5 mg/mL |
| Delivery volume | 0.4 mL |
| Syringe | 1 mL long Prefilled syringe, 22 G ⅝" needle |
| Plunger Stopper | West 4432/50 Gray for 1 mL long syringe |
| Route of administration | Subcutaneous or intramuscular |
| Drug release | Immediate release |
| Delivery platform | Quickshot |
| Stability | Shelf life 24 months at room temperature storage |

TABLE 3

| Syringes | | | | |
|---|---|---|---|---|
| Article Co. | Description | Supplier | Material | Size |
| 760007.6977 | Syringe EZ-Fill 1 mL Long, 22 G ⅝" | Ompi | Clear borosilicate USP/Ph.Eur Type I glass, siliconized barrel; Stainless steel, siliconized needle; polyisoprene, latex free soft needle shield | 1 mL long syringe barrel with 22 G, ⅝" needle |
| 1469924 | SyriQ Sterile 1 mL Lg SN SF 27G × ½" VB TW NS 4800GS | Schott | Clear borosilicate USP/Ph.Eur Type 1 glass, siliconized barrel; Stainless steel, siliconized needle; polyisoprene, latex free soft needle shield | 1 mL long syringe barrel with 27 G, ½" needle |
| 10149656 | Article 2340 4432/50 Gray B2-40 Coated Westar RU | West | 4432/50 Gray Elastomer (Chlorobutyl), USP Type I Closure, Latex free, Siliconized, B2-40 coating, FluroTec | 1 mL Long |
| 10149601 (West) 1195953 (Schott) | Article 2212 4432/50 Gray | Schott (West) | 4432/50 Gray Elastomer (Chlorobutyl), USP Type I Closure, Latex free, Siliconized | 1 mL Long |

While injection device 100 can deliver an injection of up to about 3 mL per injection, other volumes can be injected in alternative embodiments. In certain embodiments, injection device 100 can deliver an injection of greater than 1 mL per injection. In other embodiments, injection device 100 can deliver an injection in range of about 0.2 mL to about 3 mL. In one embodiment, injection device 100 can deliver an injection of 0.4 ml Naloxone formulations described herein.

In one embodiment, injector device 100 can inject 0.5 ml or 0.4 ml of a medicament dissolved in an aqueous solution in about 0.1 sec., about 0.2 sec., about 0.3 sec., about 0.4 sec., about 0.5 sec., about 0.6 sec., about 0.7 sec., about 0.8 sec., about 0.9 sec., about 1.0 sec., or any range determinable from the preceding times (for example, about 0.5 sec. to about 1.0 sec. or about 0.4 sec. to about 0.6 sec.). In another embodiment, injector device 100 can inject 0.5 ml or 0.4 ml of a medicament dissolved in oil in about 5 sec., about 6 sec., about 7 sec., about 8 sec., about 9 sec., about 10 sec., about 11 sec., about 12 sec., about 13 sec., about 14 sec., about 15 sec., or any range determinable from the preceding times (for example, about 6 sec. to about 7 sec. or about 5 sec. to about 15 sec.). In an alternate embodiment, injection device 100 can injection viscous materials in and about the ejection times as shown in Tables 1 and 2. Other volumes and times are determinable from the described preceding information and Tables 4 and 5.

Tables 4 and 5 show observed injection time for viscous oil medicament for one embodiment of injection device 100.

TABLE 4

| Injection time - 27 g regular wall needle | | |
|---|---|---|
| Volume | Time | Temperature |
| 0.2 ml | 6.9 sec | 10 C. |
| | 8.4 sec | |
| | 2.9 sec | 25 C. |
| | 3.3 sec | |
| 0.5 ml | 17.4 sec | 10 C. |
| | 21.1 sec | |
| | 7.4 sec | 25 C. |
| | 8.3 sec | |

TABLE 4-continued

| Injection time - 27 g regular wall needle | | |
|---|---|---|
| Volume | Time | Temperature |
| 1.0 ml | 34.7 sec | 10 C. |
| | 42.1 sec | |
| | 14.7 sec | 25 C. |
| | 16.6 sec | |
| 2.0 ml | 69.5 sec | 10 C. |
| | 84.2 sec | |
| | 29.5 sec | 25 C. |
| | 33.3 sec | |
| 3.0 ml | 104.2 sec | 10 C. |
| | 126.3 sec | |
| | 44.2 sec | 25 C. |
| | 49.9 sec | |

TABLE 5

| Injection time - 27 g thin walled needle | | |
|---|---|---|
| Volume | Time | Temperature |
| 0.2 ml | 2.8 sec | 10 C. |
| | 2.9 sec | |
| | 1.3 sec | 25 C. |
| | 1.5 sec | |
| 0.5 ml | 6.9 sec | 10 C. |
| | 7.3 sec | |
| | 3.3 sec | 25 C. |
| | 3.7 sec | |
| 1.0 ml | 13.9 sec | 10 C. |
| | 14.7 sec | |
| | 6.5 sec | 25 C. |
| | 7.3 sec | |
| 2.0 ml | 27.8 sec | 10 C. |
| | 29.4 sec | |
| | 13.1 sec | 25 C. |
| | 14.7 sec | |
| 3.0 ml | 41.6 sec | 10 C. |
| | 44.1 sec | |
| | 19.6 sec | 25 C. |
| | 22.0 sec | |

According to certain exemplary embodiments, injection device 100 can be configured to inject medicament stored within a prefilled syringe. Prefilled syringes that are manufactured by a blown glass process can have significant dimensional tolerances and unevenness. Accordingly, features of injection device 100 can serve to accommodate the shape irregularities and to properly position and locate a prefilled syringe within injection device 100. Other medicament containers such as prefilled syringes manufactured with polymers can also be accommodated. Further, in one embodiment, injection device 100 can be configured as a needle-assisted jet injector, providing a peak pressure during the injection of less than about 1,000 p.s.i., in one embodiment, less than 500 p.s.i., and in another embodiment less than about 400 p.s.i. In one embodiment, injection device 100 can provide a peak pressure during the injection of about 300 p.s.i., about 325 p.s.i., about 350 p.s.i., about 375 p.s.i., about 400 p.s.i., about 425 p.s.i., about 450 p.s.i., about 475 p.s.i., about 500 p.s.i., about 525 p.s.i., about 550 p.s.i., about 575 p.s.i., about 600 p.s.i., about 625 p.s.i., about 650 p.s.i., about 675 p.s.i., about 700 p.s.i., about 725 p.s.i., about 750 p.s.i., about 775 p.s.i., about 800 p.s.i., about 825 p.s.i., about 850 p.s.i., about 875 p.s.i., about 900 p.s.i., about 925 p.s.i., about 950 p.s.i., about 975 p.s.i., about 1,000 p.s.i., about 1,025 p.s.i., or any range determinable from the peak pressures (for example, about 500 p.s.i. to about 650 p.s.i. or about 1000 p.s.i. to about 1025 p.s.i.).At an end of an injection, the pressure applied to the medicament is, in one embodiment, at least about 80 p.s.i., in another embodiment, at least about 90 p.s.i., and, in another embodiment, at least about 100 p.s.i. In one embodiment, the pressure applied to the medicament at an end of an injection is about 50 p.s.i., about 60 p.s.i., about 70 p.s.i., about 80 p.s.i., about 90 p.s.i., about 100 p.s.i., about 110 p.s.i., about 120 p.s.i., about 130 p.s.i., or any range determinable from the pressures (for example, about 50 p.s.i. to about 60 p.s.i. or about 100 p.s.i. to about 110 p.s.i.). In one embodiment, the initial pressure can be around 330 p.s.i., and the final pressure can be about 180 p.s.i., while in another embodiment the initial pressure can be about 400 p.s.i., dropping to around 300 p.s.i. at the end of the injection. These exemplary pressures can, for example, result in a flow rate of about 0.2 mL/sec to 1.20 mL/sec, and, in one embodiment, be about 1.0 mL/sec. In one embodiment, the rate is greater than 0.2 mL/sec. In one embodiment, injection device 100 may include an energy source e.g., a high force spring, such as those needed for rapid ejection of difficult to eject medicaments. In one embodiment, energy source is a high force spring of about 18 lbs. load capacity, about 18.5 lbs load capacity, about 19 lbs. load capacity, about 19.5 lbs. load capacity, about 20 lbs. load capacity, about 20.5 lbs. load capacity, about 21 lbs. load capacity, about 21.5 lbs. load capacity, about 22 lbs. load capacity, about 22.5 lbs. load capacity, about 23 lbs. load capacity, or any range determinable from the preceding load capacities (for example, about 18 lbs. load capacity to about 23 lbs load capacity or about 18 lbs. load capacity to about 19 lbs. load capacity). High force springs may be desired in situations where rapid delivery of drugs is important to assure injection of the entire dose; this would be to counteract users removing the injector from the injection site prematurely. Medicaments can be difficult to eject due to either high viscosity or because of a combination of their viscosity and a therapeutic need for delivery of the medicament using fine bore needles, such as the 29 gauge prefilled syringe. These exemplary high spring forces for difficult to inject medicaments can result in a flow rate of about 0.03 mL/sec to about 1.0 mL/sec. In an embodiment, the spring force of the injector described herein is between about 5 to 23 lbf, about 6 to 22 lbf, about 7 to 21 lbf, about 8 to 20 lbf, about 9 to 19 lbf, about 10 to 18 lbf, about 11 to 17 lbf, about 12 to 16 lbf, about 13 to 15 lbf, about 13 to 14 lbf, about 5 to 20 lbf, about 6 to 20 lbf, about 7 to 20 lbf, about 8 to 20 lbf, about 9 to 20 lbf, about 10 to 20 lbf, about 11 to 20 lbf, about 12 to 20 lbf, about 13 to 20 lbf, about 14 to 20 lbf, about 15 to 20 lbf, about 16 to 20 lbf, about 17 to 20 lbf, about 18 to 20 lbf, about 19 to 20 lbf, about 5 to 19 lbf, about 6 to 19 lbf, about 7 to 19 lbf, about 8 to 19 lbf, about 9 to 19 lbf, about 10 to 19 lbf, about 11 to 19 lbf, about 12 to 19 lbf, about 13 to 19 lbf, about 14 to 19 lbf, about 15 to 19 lbf, about 16 to 19 lbf, about 17 to 19 lbf, about 18 to 19 lbf, about 5 to 18 lbf, about 6 to 18 lbf, about 7 to 18 lbf, about 8 to 18 lbf, about 9 to 18 lbf, about 10 to 18 lbf, about 11 to 18 lbf, about 12 to 18 lbf, about 13 to 18 lbf, about 14 to 18 lbf, about 15 to 18 lbf, about 16 to 18 lbf, about 17 to 18 lbf, about 5 to 17 lbf, about 6 to 17 lbf, about 7 to 17 lbf, about 8 to 17 lbf, about 9 to 17 lbf, about 10 to 17 lbf, about 11 to 17 bf, about 12 to 17 lbf, about 13 to 17 lbf, about 14 to 17 lbf, about 15 to 17 lbf, about 16 to 17 lbf, about 5 to 16 lbf, about 6 to 16 lbf, about 7 to 16 lbf, about 8 to 16 lbf, about 9 to 16 lbf, about 10 to 16 lbf, about 11 to 16 lbf, about 12 to 16 lbf, about 13 to 16 lbf, about 14 to 16 lbf, about 15 to 16 lbf, about 5 to 15 lbf, about 6 to 15 lbf, about 7 to 15 lbf, about 8 to 15 lbf, about 9 to 15 lbf, about 10 to 15 lbf, about 11 to 15 lbf, about 12 to 15 lbf, about 13 to 15 lbf, or about 14 to 15 lbf.

In an embodiment, the spring force of injection device 100 is about 5 lbf, about 6 lbf, about 7 lbf, about 8 lbf, about 9 lbf, about 10 lbf, about 11 lbf, about 12 lbf, about 13 lbf, about 14 lbf, about 15 lbf, about 16 lbf, about 17 lbf, about 18 lbf, about 19 lbf, about 20 lbf, about 21 lbf, about 22 lbf, or about 23 lbf.

In an embodiment, the spring force of injection device 100 is 9.30 lbf=5% at 1.925 inch length and 15.60 lbf+5% at 1.045 inch length. In an embodiment, the spring force of injection device 100 is 9.41 lbf+5% at 1.925 inch length and 15.60 lbf=5% at 1.045 inch length.

In one embodiment, the needles used may be between 22 and 29 gauge. In some embodiments, the needles used are between 25 and 28 gauge, and, in other embodiments, are around 27 gauge, but alternatively other needle gauges can be used where the other components are cooperatively configured to produce the desired injection. In some embodiments, thin walled needles maybe used without risk of bending when injection device 100 is configured to act with manual needle insertion prior to injection. In certain jet injector embodiments firing aqueous medicaments, the firing mechanism, medicament container, needle, and energy source are configured to produce an average stream velocity within the needle of at least about 1,000 cm/sec, and, in certain embodiments, are at least about 1,300 cm/sec, up to about 3,000 cm/sec, and, in other embodiments, are up to about 8,000 cm/sec. In one embodiment, the average stream velocity during injection is about or reaches between about 1,300 and about 3,000 cm/sec or approximately about 2,000 cm/sec. In one embodiment, the average stream velocity during injection is about or reaches about 500 cm/sec, about 1,000 cm/sec, about 1,500 cm/sec, about 2,000 cm/sec, about 2,500 cm/sec, about 3,000 cm/sec, about 3,500 cm/sec, about 4,000 cm/sec, about 4,500 cm/sec, about 5,000 cm/sec, about 5,500 cm/sec, about 6,000 cm/sec, about 6,500 cm/sec, about 7,000 cm/sec, about 7,500 cm/sec, about 8,000 cm/sec, or any range determinable from the average stream velocities (for example, about 1,000 cm/sec to about 1,500 cm/sec or about 1,500 cm/sec to about 2,000 cm/sec). In one embodiment, the average stream velocity during injection is greater than about 750 cm/sec. In one embodiment, the average stream velocity during injection is greater than about 1250 cm/sec. In one embodiment, the average stream velocity during injection is less than about 5,000 cm/sec. In one embodiment, the average stream velocity during injection is less than about 3,000 cm/sec. In one embodiment, the average stream velocity during injection is less than about 2,000 cm/sec. The velocities used to produce a jet injection will vary for other types of medicaments, such as based on their viscosities. With some viscous medicaments, exemplary high spring forces can be used to produce stream velocity of about 100 cm/sec, up to about 1000 cm/sec. Weaker energy sources, and/or larger needles, for example, can be used to obtain lower velocities and lower pressures and/or flow rates for traditional, low-pressure autoinjector embodiments. Such embodiments can also benefit from the axial rotation between the trigger engagement member and the retaining portion, while moving from the pre-firing condition to the firing condition upon a proximal movement of the skin-contacting member with respect to housing. An example of which, but not limited to, is a reduction of friction between spring loaded components which can be applied to triggering designs not involving rotational motion.

Each and every reference herein is incorporated by reference in its entirety. The entire disclosure of U.S. Pat. Nos. 8,496,619, 8,021,335, 7,776,015, and 6,391,003, U.S. Patent Pat. Application Nos. 2013/0303985, 2013/0331788, 2013/0317431, U.S. patent application Ser. No. 13/184,229 and U.S. provisional patent application Nos. 61/621,298 and 61/643,845 are hereby incorporated herein by reference thereto as if fully set forth herein. The term "about," as used herein, should generally be understood to refer to both the corresponding number and a range of numbers. Moreover, all numerical ranges herein should be understood to include each whole integer within the range.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

EXAMPLES

HPLC Method

HPLC methods used in development analysis and stability is a modified one form EP HPLC method for drug substance, which is considered as stability indicating. The method is summarized in Table 6. Naloxone shows a retention time of 19.5 min with the development HPLC method.

TABLE 6

HPLC method for development analysis and stability

| Item | Development LC Method | EP LC Method |
|---|---|---|
| Column | Zorbax Eclipse XDB-C8 15 cm × 4.6 mm | 12.5 cm × 4.0 mm end-capped octylsilyl silica gel |
| Column Temperature | 40° C. | 40° C. |
| Injection Volume | 10 µL for 5 mg/mL, 50 µL for 1 mg/mL | 20 µL |
| Detection | 230 nm | 230 nm |
| Flow Rate | 1.2 mL/min | 1.5 mL/min |
| Mobile Phase A | Acetonitrile/Tetrahydrofuran/Octanesulfonate Solution 20/40/940 v/v/v | Acetonitrile/Tetrahydrofuran/Octanesulfonate Solution 20/40/940 v/v/v |
| Mobile Phase B | Acetonitrile/Tetrahydrofuran/Octanesulfonate Solution 170/40/790 v/v/v | Acetonitrile/Tetrahydrofuran/Octanesulfonate Solution 170/40/790 v/v/v |

| Gradient Program | Time (min) | % A | % B | Time (min) | % A | % B |
|---|---|---|---|---|---|---|
| | 0 | 100 | 0 | 0 | 100 | 0 |
| | 40 | 0 | 100 | 40 | 0 | 100 |
| | 40.1 | 100 | 0 | 50 | 0 | 100 |
| | 50 | 100 | 0 | | | |
| | 60 | 100 | 0 | | | |

Example 1: Analysis of Naloxone Hydrochloride Injection Commercial Products

Several commercial products of Naloxone hydrochloride injection were procured and analyzed for appearance, pH, osmolality, assay, and impurities. The analytical data is presented in Table 7.

TABLE 7

Analytical Data of Naloxone Hydrochloride Injection Commercial Products

| Product | IMS 1 mg/mL | | | Hospira 0.4 mg/mL |
|---|---|---|---|---|
| NDC# | 76329-3369-1 | | | 0409-1215-01 |
| Presentation | 2 mL Luer-Jet Luer-Lock Prefilled Syringe | | | 1 mL glass vial sealed with a rubber stopper and an aluminum cap |
| Concentration | 1 mg/mL | | | 0.4 mg/mL |
| Batch# | RL018F6 | RL036J6 | RL047C7 | 72-142-EV |
| Expiry Date | May 2018 | Sep 18 | Feb 19 | Dec 18 |
| Test | | | | |
| Description | Clear, colorless solution | Clear, colorless solution | Clear, colorless solution | Clear, colorless solution |
| pH | 3.63 | 3.75 | 3.77 | 4.99 |
| Density (g/mL) | 1.028 | 1.014 | 0.994 | 1.009 |
| Osmolarity (mOsm) | 274 | 287 | 287 | 304 |
| Assay | 100.3% | 100.0% | 100.1% | 101.6% |
| Total Impurities | 0.23% | 0.28% | 0.16% | 0.11% |

Example 2: Formulation Stability

Naloxone hydrochloride, the active ingredient, is soluble in water as described in USP, which means one part of Naloxone hydrochloride can dissolve in 10-30 parts of water. Olofson et al reported that Naloxone hydrochloride is soluble in water at 5% (50 mg/mL) [Tetrahedron Lett, 1567, 1977]. Narcan Nasal Spray contains 4 mg dose of Naloxone hydrochloride in 0.1 mL (40 mg/mL) of purified water. Thus, Naloxone hydrochloride has sufficient solubility to prepare as 1 mg/mL and 5 mg/mL formulations in water for injection.

Naloxone hydrochloride drug substance is very stable and has a retest period of five years for the materials supplied by Mallinckrodt when stored in USP suggested condition, being preserved in tight, light-resistant containers at 25° C., with excursions permitted between 15° C. and 30° C. Naloxone hydrochloride is also expected to be stable in aqueous solution considering multiple solution products marketed including 0.4 mg/mL, 1 mg/mL injection and 40 mg/mL nasal spray in water.

Stability studies were carried out to evaluate the compatibility of Naloxone injection with primary packaging components including 1 mL long syringe with USP Type 1 siliconized glass, stainless steel siliconized needle, and latex free polyisoprene needle shield, and plunger stopper made of chlorobutyl gray elastomer as USP Type I closure. The syringes were manually filled and enclosed with the plunger stoppers for stability evaluation. Additional modified formulations were also studied for stability, with the addition of small amount of stabilizer and antioxidants to the described generic formulation to investigate whether Naloxone stability can be enhanced by those ingredients. Table 8 describes the number of formulations under stability evaluation regarding composition and primary packaging components.

Example 3: Primary Packaging Component

Test Formulations #12A, #12B, and #12C having the same composition with 1 mg/mL Naloxone hydrochloride and 8.35 mg/mL sodium chloride were studied for stability with different combination of syringe and stopper as described in Table 9. As shown in Table 10, there is no detectable incompatibility observed for the types of syringes and stoppers evaluated with Naloxone hydrochloride injection, considering no detectable increase in total impurities was observed after 9 months storage at 25° C. for the three test package configurations. In addition, the levels of total impurities detected during 9 month storage at 40° C. are similar for the three package configurations, further confirming the compatibility. At 40° C., the total impurities were increased to 2-3% after 1.5 month storage, slightly increased to 4-5% after 3 months, and then slightly decreased to 2-3% after 9 months. The increase in total impurities at 40° C. is considered as being formulation related and unacceptable for a commercial product. Experiments were conducted to address this issue through formulation optimization as discussed in the following section.

Stability data at 60° C. shows that the combination with Ompi syringe and Article 2340 4432/50 Gray B2-40 Coated Westar RU offered a better stability for Naloxone hydrochloride injection than the other two, considering the level of impurity increase and the assay value decrease shown in Table 9.

Example 4: Drug Concentration

Test Formulations #12A and 13 differ in drug concentration, 1 mg/mL versus 5 mg/mL, while being kept at the same primary packaging components, maintained at the same pH, and with similar sodium chloride content. It appears that the formulations at the two different concentrations have comparable stability at 25° C., 40° C., and 60° C. as revealed by Table 10. Both formulations are stable when stored at 25° C. for nine months with total impurities being slightly decreased during storage. However, significant increase in impurities were observed after stored 1.5 month at 40° C. and 60° C., reaching above 3% of total percentage area, while the impurity level fluctuates at different time interval up to nine months at 40° C. and 6 months at 60° C. during storage. It is clear that reformulation work is needed to identify formulations with better stability.

Example 5: Reformulation to Improve Stability

The formulation work to improve stability for Naloxone injection involved the selection of antioxidants and stabilizers.

Figure 21:
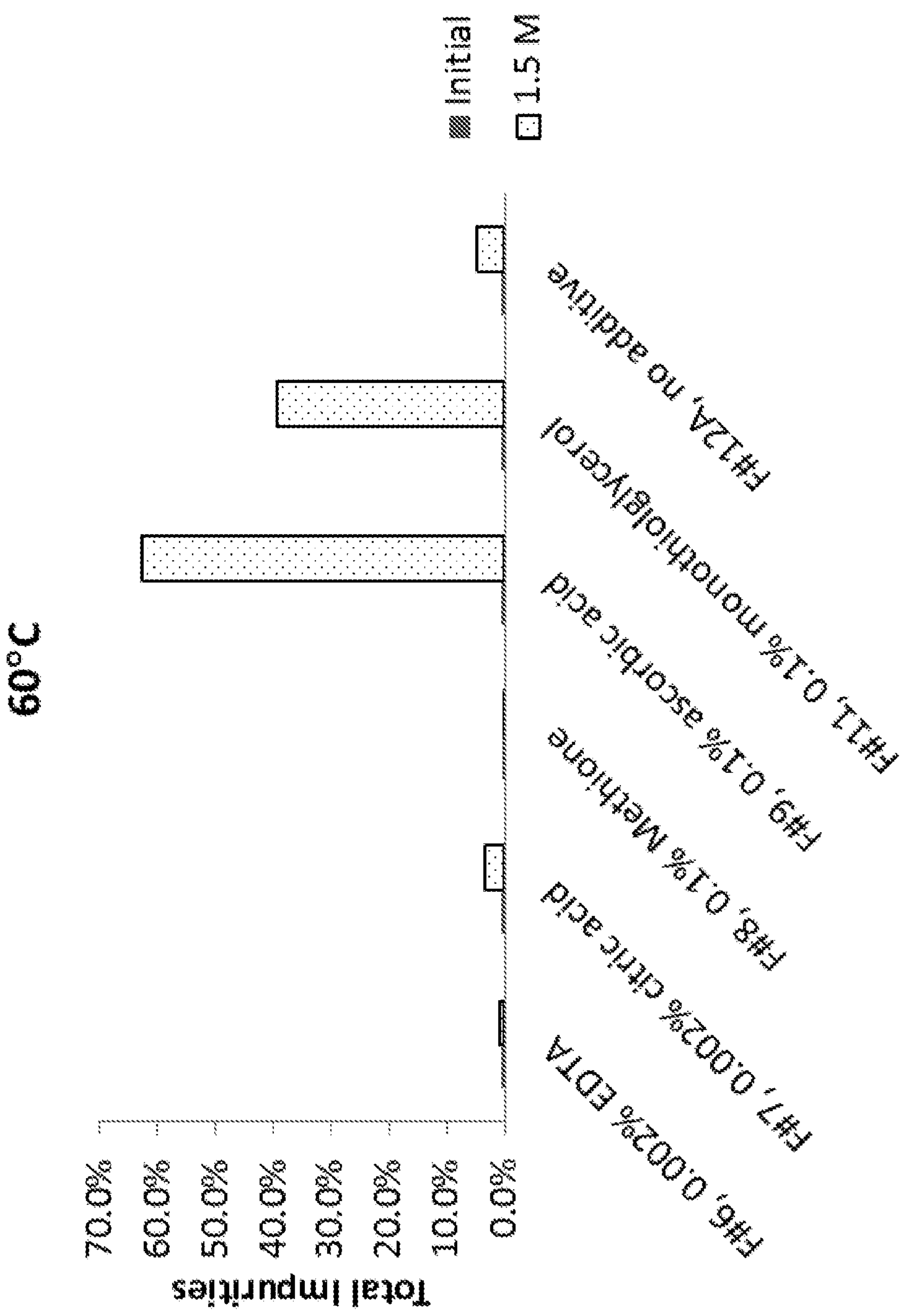
FIG. 21 is a bar graph depicting the stability results of formulations #6, #7, #8, #9. #11, and #12A at 60° C. for 1.5 months.
Figure 22:
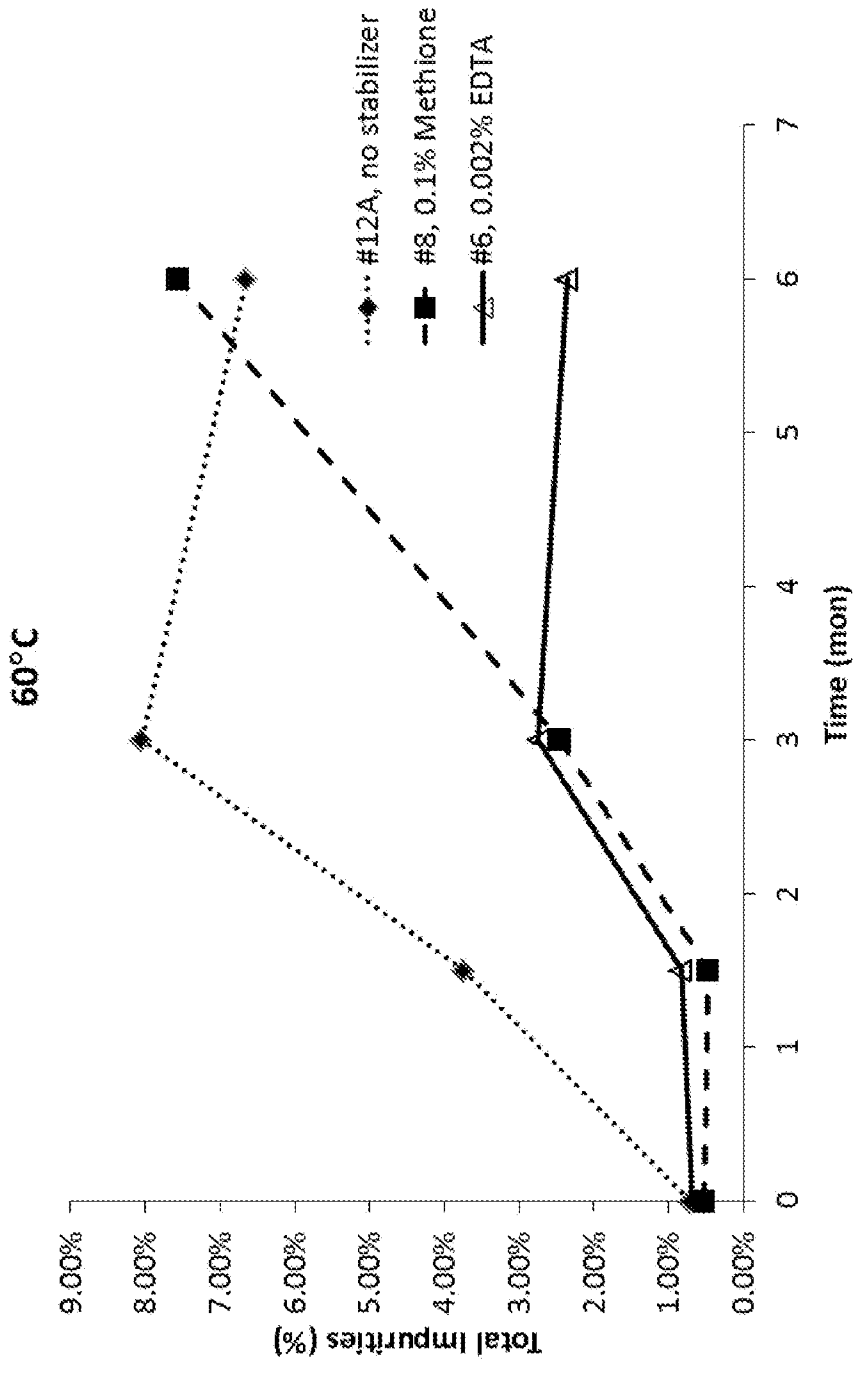
FIG. 22 is a graph depicting the change of total impurities for Naloxone injection formulation #6 (0.002% EDTA), #8 (0.1% Methionine), #12A (no stabilizer) at 60° C.

Table 11 and FIGS. 21 and 22 provide stability results of formulations #6, #7, #8, #9. #11, and #12A at 40° C. and 60° C. for 1.5 month, which have the same Naloxone concentration and the same primary packaging components. The stability data reveals that the presence of ascorbic acid (F #9) or monothioglycerol (F #11) caused significant degradation of naloxone and the use of citric acid (F #7) had no detectable effect, while the addition of edetate disodium (EDTA) (F #6) and methionine (F #8) enhanced the stability of Naloxone, in comparison with the formulation without additive, F #12A.

The formulations containing EDTA and methionine (F #6 and F #8) were furthered monitored for stability at 60° C. for up to 6 months, and at 25° C. and 40° C. for up to 9 months, in comparison the formulation without these excipients, F #12A.

Figure 23:
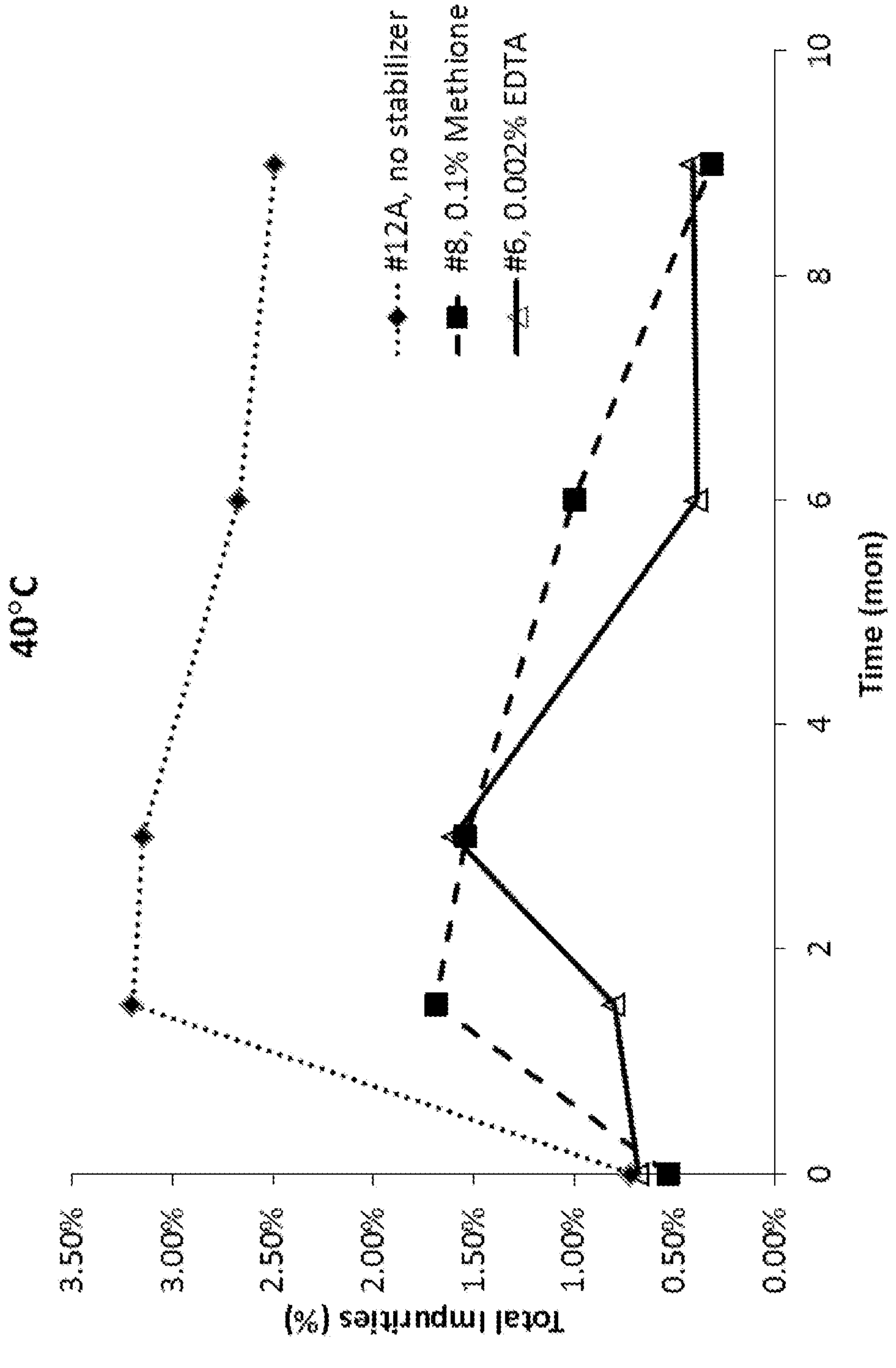
FIG. 23 is a graph depicting the change of total impurities for Naloxone injection formulation #6 (0.002% EDTA), #8 (0.1% Methionine), #12A (no stabilizer) at 40° C.
Figure 24:
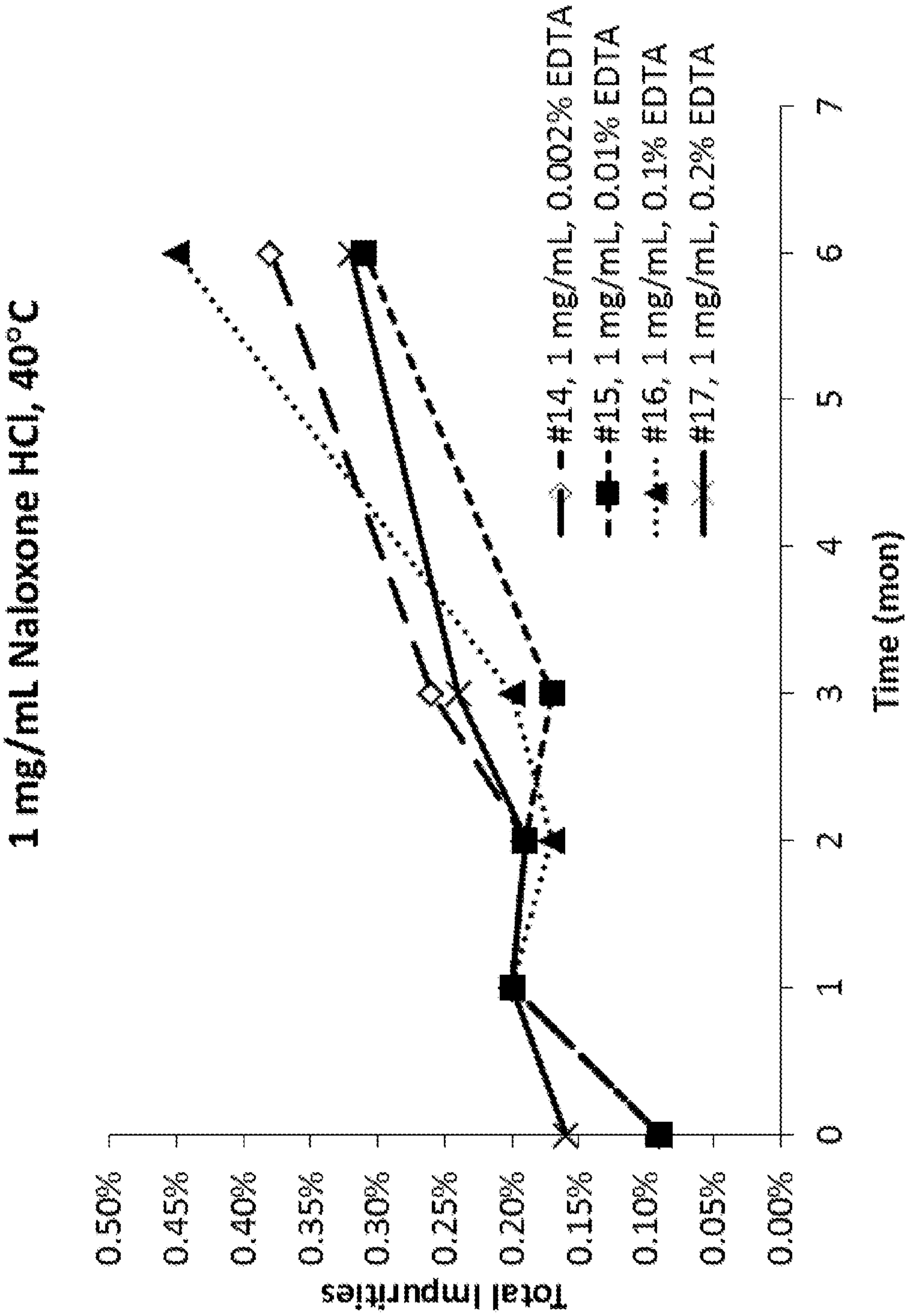
FIG. 24 is a graph depicting the change of total impurities for Naloxone injection formulations at 1 mg/mL with different levels of EDTA at 40° C.

As shown in Table 12 and FIGS. 23 and 24, the presence of EDTA and Methionine both significantly improve the stability at 40° C. and 60° C. with much less impurities generated during stability study, in comparison to F #12A.

TABLE 8

Composition of Prototype Formulations for Naloxone Hydrochloride Injection

| Batch# | #6 | #7 | #8 | #9 | #11 | #12A | #12B | #12C | #13 |
|---|---|---|---|---|---|---|---|---|---|
| | Composition (in 1 mL) | | | | | | | | |
| Naloxone HCl dihydrate (mg) | 1.1 | 1.1 | 1.1 | 1.1 | 1.1 | | 1.1 | | 5.5 |
| Sodium Chloride (mg) | 8.35 | 8.35 | 8.35 | 8.35 | 8.35 | | 8.35 | | 8.00 |
| Edetate disodium (mg) | 0.02 | — | — | — | — | | — | | — |
| Citric acid (mg) | — | 0.02 | — | — | — | | — | | — |
| Methionine | — | — | 1 | — | — | | — | | — |
| Ascorbic acid (mg) | — | — | — | 1 | — | | — | | — |
| Na metabisulfite (mg) | — | — | — | — | — | | — | | — |
| Monothio-glycerol (mg) | — | — | — | — | 1 | | — | | — |
| Hydrochloric Acid or NaOH* | QS, pH 3.5 | QS, pH 3.5 | QS, pH 3.5 | QS, pH 3.5 | QS, pH 3.5 | | QS, pH 3.5 | | QS, pH 3.5 |
| Water for Injection | QS to 1 mL | QS to 1 mL | QS to 1 mL | QS to 1 mL | QS to 1 mL | | QS to 1 mL | | QS to 1 mL |
| Targeted pH* | 3.5 | 3.5 | 3.5 | 3.5 | 3.5 | | 3.5 | | 3.5 |
| Syringe | Ompi 22G, | Ompi 22G | Ompi 22G | Ompi 22G | Ompi 22G | Ompi 22G | Ompi 22G | Schott 27G, 1469924 | Ompi 22G |
| Stopper | West 10149695 | West 10149695 | West 10149695 | West 10149695 | West 10149695 | West 10149695 | West 10149695 | Schott 1195953 | West 10149695 |

TABLE 9

Stability data of Naloxone Hydrochloride Injection in different combination of primary packaging components

| | 25° C. | | | | | 40° C. | | | | | 60° C. | | | |
|---|---|---|---|---|---|---|---|---|---|---|---|---|---|---|
| Test | Initial | 2M | 3M | 6M | 9M | 1.5M | 2M | 3M | 6M | 9M | 1.5M | 2M | 3M | 6M |
| Formulation# 12A, 1 mg/mL Naloxone, Ompi PFS/West Stopper | | | | | | | | | | | | | | |
| Assay | 101.26% | 99.61% | 100.29% | 100.95% | 101.29% | 102.73% | 99.86% | 99.69% | 99.44% | 100.44% | 99.02% | 99.59% | 98.21% | 93.34% |
| Impurities | 0.72% | 0.37% | 0.88% | 0.34% | 0.27% | 3.20% | 5.19% | 3.15% | 2.67% | 2.49% | 3.75% | 5.80% | 8.05% | 6.65% |
| Formulation# 12B, 1 mg/mL Naloxone, Ompi PFS/Schott Stopper | | | | | | | | | | | | | | |
| Assay | 101.26% | 100.08% | 100.21% | 100.96% | 101.34% | 102.80% | 99.72% | 99.76% | 99.54% | 98.88% | 98.18% | 98.55% | 97.31% | 89.22% |
| Impurities | 0.72% | 0.36% | 0.86% | 0.39% | 0.25% | 1.90% | 3.85% | 3.41% | 2.37% | 2.68% | 4.67% | 6.78% | 11.21% | 8.89% |

TABLE 9-continued

Stability data of Naloxone Hydrochloride Injection in different combination of primary packaging components

| | 25° C. | | | | | 40° C. | | | | | 60° C. | | | |
|---|---|---|---|---|---|---|---|---|---|---|---|---|---|---|
| Test | Initial | 2M | 3M | 6M | 9M | 1.5M | 2M | 3M | 6M | 9M | 1.5M | 2M | 3M | 6M |
| Formulation# 12C, 1 mg/mL Naloxone, Schott PFS/West Stopper | | | | | | | | | | | | | | |
| Assay | 101.26% | 100.60% | 100.44% | 95.00% | 99.12% | 102.90% | 99.28% | 99.49% | 98.69% | 101.32% | 98.23% | 98.47% | 98.20% | 81.29% |
| Impurities | 0.72% | 0.56% | 0.80% | 0.37% | 0.30% | 2.11% | 3.23% | 4.23% | 3.55% | 2.64% | 3.22% | 8.65% | 8.85% | 12.08% |

TABLE 10

Stability data of Naloxone Hydrochloride Injection in two different concentrations

| | 25° C. | | | | | 40° C. | | | | | 60° C. | | | |
|---|---|---|---|---|---|---|---|---|---|---|---|---|---|---|
| Test | Initial | 2M | 3M | 6M | 9M | 1.5M | 2M | 3M | 6M | 9M | 1.5M | 2M | 3M | 6M |
| Formulation# 12A, 1 mg/mL Naloxone, Ompi PFS/West Stopper | | | | | | | | | | | | | | |
| Assay | 101.26% | 99.61% | 100.29% | 100.95% | 101.29% | 102.73% | 99.86% | 99.69% | 99.44% | 100.44% | 99.02% | 99.59% | 98.21% | 93.34% |
| Impurities | 0.72% | 0.37% | 0.88% | 0.34% | 0.27% | 3.20% | 5.19% | 3.15% | 2.67% | 2.49% | 3.75% | 5.80% | 8.05% | 6.65% |
| Formulation# 13, 5 mg/mL Naloxone, Ompi PFS/West Stopper | | | | | | | | | | | | | | |
| Assay | 99.66% | 96.56% | 98.94% | 97.98% | 93.85% | 101.04% | 98.51% | 98.06% | 96.06% | 97.08% | 94.32% | 97.46% | 96.54% | 92.67% |
| Impurities | 0.56% | 0.22% | 0.51% | 0.27% | 0.21% | 3.19% | 4.73% | 3.84% | 2.86% | 2.93% | 4.34% | 7.43% | 8.13% | 5.34% |

TABLE 11

Stability Data of Prototype Formulations of Naloxone hydrochloride Injection at 40° C. and 60° C.

| | Item | | | | | | | | | | | |
|---|---|---|---|---|---|---|---|---|---|---|---|---|
| | F#6 0.002% EDTA | | F#7 0.002% citric acid | | F#8 0.1% Methione | | F#9 0.1% ascorbic acid | | F#11 0.1% monothiolglycerol | | F#12A No additive | |
| Test | Initial | 1.5M | Initial | 1.5M | Initial | 1.5M | Initial | 1.5M | Initial | 1.5M | Initial | 1.5M |
| | 40° C. | | | | | | | | | | | |
| Assay | 99.64% | 100.90% | 99.98% | 99.38% | 101.48% | 101.70% | 100.01% | 81.87% | 101.34% | 83.62% | 101.26% | 102.80% |
| Impurities | 0.68% | 0.80% | 0.71% | 3.43% | 0.53% | 0.10% | 0.64% | 49.26% | 0.72% | 43.51% | 0.72% | 1.90% |
| | 60° C. | | | | | | | | | | | |
| Assay | 99.64% | 100.25% | 99.98% | 96.62% | 101.48% | 100.40% | 100.01% | 63.74% | 101.34% | 68.49% | 101.34% | 98.18% |
| Impurities | 0.68% | 0.84% | 0.71% | 3.40% | 0.53% | 0.48% | 0.64% | 62.48% | 0.72% | 39.26% | 0.72% | 4.67% |

TABLE 12

Stability data of Formulation #6, #8, #12A at 25 ° C., 40 ° C., and 60 ° C.

| | 25° C. | | | | | 40° C. | | | | | 60° C. | | | |
|---|---|---|---|---|---|---|---|---|---|---|---|---|---|---|
| Test | Initial | 2M | 3M | 6M | 9M | 1.5M | 2M | 3M | 6M | 9M | 1.5M | 2M | 3M | 6M |
| Formulation# 6, 1 mg/mL Naloxone, 0.002% EDTA, Ompi PFS/West Stopper | | | | | | | | | | | | | | |
| Assay | 99.64% | 99.05% | 99.80% | 100.17% | 99.95% | 100.90% | 100.08% | 99.04% | 101.29% | 102.49% | 100.25% | 100.01% | 99.62% | 103.10% |
| Impurities | 0.68% | 0.33% | 0.52% | 0.35% | 0.19% | 0.80% | 0.76% | 1.60% | 0.39% | 0.41% | 0.84% | 1.93% | 2.75% | 2.36% |
| Formulation# 8, 1 mg/mL Naloxone, 0.1% Methionine, Ompi PFS/West Stopper | | | | | | | | | | | | | | |
| Assay | 101.48% | 99.40% | 100.57% | 99.95% | 99.88% | 101.70% | 100.45% | 99.93% | 100.37% | 102.57% | 100.40% | 100.35% | 100.04% | 92.12% |
| Impurities | 0.53% | 0.23% | 0.81% | 0.29% | 0.12% | 1.69% | 2.74% | 1.54% | 1.00% | 0.31% | 0.48% | 3.57% | 2.46% | 7.57% |

TABLE 12-continued

| Stability data of Formulation #6, #8, #12A at 25 ° C., 40 ° C., and 60 ° C. | | | | | | | | | | | | | | |
|---|---|---|---|---|---|---|---|---|---|---|---|---|---|---|
| Formulation# 12A, 1 mg/mL Naloxone, Ompi PFS/West Stopper | | | | | | | | | | | | | | |
| Assay | 101.26% | 99.61% | 100.29% | 100.95% | 101.29% | 102.73% | 99.86% | 99.69% | 99.44% | 100.44% | 99.02% | 99.59% | 98.21% | 93.34% |
| Impurities | 0.72% | 0.37% | 0.88% | 0.34% | 0.27% | 3.20% | 5.19% | 3.15% | 2.67% | 2.49% | 3.75% | 5.80% | 8.05% | 6.65% |

Example 6: Study on the Level of EDTA

To evaluate the level of EDTA on the stability improvement of Naloxone HCl injection, eight formulations were prepared with increasing EDTA concentrations from 0.002% to 0.2% for both 1 mg/mL and 5 mg/mL Naloxone HCl concentrations, as described in Table 13. The formulations were filled into 1 mL long Ompi syringe and closed with West plunger stopper described in Table 5 and subjected to stability study at 25, 40, and 60° C.

TABLE 13

Composition of modified Naloxone Hydrochloride Injection with Different Levels of EDTA

| Formulation# | #14 (previous #6) | #15 | #16 | #17 | #18 | #19 | #20 | #21 |
|---|---|---|---|---|---|---|---|---|
| Naloxone HCl dihydrate (mg) | 1.10 | 1.10 | 1.10 | 1.10 | 5.50 | 5.50 | 5.50 | 5.50 |
| Sodium Chloride (mg) | 8.35 | 8.32 | 8.01 | 7.66 | 7.71 | 7.68 | 7.37 | 7.02 |
| Edetate disodium (mg) | 0.02 | 0.10 | 1.0 | 2.0 | 0.02 | 0.10 | 1.0 | 2.0 |
| Hydrochloric Acid or NaOH | QS, pH 3.5 | QS, pH 3.5 | QS, pH 3.5 | QS, pH 3.5 | QS, pH 3.5 | QS, pH 3.5 | QS, pH 3.5 | QS, pH 3.5 |
| Water for Injection | QS to 1 mL | QS to 1 mL | QS to 1 mL | QS to 1 mL | QS to 1 mL | QS to 1 mL | QS to 1 mL | QS to 1 mL |
| Targeted pH | 3.5 | 3.5 | 3.5 | 3.5 | 3.5 | 3.5 | 3.5 | 3.5 |
| Syringe | | | | Ompi 22G, | | | | |
| Stopper | | | | West 10149695 | | | | |

Figure 25:
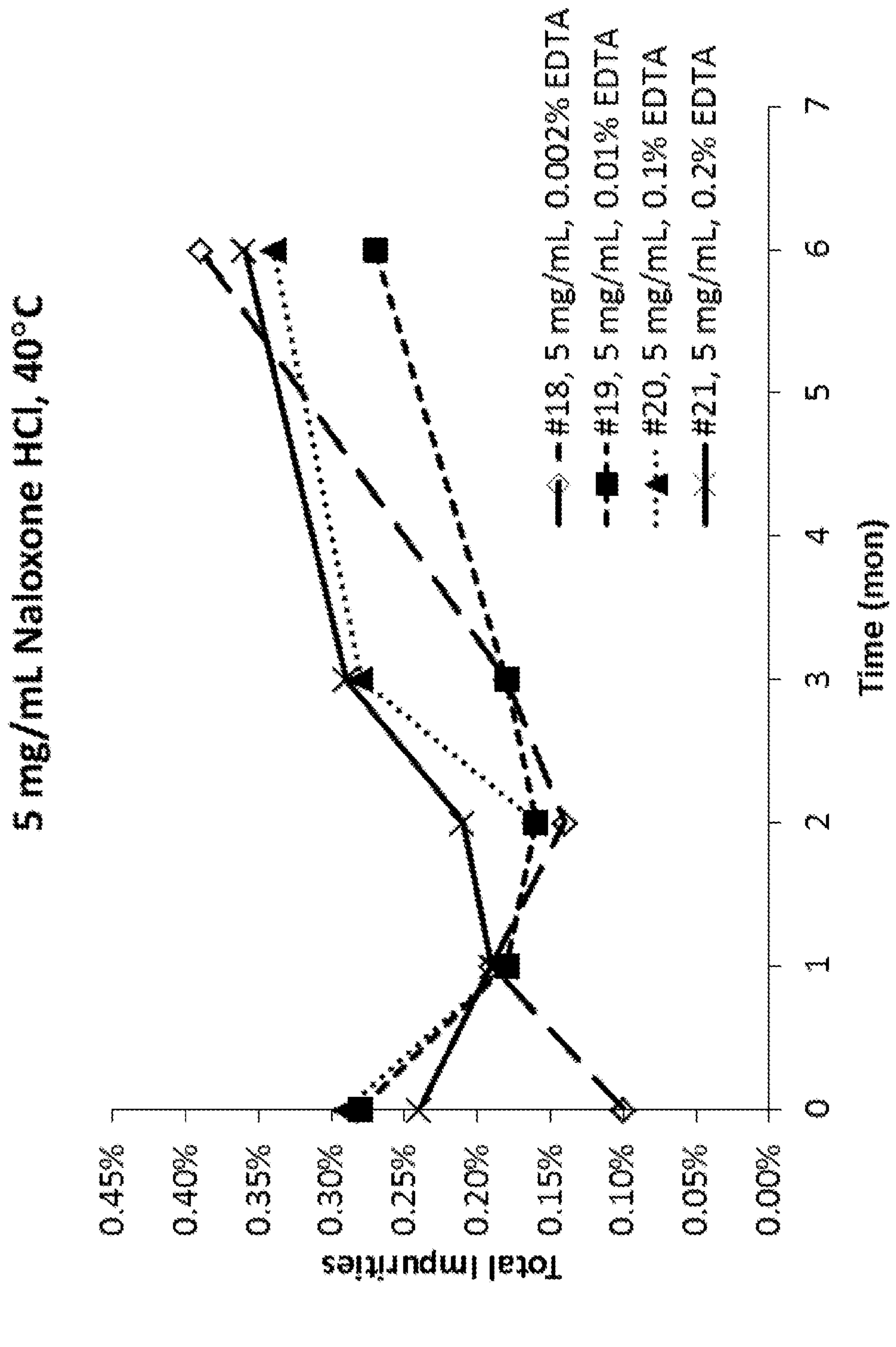
FIG. 25 is a graph depicting the change of total impurities for Naloxone injection formulations at 5 mg/mL with different levels of EDTA at 40° C.

The stability data for the modified formulations with different levels of EDTA at 25, 40, 60° C. up to 6 months are provided in Table 14 and Table 15, which clearly demonstrate the stabilization effect of EDTA. For both concentrations at 1 mg/mL and 5 mg/mL, the presence of 0.002% to 0.2% EDTA led to no detectable increased in total impurities during the storage at 25° C. and minor increase (0.1%-0.3%) at 40° C. for six months storage. It appears that the use of 0.01% EDTA gave the least increase in total impurities for both 1 mg/mL and 5 mg/mL formulations, as shown in FIGS. 24 and 25.

Figure 26:
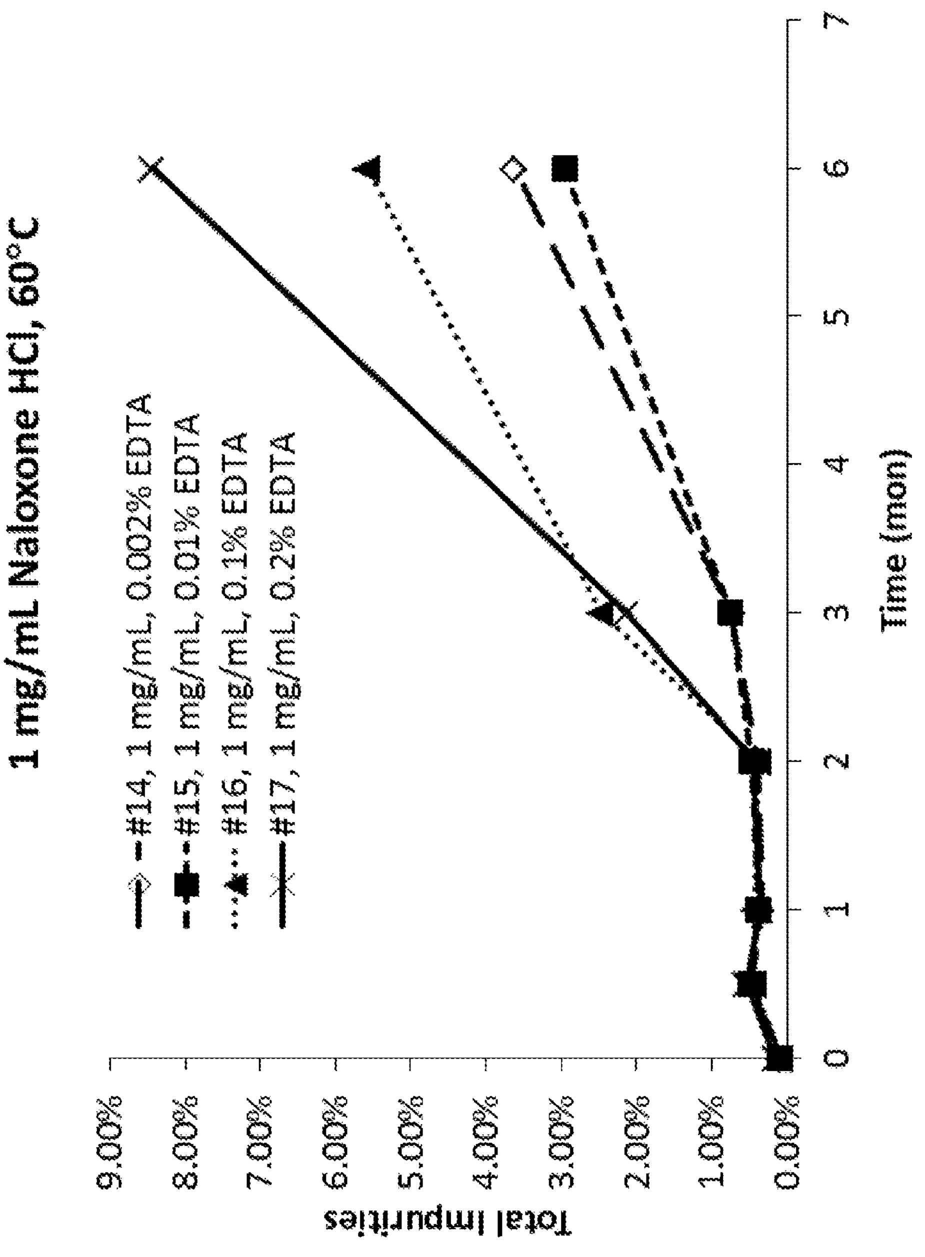
FIG. 26 is a graph depicting the change of total impurities for Naloxone injection formulations at 1 mg/mL with different levels of EDTA at 60° C.
Figure 27:
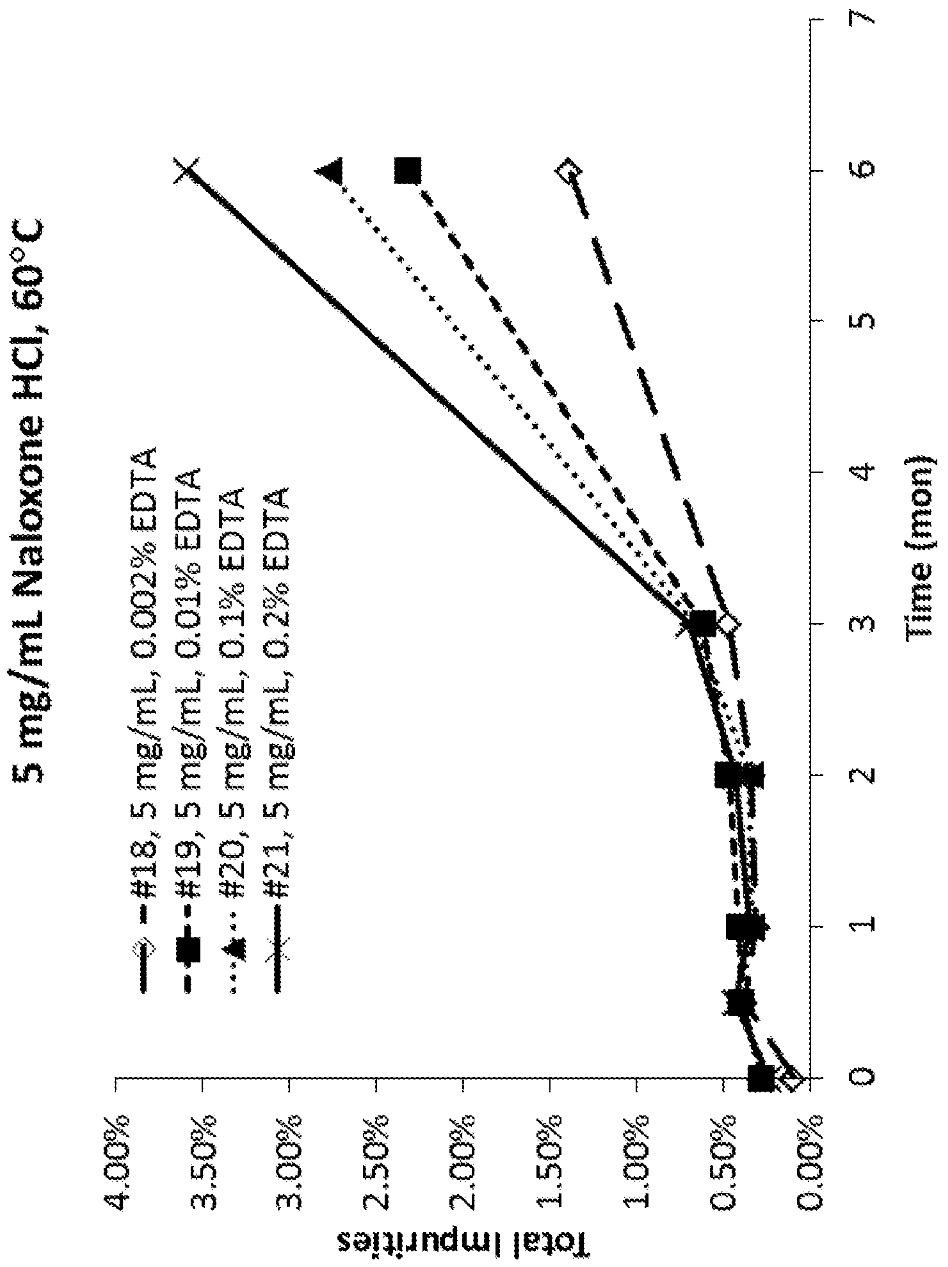
FIG. 27 is a graph depicting the change of total impurities for Naloxone injection formulations at 5 mg/mL with different levels of EDTA at 60° C.
Figure 28:
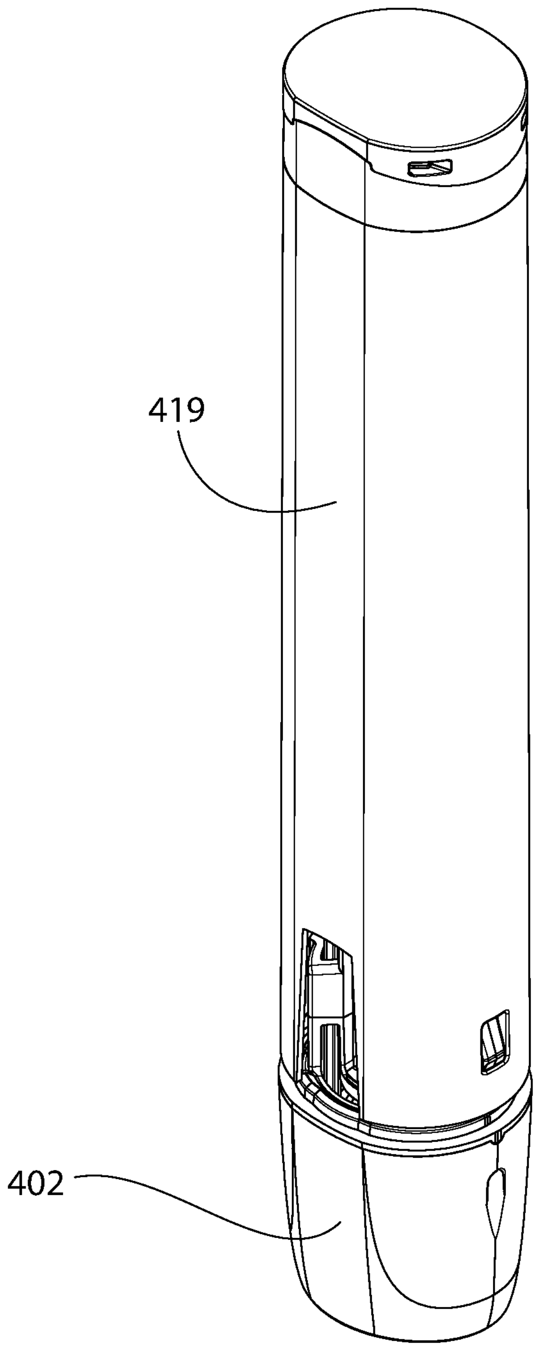
FIG. 28 is a perspective view of an injection device of an exemplary embodiment of the present disclosure.
Figure 29:
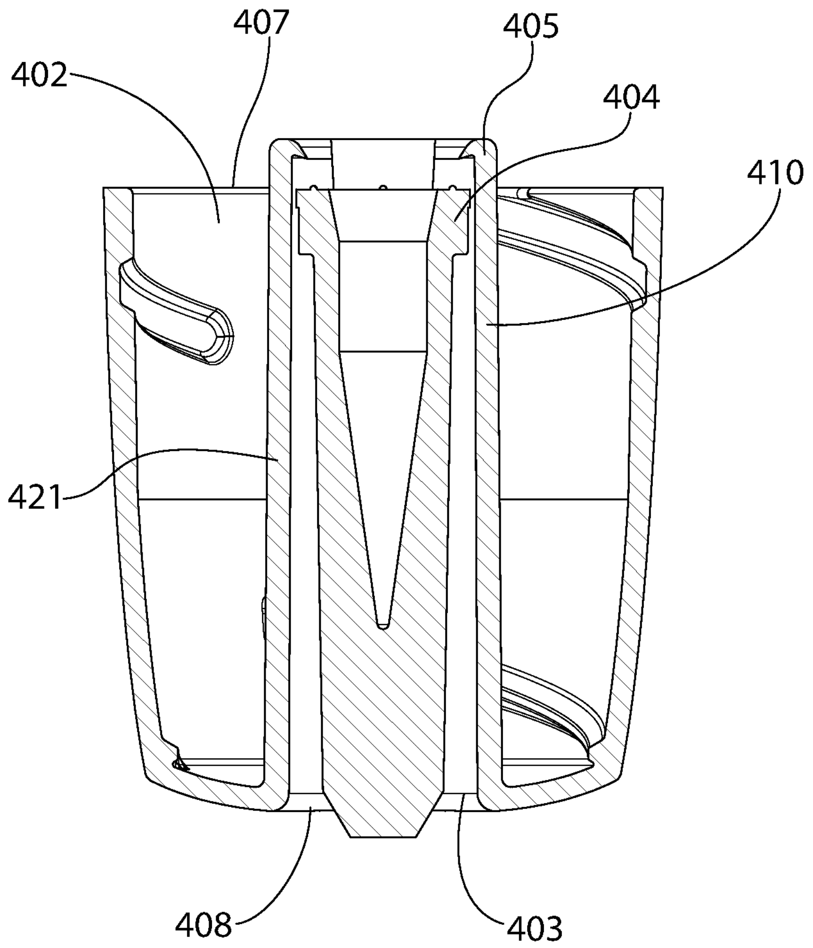
FIG. 29 is a close-up sectional view of the safety cap of FIG. 28.

For the stability samples stored at 60° C., impurities increase were only observed after 3 months storage and became significant after 6 month storage, with high EDTA level at 0.1% and 0.2% leading to more impurities observed (FIGS. 26 and 27). Thus, selecting levels of EDTA between 0.01-0.1% is considered appropriate to offer a Naloxone hydrochloride injection an optimal stability profile.

TABLE 14

Stability data of 1 mg/mL Naloxone HCl Injection with Different Levels of EDTA

| | 25° C. | | | 40° C. | | | | 60° C. | | | | |
|---|---|---|---|---|---|---|---|---|---|---|---|---|
| Test | Initial | 3M | 6M | 1M | 2M | 3M | 6M | 0.5M | 1M | 2M | 3M | 6M |
| Formulation# 14, 1 mg/mL Naloxone, 0.002% EDTA | | | | | | | | | | | | |
| Assay | 101.79% | 100.44% | 100.62% | 100.45% | 99.90% | 100.99% | 101.43% | 99.48% | 99.89% | 101.73% | 103.34% | 100.40% |
| Impurities | 0.09% | 0.14% | 0.20% | 0.20% | 0.19% | 0.26% | 0.38% | 0.47% | 0.34% | 0.39% | 0.74% | 3.63% |

TABLE 14-continued

Stability data of 1 mg/mL Naloxone HCl Injection with Different Levels of EDTA

| | 25° C. | | | 40° C. | | | | 60° C. | | | | |
|---|---|---|---|---|---|---|---|---|---|---|---|---|
| Test | Initial | 3M | 6M | 1M | 2M | 3M | 6M | 0.5M | 1M | 2M | 3M | 6M |
| Formulation# 15, 1 mg/mL Naloxone, 0.01% EDTA | | | | | | | | | | | | |
| Assay | 101.77% | 101.02% | 101.20% | 100.33% | 100.67% | 101.78% | 102.46% | 100.82% | 100.81% | 102.30% | 103.77% | 105.56% |
| Impurities | 0.09% | 0.13% | 0.23% | 0.20% | 0.19% | 0.17% | 0.31% | 0.49% | 0.38% | 0.47% | 0.75% | 2.96% |
| Formulation# 16, 1 mg/mL Naloxone, 0.1% EDTA | | | | | | | | | | | | |
| Assay | 100.99% | 99.69% | 100.23% | 99.10% | 99.57% | 100.48% | 100.98% | 99.95% | 99.12% | 100.99% | 99.74% | 100.58% |
| Impurities | 0.09% | 0.16% | 0.20% | 0.20% | 0.17% | 0.20% | 0.45% | 0.45% | 0.43% | 0.38% | 2.47% | 5.58% |
| Formulation# 17, 1 mg/mL Naloxone, 0.2% EDTA | | | | | | | | | | | | |
| Assay | 100.44% | 99.48% | 99.97% | 99.07% | 100.11% | 100.42% | 101.65% | 99.66% | 99.24% | 100.71% | 100.20% | 97.16% |
| Impurities | 0.16% | 0.15% | 0.19% | 0.20% | 0.19% | 0.24% | 0.32% | 0.54% | 0.36% | 0.46% | 2.12% | 8.44% |

TABLE 15

Stability data of 5 mg/mL Naloxone HCl Injection with Different Levels of EDTA

| | 25° C. | | | 40° C. | | | | 60° C. | | | | |
|---|---|---|---|---|---|---|---|---|---|---|---|---|
| Test | Initial | 3M | 6M | 1M | 2M | 3M | 6M | 0.5 M | 1M | 2M | 3M | 6M |
| Formulation# 18, 5 mg/mL Naloxone, 0.002% EDTA | | | | | | | | | | | | |
| Assay | 98.59% | 96.42% | 96.16% | 95.81% | 97.05% | 96.50% | 97.21% | 98.51% | 95.44% | 97.63% | 98.21% | 100.42% |
| Impurities | 0.10% | 0.15% | 0.20% | 0.19% | 0.14% | 0.18% | 0.39% | 0.38% | 0.31% | 0.34% | 0.47% | 1.39% |
| Formulation# 19, 5 mg/mL Naloxone, 0.01% EDTA | | | | | | | | | | | | |
| Assay | 99.21% | 96.42% | 97.06% | 96.12% | 97.00% | 97.31% | 97.46% | 98.50% | 96.75% | 97.81% | 97.31% | 100.15% |
| Impurities | 0.28% | 0.16% | 0.18% | 0.18% | 0.16% | 0.18% | 0.27% | 0.40% | 0.41% | 0.47% | 0.62% | 2.32% |
| Formulation# 20, 5 mg/mL Naloxone, 0.1% EDTA | | | | | | | | | | | | |
| Assay | 98.41% | 96.32% | 96.06% | 95.22% | 96.67% | 96.32% | 97.06% | 98.45% | 95.78% | 97.14% | 98.04% | 98.11% |
| Impurities | 0.29% | 0.15% | 0.16% | 0.18% | 0.16% | 0.28% | 0.34% | 0.40% | 0.34% | 0.35% | 0.67% | 2.78% |
| Formulation# 21, 5 mg/mL Naloxone, 0.2% EDTA | | | | | | | | | | | | |
| Assay | 98.49% | 96.45% | 97.25% | 96.04% | 97.68% | 97.48% | 97.24% | 98.96% | 96.51% | 97.89% | 98.46% | 97.30% |
| Impurities | 0.24% | 0.14% | 0.16% | 0.19% | 0.21% | 0.29% | 0.36% | 0.43% | 0.35% | 0.43% | 0.70% | 3.59% |

Example 7: Formulation Process Development

Based on the prototype stability data, the medicament comprising Naloxone hydrochloride includes between 0.01-0.1% edetate disodium to enhance the stability. Since the active and inactive ingredients are very soluble in water, the compounding process will be carried out by mixing to dissolve all ingredients with no heating required. The compounding procedure will be developed during the technical transfer to a third party manufacturer.

Example 8: Composition and Batch Formula of Naloxone Hydrochloride Injection USP The component and composition of an example Naloxone hydrochloride injection USP stabilized formulation are described in Table 16 and Table 17. Each 0.4 mL of sterile solution contains 0.4 mg (1 mg/mL) or 2.0 mg (5 mg/mL) of Naloxone hydrochloride in water for injection. It also contains sodium chloride and edetate disodium. pH is adjusted to 3.0 to 4.5 with hydrochloride or sodium hydroxide.

TABLE 16

Unit Composition for Naloxone Hydrochloride Injection USP, 0.4 mg

| Component | Quality Standard | Function | wt/v % | Quantity per 0.4 mL |
|---|---|---|---|---|
| Naloxone HCl | USP | Active Ingredient | 0.100%* | 0.400 mg |
| Sodium Chloride | USP | Tonicity Adjuster | 0.832% | 3.33 mg |
| Edetate Disodium | USP | Chelating agent | 0.01% | 0.04 mg |
| Hydrochloric Acid | NF | pH Adjustor | q.s. pH | q.s. pH |
| Sodium Hydroxide | NF | pH Adjustor | q.s. pH | q.s. pH |
| Water for Injection | USP | Solvent | q.s. | q.s. to 0.4 mL |

*Equivalent to 0.110% Naloxone HCl dihydrate

TABLE 17

| Unit Composition for Naloxone Hydrochloride Injection USP 2.0 mg | | | | |
|---|---|---|---|---|
| Component | Quality Standard | Function | wt/v % | Quantity per 0.4 mL |
| Naloxone HCl | USP | Active Ingredient | 0.500%* | 2.00 mg |
| Sodium Chloride | USP | Tonicity Adjuster | 0.768% | 3.07 mg |
| Edetate Disodium | USP | Chelating agent | 0.01% | 0.04 mg |
| Hydrochloric Acid | NF | pH Adjustor | q.s. pH | q.s. pH |
| Sodium Hydroxide | NF | pH Adjustor | q.s. pH | q.s. pH |
| Water for Injection | USP | Solvent | q.s. | q.s. to 0.4 mL |

*Equivalent to 0.550% Naloxone HCl dihydrate

Batch formulas at five (5) liters are given in Table 18 and 19.

TABLE 18

| Batch Formula for Naloxone Hydrochloride Injection USP 0.4 mg | | | | |
|---|---|---|---|---|
| Component | Quality Standard | Function | wt/v % | Quantity at 5 Liter (gram) |
| Naloxone HCl | USP | Active Ingredient | 0.100%[1] | 5.00[2] |
| Sodium Chloride | USP | Tonicity Adjuster | 0.832% | 41.6 |
| Edetate Disodium | USP | Chelating agent | 0.01% | 0.50 |
| Hydrochloric Acid | NF | pH Adjustor | q.s. pH | q.s. pH |
| Sodium Hydroxide | NF | pH Adjustor | q.s. pH | q.s. pH |
| Water for Injection | USP | Solvent | q.s. | q.s. to 5 Liter |

[1]Equivalent to 0.110% of Naloxone HCl dihydrate
[2]Equivalent to 5.50 g of Naloxone HCl dihydrate

TABLE 19

| Batch Formula for Naloxone Hydrochloride Injection USP 2.0 mg | | | | |
|---|---|---|---|---|
| Component | Quality Standard | Function | wt/v % | Quantity at 5 Liter (gram) |
| Naloxone HCl | USP | Active Ingredient | 0.500%[1] | 25.0[2] |
| Sodium Chloride | USP | Tonicity Adjuster | 0.768% | 38.4 |
| Edetate Disodium | USP | Chelating agent | 0.01% | 0.50 |
| Hydrochloric Acid | NF | pH Adjustor | q.s. pH | q.s. pH |
| Sodium Hydroxide | NF | pH Adjustor | q.s. pH | q.s. pH |
| Water for Injection | USP | Solvent | q.s. | q.s. to 5 Liter |

[1]Equivalent to 0.550% of Naloxone HCl dihydrate
[2]Equivalent to 27.5 g of Naloxone HCl dihydrate

Example 9: Filter Compatibility Study

Aseptic process to prepare sterile injection for Naloxone hydrochloride comprises of a sterile filtration step. A Millipore Durapore™ 0.22 μm hydrophilic polyvinylidene fluoride (PVDF) filter is the leading choice since the filter membrane is commonly used for the sterile filtration due to acceptable compatibility with aqueous solution, exceptionally high flow rates and sterility assurance. A study was carried out to evaluate the absorptive losses of Naloxone during filtration. A 1 mg/mL Naloxone hydrochloride injection solution was filtered through a 33 mm diameter sterile syringe filter with a 0.22 μm pore size hydrophilic PVDF membrane and samples were collected at 1 mL, 2 mL, 3 mL, 4 mL, 5 mL, and 10 mL during the filtration for HPLC analysis. As shown in Table 20, there was minimal absorption of naloxone by the PVDF filter since the first 1 mL solution has assay value matching the unfiltered solution. In addition, the impurity level stayed constant during filtration, furtherly confirming the compatibility of naloxone solution with PVDF filter.

TABLE 20

| Filter Compatibility Study of Naloxone Hydrochloride Injection Solution 1 mg/mL with PVDF filter | | |
|---|---|---|
| Filtrate | Assay of Naloxone | Total Impurities (%) |
| Unfiltered | 101.4% | 0.14% |
| 1 mL | 101.8% | 0.15% |
| 2 mL | 102.0% | 0.15% |
| 3 mL | 102.2% | 0.14% |

TABLE 20-continued

Filter Compatibility Study of Naloxone Hydrochloride Injection Solution 1 mg/mL with PVDF filter

| Filtrate | Assay of Naloxone | Total Impurities (%) |
|---|---|---|
| 4 mL | 102.0% | 0.14% |
| 5 mL | 102.0% | 0.15% |
| 10 mL | 102.0% | 0.15% |

Example 10: Bulk Hold Study

A bulk hold study of laboratory batches of Naloxone hydrochloride injection at 1 mg/ml and 5 mg/mL was carried out to study the stability of naloxone during a routine production holding time up to 72 hours. Product samples were taken for HPLC analysis after holding at room temperature for 24, 48, and 72 hours. As shown in Table 21, there is no change in Naloxone assay and total impurities after the solutions were on hold at room temperature for 72 hours.

TABLE 21

Bulk Hold Study of Naloxone hydrochloride Solution 1 mg/mL and 5 mg/mL

| | 1 mg/mL Formulation | | 5 mg/mL Formulation | |
|---|---|---|---|---|
| Hold time | Assay of Naloxone | Total Impurities (%) | Assay of Naloxone | Total Impurities (%) |
| Initial | 99.8% | 0.15% | 96.3% | 0.15% |
| 24 hours | 99.7% | 0.16% | 96.7% | 0.15% |
| 48 hours | 99.9% | 0.17% | 96.7% | 0.15% |
| 72 hours | 99.8% | 0.15% | 96.8% | 0.14% |

The invention claimed is:

1. An injector, comprising:

a housing;

a cap detachably coupled to the housing;

a medicament container including a medicament comprising about 1.1 mg/mL naloxone HCl dihydrate, about 1 mg/mL methionine, and a pharmaceutically acceptable carrier wherein the medicament after storage at 25° C. for 2 to 9 months has between 0.12% and 0.81% impurities;

a ram assembly having a ram configured to pressurize the medicament container for expelling the medicament therefrom, the ram assembly including a trigger engagement member;

an energy source associated with the ram for powering the ram to expel medicament from the medicament container;

a trigger member disposed about an axis, the trigger member moveable between a pre-firing configuration and a firing configuration, wherein medicament is expelled from the medicament container when the trigger member is in the firing configuration; and a needle guard moveably coupled to the housing, the needle guard movable between a storage position and a pre-injection position, wherein the needle guard moves from the storage position to the pre-injection position as the cap is detached from the housing.

2. The injector of claim 1, further comprising:

a needle in fluid communication with the medicament container, and a needle shield at least partially surrounding the needle.

3. The injector of claim 2, wherein the needle shield axially extends past the cap in a distal direction.

4. The injector of claim 2, wherein the cap includes an end wall with an end wall opening.

5. The injector of claim 4, wherein at least a portion of the needle shield is within the end wall opening when the cap is coupled to the housing.

6. The injector of claim 2, wherein the cap includes a needle shield remover which removes the needle shield from the needle as the cap is detached from the housing.

7. The injector of claim 6, wherein detaching the cap from the housing simultaneously moves the needle guard to the pre-injection position and removes the needle shield from the needle as the cap is detached from the housing.

8. The injector of claim 1, wherein an end of the needle guard is further away from the housing in the storage position than in an injecting position.

9. The injector of claim 5, wherein the needle guard is in the pre-injection position before a proximal end of the cap is moved axially beyond a distal end of the needle.

10. The injector of claim 1, wherein in the storage position, the trigger member is in the pre-firing configuration and the needle guard is partially retracted with respect to the housing.

11. The injector of claim 1 wherein the needle guard moves the trigger member in a proximal direction from the pre-firing configuration to the firing configuration wherein the trigger engagement member is released to allow the energy source to fire the ram.

12. The injector of claim 11, wherein the energy source acts on the ram to deliver medicament from the medicament container when the needle guard is in an injection position.

13. The injector of claim 1, wherein the needle guard includes a firing initiation member associated with the trigger member and the needle guard is movable proximally with respect to the housing from the pre-injection position to an injection position, and wherein as the needle guard moves proximally, the firing initiation member moves the trigger member from the pre-firing configuration to the firing configuration.

14. The injector of claim 1, further comprising an end cap, the end cap comprising a ram holding member that axially retains the ram assembly in a proximal position against action of the energy source in the pre-firing configuration.

15. The injector of claim 14, wherein the ram holding member engages the trigger engagement member to axially retain the ram assembly in a proximal position against action of the energy source in the pre-firing configuration.

16. The injector of claim 14, wherein the trigger member includes an aperture and in the firing configuration, the ram is disengaged from the aperture, and the energy source overcomes the engagement between the trigger engagement member and the ram holding member.

17. The injector of claim 14, wherein the ram holding member includes a projection that includes a bulge and a groove that are engaged with the trigger engagement member, and an aperture of the trigger member retains the engagement of the trigger engagement member with the bulge and groove in the pre-firing configuration.

18. The injector of claim 1, further comprising a container support that is configured for holding the medicament container during injection, and wherein the ram assembly is configured to engage the container support to prevent movement of the ram assembly after an injection.

19. The injector of claim 1, wherein the needle guard is movable to a post injection position, the post injection position being when proximal movement of needle guard is blocked by the ram assembly.

20. The injector of claim 1, wherein a first distance comprises a distance between the distal end of the needle guard and a distal end of the housing when the needle guard is in the storage position, wherein a second distance comprises the distance between the distal end of the needle guard and the distal end of the housing when the needle guard is in the pre-injection position, and wherein the first distance is less than the second distance.

21. The injector of claim 20, wherein a third distance comprises the distance between the distal end of the needle guard and the distal end of the housing when the needle guard is in a post-injection position, wherein the third distance is greater than or equal to the second distance.

22. The injector of claim 1, further comprising:

a biasing element configured to urge the needle guard toward the pre-injection position.

23. The injector of claim 1, the cap further comprising:

an end wall, and an end wall opening extending through the end wall.

24. The injector of claim 1, the cap further comprising:

an arm, and an engagement feature extending from the arm, the engagement feature configured to engage a needle shield coupled to a needle disposed through the end wall opening.

25. The injector of claim 1, wherein the energy source is a compression spring.

26. The injector of claim 18, further comprising:

a sleeve.

* * * * *